US012649053B2

(12) United States Patent
Tussey et al.

(10) Patent No.: US 12,649,053 B2
(45) Date of Patent: Jun. 9, 2026

(54) APPLICATOR AND MICRONEEDLE ARRAY PATCH DELIVERY SYSTEM

(71) Applicant: Terrestrial Bio, Inc., Woburn, MA (US)

(72) Inventors: Lynda Tussey, Winston-Salem, NC (US); Kathryn M. Kosuda, Winchester, MA (US); Matthew Dirckx, Cambridge, MA (US); John Spiridigliozzi, Boston, MA (US); Himabindu Nandivada Bailey, Burlington, MA (US)

(73) Assignee: Terrestrial Bio, Inc., Woburn, MA (US)

( * ) Notice: Subject to any disclaimer, the term of this patent is extended or adjusted under 35 U.S.C. 154(b) by 0 days.

(21) Appl. No.: 19/002,415

(22) Filed: Dec. 26, 2024

(65) Prior Publication Data

US 2026/0048249 A1     Feb. 19, 2026

Related U.S. Application Data

(63) Continuation-in-part of application No. PCT/US2024/034901, filed on Jun. 21, 2024.

(Continued)

(51) Int. Cl.
*A61M 37/00*          (2006.01)

(52) U.S. Cl.
CPC .  *A61M 37/0015* (2013.01); *A61M 2037/0023* (2013.01); *A61M 2037/0046* (2013.01);
(Continued)

(58) Field of Classification Search
CPC ...... A61M 2037/0023; A61M 37/0015; A61M 2037/0046; A61B 5/150977; A61B 5/150984
See application file for complete search history.

(56) References Cited

U.S. PATENT DOCUMENTS 5,703,282  A     12/1997  Kuesell et al.
D1,031,038  S      6/2024  Moeckly et al.
(Continued)

FOREIGN PATENT DOCUMENTS

CN          113368033  A  *  9/2021  ............. A61K 39/39
JP          2014042788        3/2014
(Continued)

OTHER PUBLICATIONS

English Translation of Young KR 20100129576 A (Year: 2010).*

(Continued)

*Primary Examiner* — Nilay J Shah
(74) *Attorney, Agent, or Firm* — DLA Piper LLP (US)

(57)          ABSTRACT

A MAP and applicator system can include a MAP and an applicator. The MAP can include a backing and a plurality of microneedles extending from the backing. The microneedles can include tips with a GLP-1 agonist; and a water-soluble base configured to at least partially dissolve upon contact with a bodily fluid of a subject causing the tip to be released below the skin. The applicator is configured to maintain the MAP; in response to an activation mechanism being activated, release a piston downward into the MAP; and push, via the piston, the MAP downward onto the skin surface of the subject such that the plurality of microneedles penetrate the skin surface and are delivered. Apexes of the microneedles are delivered to the subject at a depth of at least about 600 μm and at least about 70% of the GLP-1 is delivered after release of tips of the microneedles.

12 Claims, 48 Drawing Sheets

Related U.S. Application Data

(60) Provisional application No. 63/712,367, filed on Oct. 25, 2024, provisional application No. 63/683,233, filed on Aug. 14, 2024, provisional application No. 63/522,931, filed on Jun. 23, 2023.

(52) U.S. Cl.
CPC .............. *A61M 2037/0053* (2013.01); *A61M 2037/0061* (2013.01); *A61M 2202/0007* (2013.01); *A61M 2202/06* (2013.01); *A61M 2202/07* (2013.01); *A61M 2205/0216* (2013.01); *A61M 2205/0244* (2013.01); *A61M 2207/10* (2013.01); *A61M 2209/04* (2013.01); *A61M 2210/04* (2013.01)

(56) References Cited

U.S. PATENT DOCUMENTS

| | | | |
|---|---|---|---|
| 2005/0096586 | A1 | 5/2005 | Trautman et al. |
| 2005/0165363 | A1* | 7/2005 | Judson .............. A61M 5/31551 604/209 |
| 2008/0183144 | A1* | 7/2008 | Trautman .......... A61M 37/0015 604/272 |
| 2011/0144594 | A1 | 6/2011 | Sund et al. |
| 2013/0165902 | A1 | 6/2013 | Stumber et al. |
| 2013/0226098 | A1 | 8/2013 | Tokumoto et al. |
| 2014/0088550 | A1 | 3/2014 | Bené et al. |
| 2014/0128818 | A1 | 5/2014 | Ogura et al. |
| 2015/0038897 | A1 | 2/2015 | Daddona et al. |
| 2015/0314117 | A1 | 11/2015 | Arami et al. |
| 2017/0035652 | A1 | 2/2017 | Baker et al. |
| 2020/0289808 | A1 | 9/2020 | Moeckly et al. |
| 2021/0244927 | A1 | 8/2021 | Yoshida et al. |
| 2022/0087930 | A1 | 3/2022 | Gambotto et al. |
| 2022/0241571 | A1 | 8/2022 | Ley et al. |
| 2022/0339416 | A1* | 10/2022 | Kosuda .................. A61K 39/39 |
| 2023/0381477 | A1 | 11/2023 | Prausnitz et al. |
| 2024/0408368 | A1 | 12/2024 | Siddiqui et al. |

FOREIGN PATENT DOCUMENTS

| | | | | |
|---|---|---|---|---|
| JP | 2014042788 A | * | 3/2014 | ........ A61M 37/0015 |
| KR | 20100129576 A | * | 12/2010 | |
| WO | WO-2021125955 A1 | * | 6/2021 | ....... A61B 5/150022 |

OTHER PUBLICATIONS

English translation of JP2014042788 (Year: 2014).*

Translation of Gao et al. (CN 113368033 A) (Year: 2021).*

International Search Report and Written Opinion for International Application No. PCT/US2025/060143, mailed Feb. 13, 2026, 15 pages.

International Search Report and Written Opinion for International Application No. PCT/US2024/034901, mailed Oct. 23, 2024, 09 pages.

International Preliminary Report on Patentability for Application No. PCT/US2024/034901, mailed Jan. 2, 2026, 8 pages.

International Search Report and Written Opinion for Application No. PCT/US2025/060139, mailed on Apr. 23, 2026, 19 pages.

* cited by examiner

105

1100

1100

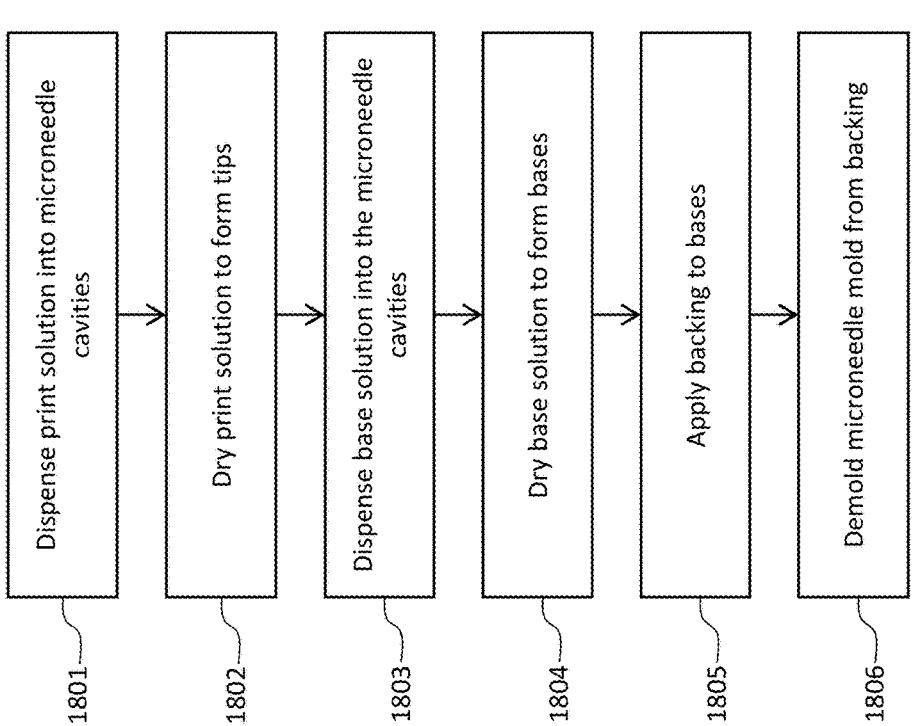
*FIG. 18*

1900
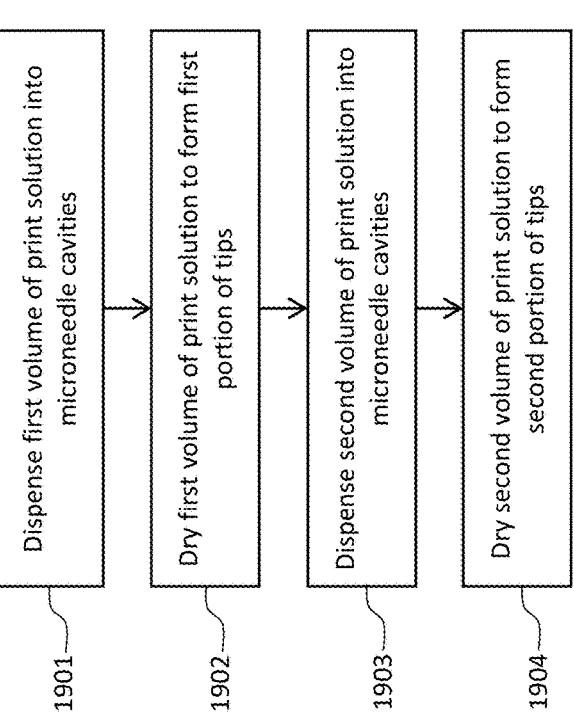
1901 — Dispense first volume of print solution into microneedle cavities
1902 — Dry first volume of print solution to form first portion of tips
1903 — Dispense second volume of print solution into microneedle cavities
1904 — Dry second volume of print solution to form second portion of tips
*FIG. 19*

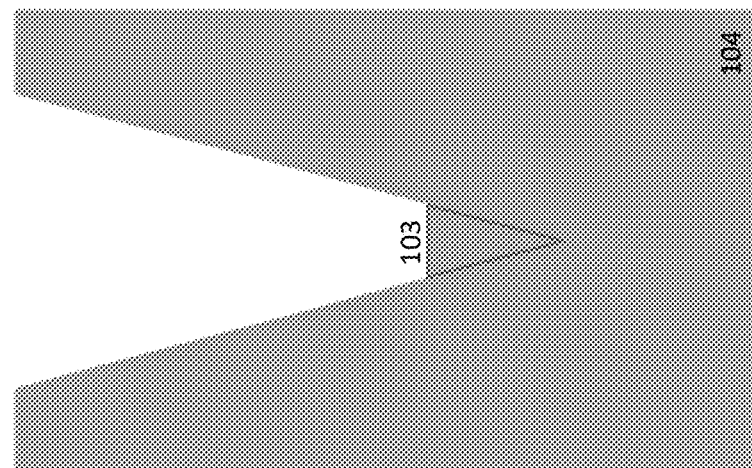
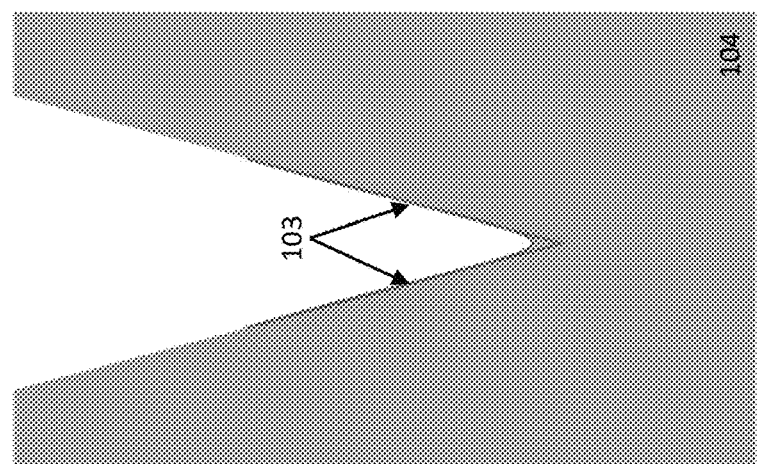
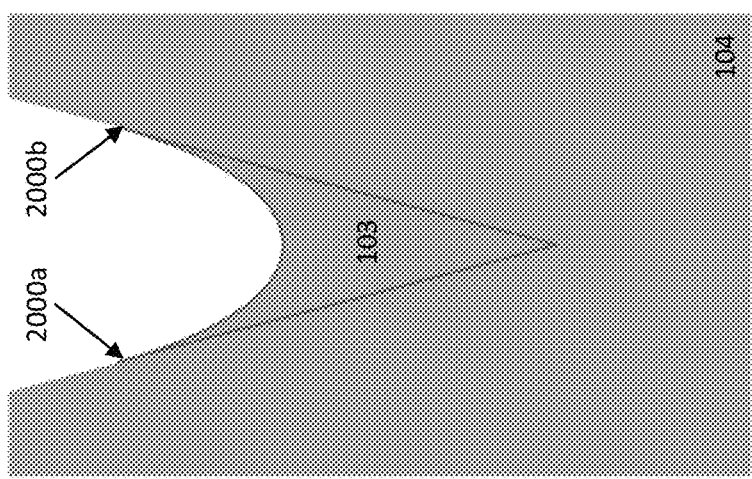
*FIG. 20*

FIG. 22
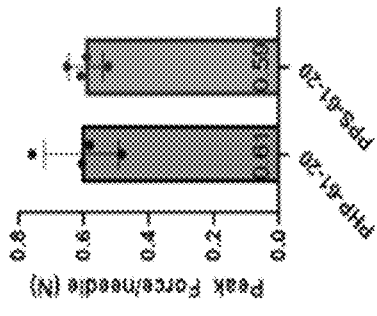
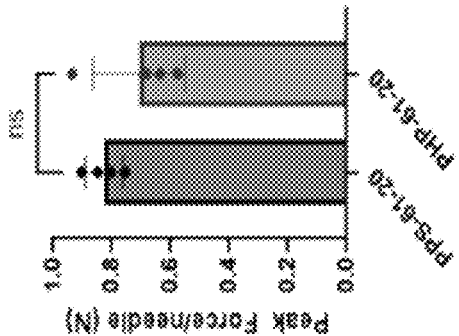
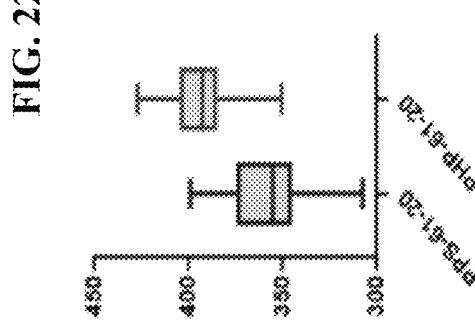
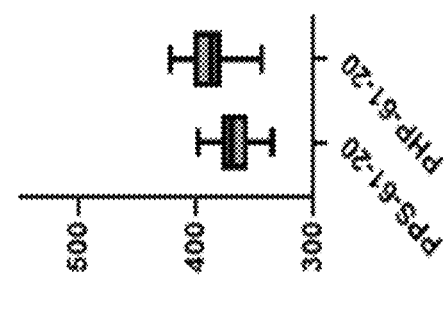

FIG. 24

Compiled PD-IVR Results

90 Needles

60 Needles

Rectangular sub-arrays

Filled needles are indicated by an X, all other mold cavities are left empty

41 Needles

61 Needles

Circular sub-arrays

Filled needles are indicated by an X, all other mold cavities are left empty

FIG. 25C
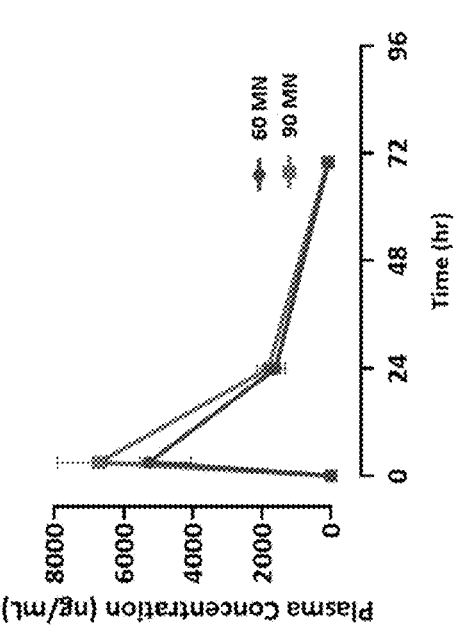
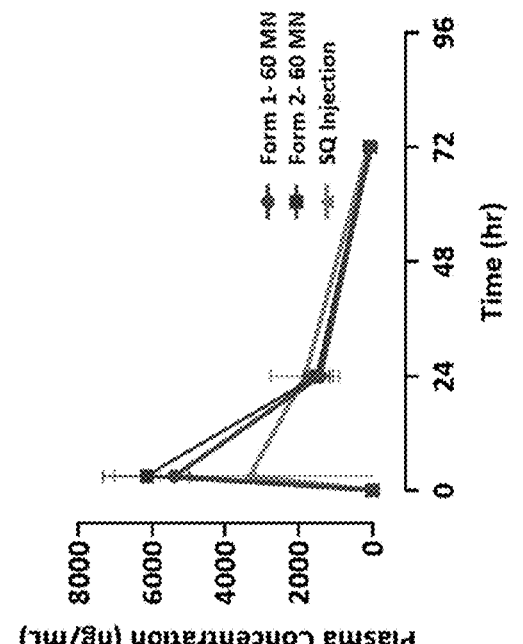
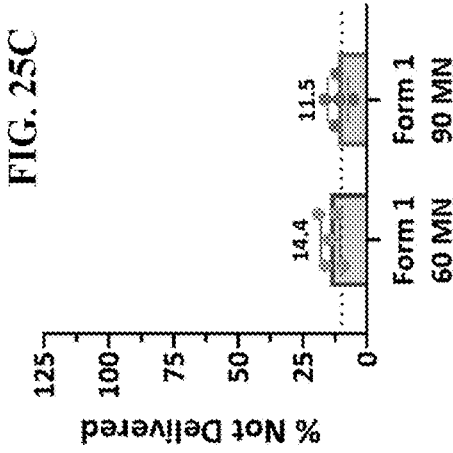
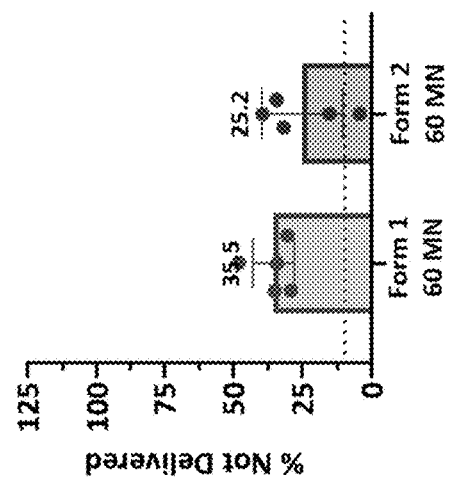
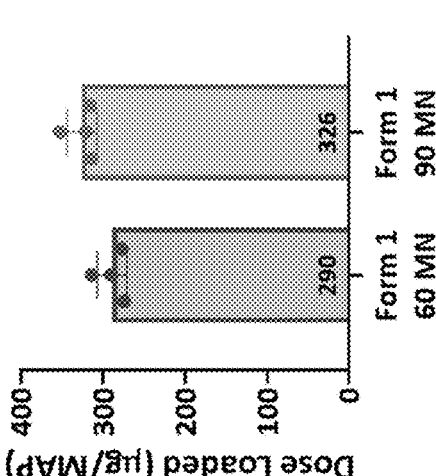
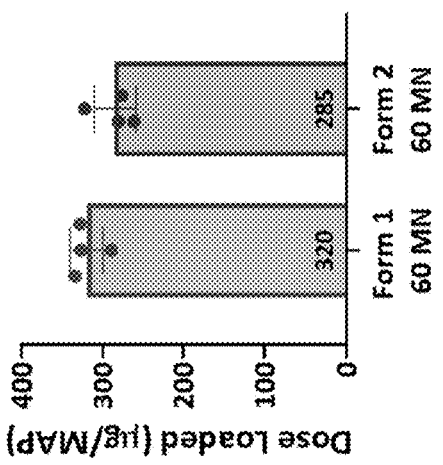

FIG. 27

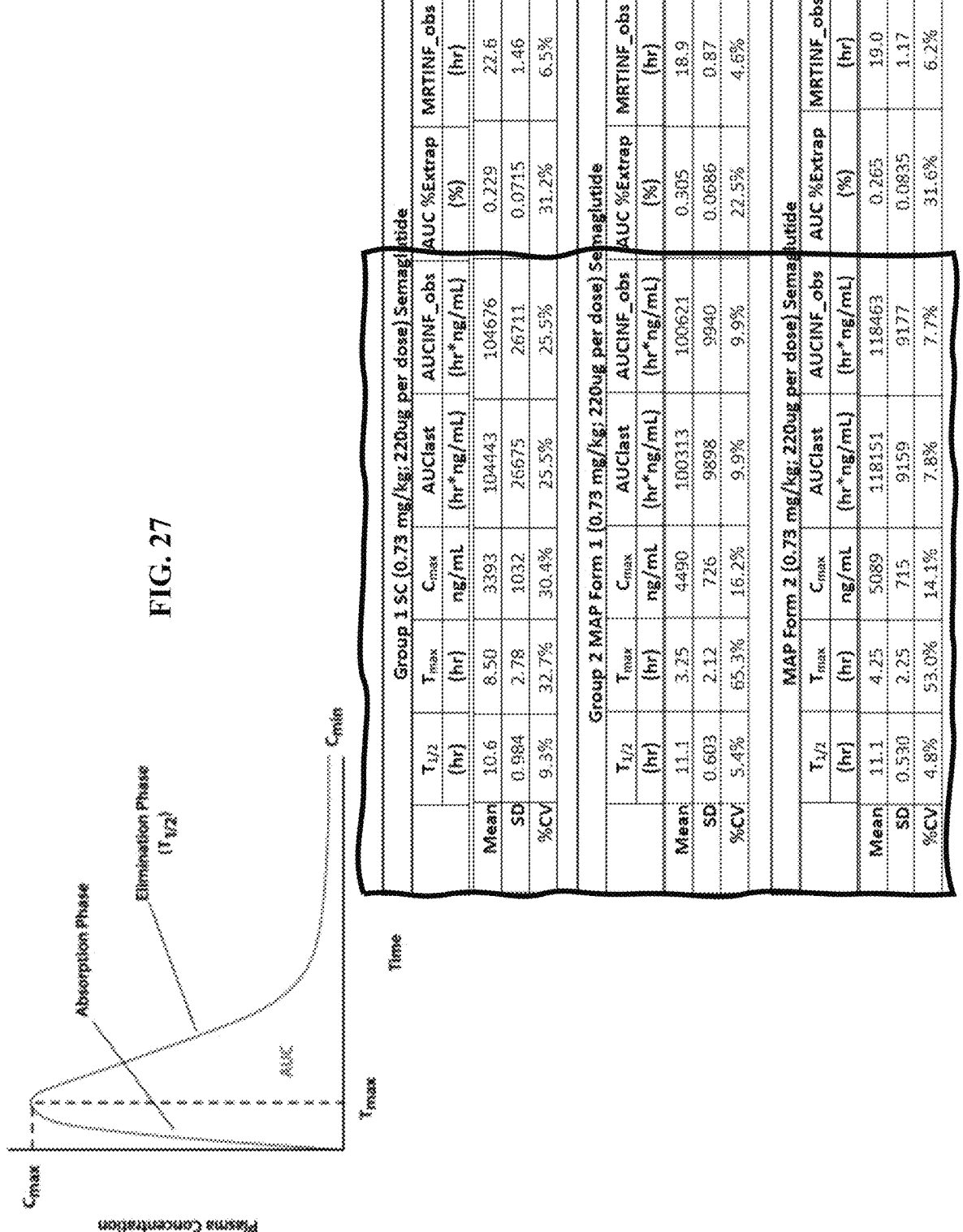

Group 1 SC (0.73 mg/kg; 220ug per dose) Semaglutide

| | T$_{1/2}$ (hr) | T$_{max}$ (hr) | C$_{max}$ ng/mL | AUClast (hr*ng/mL) | AUCINF_obs (hr*ng/mL) | AUC %Extrap (%) | MRTINF_obs (hr) |
|---|---|---|---|---|---|---|---|
| Mean | 10.6 | 8.50 | 3393 | 104443 | 104676 | 0.229 | 22.6 |
| SD | 0.984 | 2.78 | 1032 | 26675 | 26711 | 0.0715 | 1.46 |
| %CV | 9.3% | 32.7% | 30.4% | 25.5% | 25.5% | 31.2% | 6.5% |

Group 2 MAP Form 1 (0.73 mg/kg; 220ug per dose) Semaglutide

| | T$_{1/2}$ (hr) | T$_{max}$ (hr) | C$_{max}$ ng/mL | AUClast (hr*ng/mL) | AUCINF_obs (hr*ng/mL) | AUC %Extrap (%) | MRTINF_obs (hr) |
|---|---|---|---|---|---|---|---|
| Mean | 11.1 | 3.75 | 4490 | 100313 | 100621 | 0.305 | 18.9 |
| SD | 0.603 | 2.12 | 726 | 9898 | 9940 | 0.0686 | 0.87 |
| %CV | 5.4% | 65.3% | 16.2% | 9.9% | 9.9% | 22.5% | 4.6% |

MAP Form 2 (0.73 mg/kg; 220ug per dose) Semaglutide

| | T$_{1/2}$ (hr) | T$_{max}$ (hr) | C$_{max}$ ng/mL | AUClast (hr*ng/mL) | AUCINF_obs (hr*ng/mL) | AUC %Extrap (%) | MRTINF_obs (hr) |
|---|---|---|---|---|---|---|---|
| Mean | 11.1 | 4.25 | 5089 | 118151 | 118463 | 0.265 | 19.0 |
| SD | 0.530 | 2.25 | 715 | 9159 | 9177 | 0.0935 | 1.17 |
| %CV | 4.8% | 53.0% | 14.1% | 7.8% | 7.7% | 31.6% | 6.2% |

FIG. 28
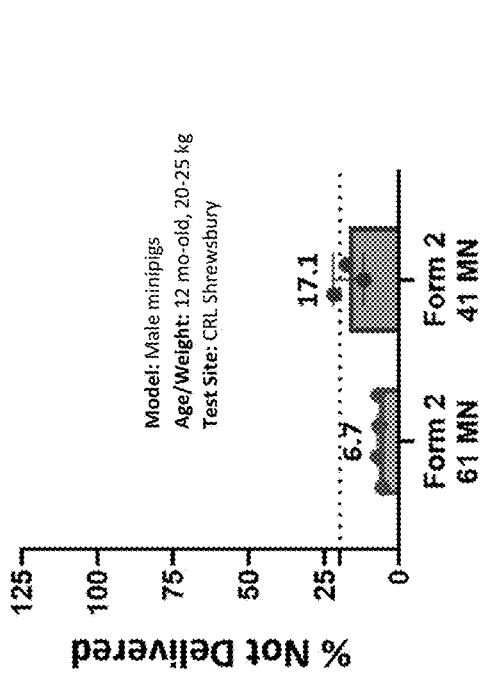
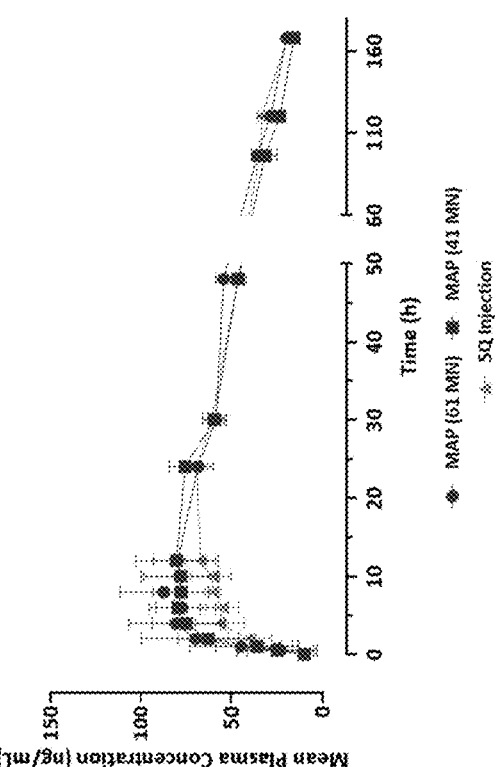
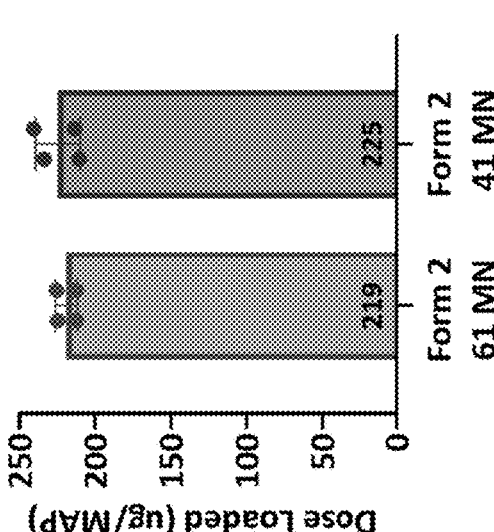
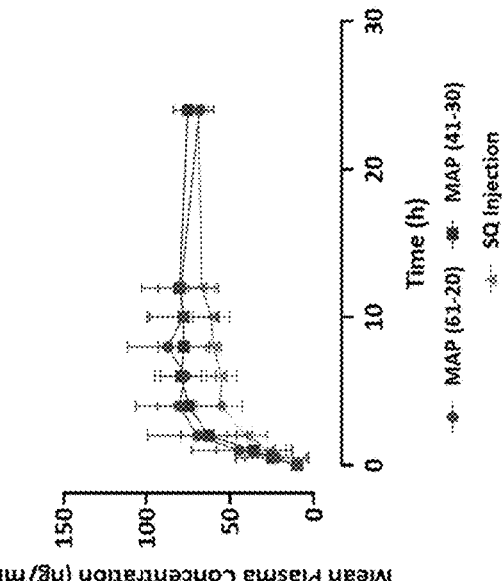

APPLICATOR AND MICRONEEDLE ARRAY PATCH DELIVERY SYSTEM

CROSS-REFERENCE TO RELATED APPLICATIONS

This application claims priority to U.S. Provisional Application No. 63/683,233, filed Aug. 14, 2024; U.S. Provisional Application No. 63/712,367, filed Oct. 25, 2024; and is a continuation in part of International Application No. PCT/US2024/34901, filed Jun. 21, 2024, which claims priority to U.S. Provisional Application No. 63/522,931, filed Jun. 23, 2023, all of which are herein incorporated by reference in their entireties. This application is related to U.S. patent application Ser. No. 19/002,468, filed Dec. 26, 2024 and International Application No. PCT/US2024/062002, filed Dec. 26, 2024 both of which are herein incorporated by reference in their entireties.

BACKGROUND OF THE DISCLOSURE

While certain types of microneedle configurations exist for delivering substances (e.g., vaccines, medications, etc.) to subjects, they are unable to effectively and consistently deliver active pharmaceutical ingredients (APIs) in appropriate amounts and to appropriate depths. Many configurations experience one or more of 1) inconsistent applications of microneedles to the skin of subjects due to uneven and inconsistent applications of force; and 2) suboptimal amounts of API being delivered to the subject. These trends are undesirable and it would be desirable to consistently and repeatedly deliver sufficient amounts of an API to a subject at a proper delivery depth.

BRIEF DESCRIPTION OF THE FIGURES

FIG. 18 is a flowchart for a manufacturing process according to some embodiments of the present disclosure.

FIG. 19 is another flowchart for a manufacturing process according to some embodiments of the present disclosure.

FIG. 20 is a visualization of tip morphology according to some embodiments of the present disclosure.

FIGS. 22-28 illustrate results of various empirical studies for the embodiments disclosed herein.

Figure 1A:
FIG. 1A is a perspective view of a medicament patch applied to a patient's arm.

The drawings are not necessarily to scale, or inclusive of all elements of a system, emphasis instead generally being placed upon illustrating the concepts, structures, and techniques sought to be protected herein.

SUMMARY

According to one aspect of the present disclosure, a microarray patch (MAP) and applicator system can include a microarray patch (MAP) and an applicator. The MAP can include a backing and a plurality of microneedles extending from the backing, each of the plurality of microneedles. Each of the plurality of microneedles can include a tip comprising an active pharmaceutical ingredient (API); and a water-soluble base configured to at least partially dissolve upon contact with a bodily fluid of a subject causing the tip to be released below a skin surface of the subject. The applicator can maintain the MAP; in response to an activation mechanism being activated, release a piston downward into the MAP; and push, via the piston, the MAP downward onto the skin surface of the subject such that the plurality of microneedles penetrate the skin surface and are delivered to the subject. Apexes of the plurality of microneedles are delivered to the subject at a depth of at least about 300 μm below the skin surface of the subject and whereby at least about 70% of the API is delivered to the subject after release of the tip of at least a portion of the plurality of microneedles.

In some embodiments, the piston can include a dome-shaped face that impacts and pushes the MAP downward. In some embodiments, the applicator is configured to maintain the MAP in a MAP holder. In some embodiments, the MAP holder is configured to, as the piston is released and prior to the piston contacting the MAP, release the MAP. In some embodiments, the MAP holder maintains the MAP via a plurality of flex arms, each configured to flex outward to release the MAP. In some embodiments, the plurality of flex arms flex outward to release the MAP as the piston contacts the MAP.

In some embodiments, each tip of the plurality of microneedles can include at least one of a tip sharpness of about a 0.01 mm radius or less; a tip strength of at least about 0.4 N; or a tip stiffness of at least about 200 N/mm. In some embodiments, the applicator is configured to push the piston with an impact energy of about 0.3 mJ to 5 mJ per microneedle. In some embodiments, the tip of each of the plurality of microneedles has a length of about 450 μm or less. In some embodiments, the activation mechanism is configured to be activated with a force of about 12 lbF.

According to another aspect of the present disclosure, a method of delivery an active pharmaceutical ingredient (API) can include maintaining a microarray patch (MAP) in an applicator. The MAP can include a backing and a plurality of microneedles extending from the backing. Each of the plurality of microneedles can include a tip comprising the API; and a water-soluble base configured to at least partially dissolve upon contact with a bodily fluid of a subject causing the tip to be released below a skin surface of the subject. The method can also include placing the applicator onto the skin surface of the subject; activating an activation mechanism of the applicator; releasing, via the applicator, a piston downward into the MAP; pushing, via the piston, the MAP downward onto the skin surface of the subject such that the plurality of microneedles penetrate the skin surface; causing the water-soluble base of each of the plurality of microneedles to dissolve within the skin of the subject; and delivering the tip of each of the plurality of microneedles to the subject such that apexes of the plurality of microneedles reach a depth of at least about 300 μm below the skin surface of the subject, wherein at least 70% of the API is delivered to the subject.

In some embodiments, pushing the MAP downward comprises pushing the MAP downward via a dome-shaped face of the piston. In some embodiments, the method can include maintaining the MAP in a MAP holder prior to releasing the piston. In some embodiments, the method can include releasing, via the MAP holder, the MAP as the piston is released and prior to the piston contacting the MAP. In some embodiments, the method can include maintaining, via the MAP holder, the MAP via a plurality of flex arms, each configured to flex outward to release the MAP. In some embodiments, the method can include flexing the plurality of flex arms outward to release the MAP as the piston contacts the MAP.

In some embodiments, each tip of the plurality of microneedles can include at least one of a tip sharpness of about a 0.01 mm radius or less; a tip strength of at least about 0.4 N; or a tip stiffness of at least about 200 N/mm. In some embodiments, the applicator is configured to push the piston with an impact energy of about 0.3 mJ to 5 mJ per microneedle. In some embodiments, the tip of each of the plurality of microneedles has a length of about 450 μm or less. In some embodiments, the activation mechanism is configured to be activated with a force of about 12 lbF.

According to another aspect of the present disclosure, a method of manufacturing a microarray patch (MAP) can include dispensing a print solution into each microneedle cavity of an array of microneedle cavities formed within a microneedle mold, the print solution comprising an active pharmaceutical ingredient (API) and at least one excipient; drying the dispensed print solution in a first drying environment with a humidity of at least 50% to form an array of tips; dispensing a base solution into each microneedle on top of the dried print solution; drying the dispensed base solution in a second drying environment with a humidity of at least 50% to form an array of bases; applying an adhesive surface of a backing to an outer surface of the array of bases; and demolding the microneedle mold from the backing.

In some embodiments, applying a backing with an adhesive surface to an outer surface of the array of bases can include pressing the adhesive surface of the backing to the outer surface of the array of bases with a force of about 60 psig. In some embodiments, dispensing the print solution into each microneedle cavity of the array of microneedle cavities can include dispensing a volume of about 10-40 nL. In some embodiments, dispensing the base solution into each microneedle cavity of the array of microneedle cavities can include dispensing a volume of about 70-110 nL. In some embodiments, dispensing the print solution into each microneedle cavity of the array of microneedle cavities can include dispensing the print solution via machine vision guided printing.

In some embodiments, dispensing the print solution into each microneedle cavity of the array of microneedle cavities can include dispensing a first volume of the print solution into each microneedle cavity of the array of microneedle cavities; drying the dispensed first volume of the print solution in the first drying environment with a humidity of at least 50%; and dispensing a second volume of the print solution into each microneedle cavity of the array of microneedle cavities on top of the dried first volume of the print solution.

In some embodiments, dispensing the base solution into each microneedle cavity of the array of microneedle cavities can include dispensing a first volume of the base solution into each microneedle cavity of the array of microneedle cavities; drying the dispensed first volume of the base solution in the first drying environment with a humidity of at least 50%; and dispensing a second volume of the base solution into each microneedle cavity of the array of microneedle cavities on top of the dried first volume of the base solution.

According to another aspect of the present disclosure, a microarray patch (MAP) and applicator system can include a microarray patch (MAP) and an applicator. The MAP can include a backing and a plurality of microneedles extending from the backing. Each of the plurality of microneedles can include a tip comprising an active pharmaceutical ingredient (API), wherein the API is a glucagon-like peptide-1 (GLP-1) agonist; and a water-soluble base configured to at least partially dissolve upon contact with a bodily fluid of a subject causing the tip to be released below a skin surface of the subject. The applicator can be configured to maintain the MAP; in response to an activation mechanism being activated, release a piston downward into the MAP; and push, via the piston, the MAP downward onto the skin surface of the subject such that the plurality of microneedles penetrate the skin surface and are delivered to the subject. Apexes of the plurality of microneedles are delivered to the subject at a depth of at least about 600 µm below the skin surface of the subject and whereby at least about 70% of the API is delivered to the subject after release of the tip of at least a portion of the plurality of microneedles.

DESCRIPTION

The following detailed description is merely exemplary in nature and is not intended to limit the claimed invention or the applications of its use.

The present disclosure relates generally to applicator devices and systems for medicament patches. The devices and systems can be used to reliably apply patches to a patient's skin. It is also important to note that, while the term "patient" is generally used throughout this disclosure, the disclosed systems and methods can also apply to "subjects."

There are currently numerous devices available or being developed for delivery of medications (e.g., pharmaceuticals, an influenza vaccine and/or a coronavirus vaccine, e.g., an mRNA-based vaccine) to patients through the skin. The simplest of these devices can include systems that release or apply substances to the skin for absorption. More complicated systems can facilitate delivery by various techniques such as use of small needles to facilitate delivery deeper within the skin, or other systems, such as iontophoresis to encourage movement of materials into the skin.

Recently, patch-types devices have been developed that allow placement of biodegradable needle-like devices within the skin. These devices may carry substances to be delivered and degrade slowly over time, thereby exposing the body to the delivered substance over a desired time period, potentially along with other agents that protect the substance to be delivered or provide other therapeutic benefits (e.g., control release rate, improve biologic function). Such devices can be used for delivery of vaccines, small molecule drugs, biologics, combination products, or other therapeutic or prophylactic substances. The effectiveness of such biodegradable needle-like patches can be improved by ensuring that the patches are applied reliably with sufficient force to deposit the biodegradable needles at a desired depth within the skin. However, although such patches may be effectively applied by simple manual application by a patient or health care provider, it would be beneficial to provide improved systems to reliably apply the biodegradable patches with little or minimal training and with a high level of repeatability.

Accordingly, the present disclosure provides improved devices for application of medical patches, including biodegradable needle patches.

The present disclosure relates to applicator devices for applying patch-type devices to a patient's skin. The devices can allow reliable application of a patch, including even and reliable application such that a sufficient force and/or depth of skin penetration is achieved to ensure that needle-like portions of the patch are positioned at a desired depth within or beneath a portion of the skin. The applicator can be configured to provide a predetermined force to quickly and reliably apply the patch to a desired location, thereby helping to improve delivery of active agents (e.g., drugs, vaccines, biologics, or other materials) using the selected patch.

In some embodiments, the applicator may include a top portion having a top surface and a sidewall, wherein the top portion includes an activation mechanism; a bottom portion having a bottom surface and a sidewall; a middle portion connected to the top portion and the bottom portion; a piston portion connected to the top portion and the middle portion; and a compressible member positioned between the middle portion and the piston portion and configured to apply downward pressure to the piston portion, wherein when the activation mechanism is activated, the piston portion is released from the top portion and the middle portion and moves towards the bottom surface; wherein a medicament patch is held in a patch holder near the bottom surface of the bottom portion, and when the piston portion moves downwards, the medicament patch is released from the patch holder and pushed downward by the piston portion through the patch holder onto a patient's skin.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purposes.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

As noted above, various patch devices are available for delivery of medications or other substances into or through the skin. As used herein, "medicament" or "medicament patch" will be understood to refer to any substance or patch carrying a substance to provide a biologic effect to a patient. "Medicaments" will be understood to refer to any pharmaceutical, small molecule drug, vaccine (including any vaccine such as an mRNA vaccine, protein, glycoprotein, live viral, live attenuated viral, inactivated viral, recombinant, or other vaccine) peptide, biologic, antibody, vitamin, mineral, hormone, or other materials that can be delivered into or through the skin.

Medicament patches can include microneedle-based devices, which are described in more detail below. Such microneedle devices can include one or more (and preferably a group or an array) of microneedles. The microneedles are located on a skin-facing surface of a flexible or semi-rigid patch, and by application of the patch to a patient's skin, the needles can penetrate the skin to a desired depth. In some cases, the microneedles may include a biodegradable component that is deposited at a desired distance into the skin and may degrade at a desired rate to release or present the medicament to a patient, thereby eliciting a desired response, such as an immunologic response to a vaccine. More details regarding exemplary patches, including microneedle patches are described further below.

In order to improve the efficacy of any medicament patch, it is desirable to ensure that the patch is applied appropriately, including even application to ensure that as many microneedles as possible are positioned at an appropriate depth. Furthermore, it is desirable to ensure that the patch is applied such that the microneedles are pushed into the skin at a desired depth without inadvertent shearing of microneedles above the skin. Proper application of the patch can improve overall efficacy.

In order to improve consistency and effectiveness of patch application, an automated applicator device may be desirable. Accordingly, the present disclosure provides embodiments of an applicator device having one or more features or advantages over existing devices or simple manual application. The disclosed devices may be configured for repeated or single use, and the devices may be pre-loaded with a patch (i.e., as a kit or patch product including applicator and patch). Alternatively, the applicator may be separate from a patch, and a patch may be selected and loaded to the device (e.g., based on desired medicaments, patient characteristics, or need for additional applications for more than one patient or for a patient that needs more than one patch).

The applicator can improve patch application by one or more of (1) properly holding and/or stretching/pre-tensioning skin to receive the patch, (2) applying a reliable degree of force and/or depth of force against the skin to ensure proper microneedle placement, and/or (3) controlling distribution of application force across the patch. The structure and function of the applicator in its various embodiments is described in more detail below.

FIG. 1A is a perspective view of a medicament patch 100 applied to a patient's arm. As shown, the patch 100 is substantially square, or square with rounded corners, but other shapes and configurations are contemplated and described below. The patch will generally have an adhesive to secure the patch to a patient's skin. At least the backing layer will be semi-flexible and capable of being deployed using the applicator(s) described herein.

Figure 1B:
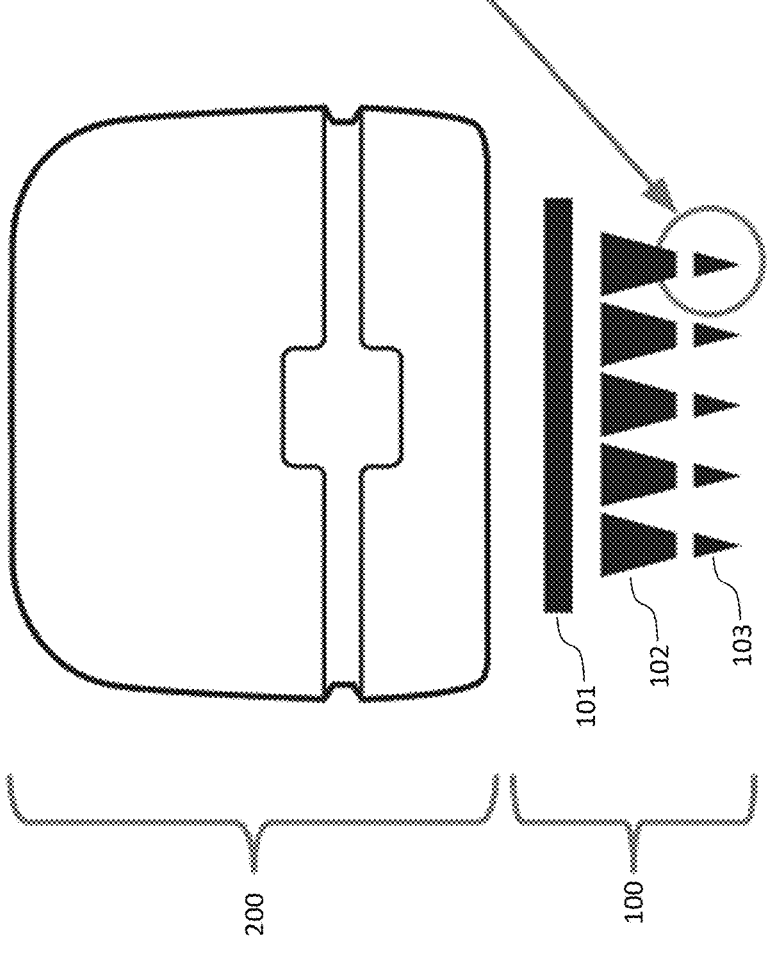
FIG. 1B is an exploded view of an applicator and microneedle array patch delivery system according to some embodiments of the present disclosure.

FIG. 1B is an exploded view of an applicator and microneedle array patch delivery system 1000 according to some embodiments of the present disclosure. The system 1000 can include a microarray patch (MAP) 100 and an applicator 200. The MAP 100 can include a backing 101 with a plurality of microneedles, each including a base 102 and a tip 103. In some embodiments, the tips 103 can be modified to deliver various different vaccine or therapeutic payloads. Benefits of the system 1000 can include improved tolerability, improved efficacy through sustained release, shelf-stability, and injection-free self-administration. The components of the system 1000 (i.e., the applicator 200 and MAP 100) can function together to safely and consistently deliver doses to a subject.

Figure 1C:
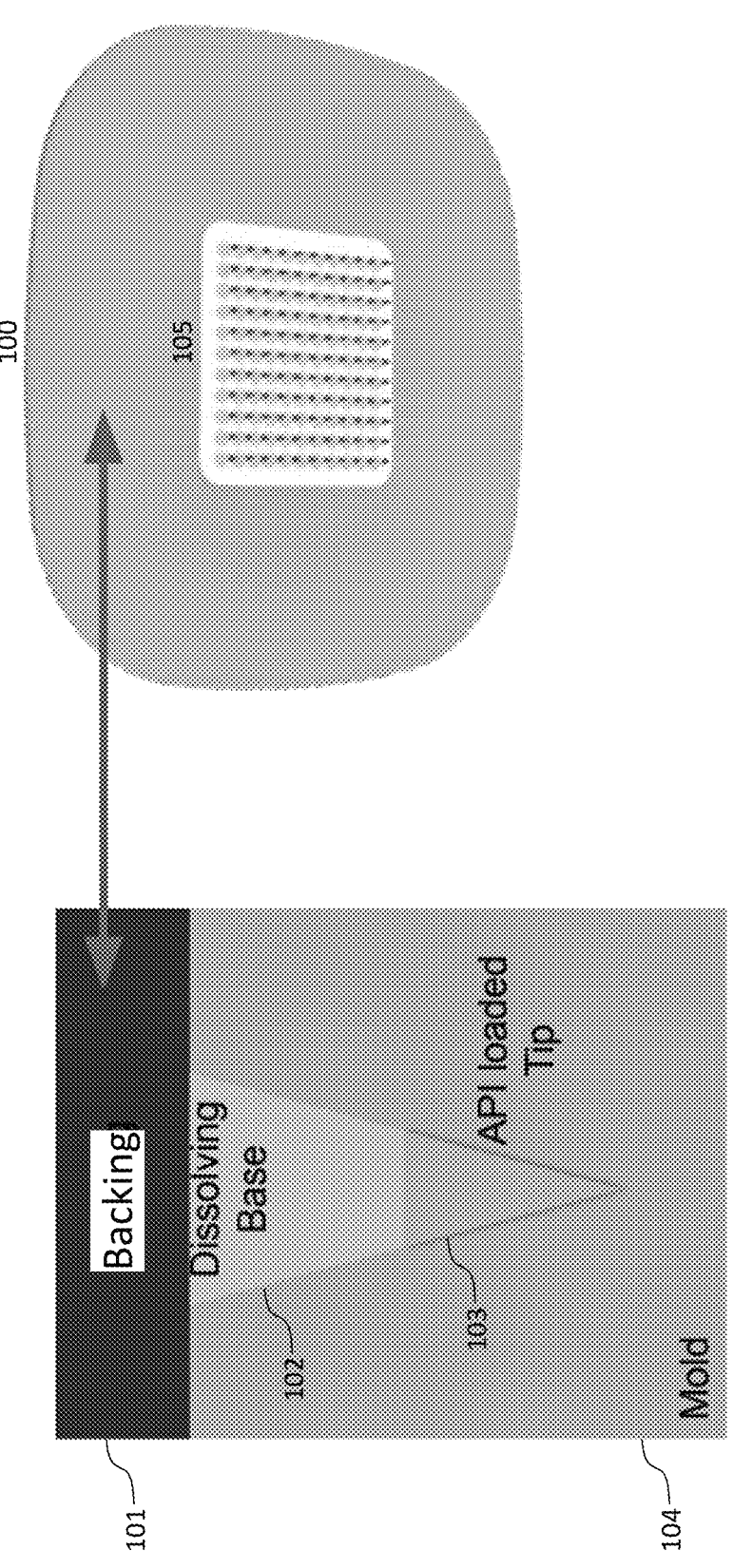
FIG. 1C shows a microneedle array patch according to some embodiments of the present disclosure.

FIG. 1C shows a microneedle array patch according to some embodiments of the present disclosure. On the left of FIG. 1C is a zoomed-in view during manufacturing of a single microneedle of the MAP 100 that includes a portion of the backing 101, a base 102, and a tip 103 within a mold 104. The tip 103 can be loaded with an active pharmaceutical ingredient (API), while the base 102 can be dissolvable.

Figures 1D, 1E:
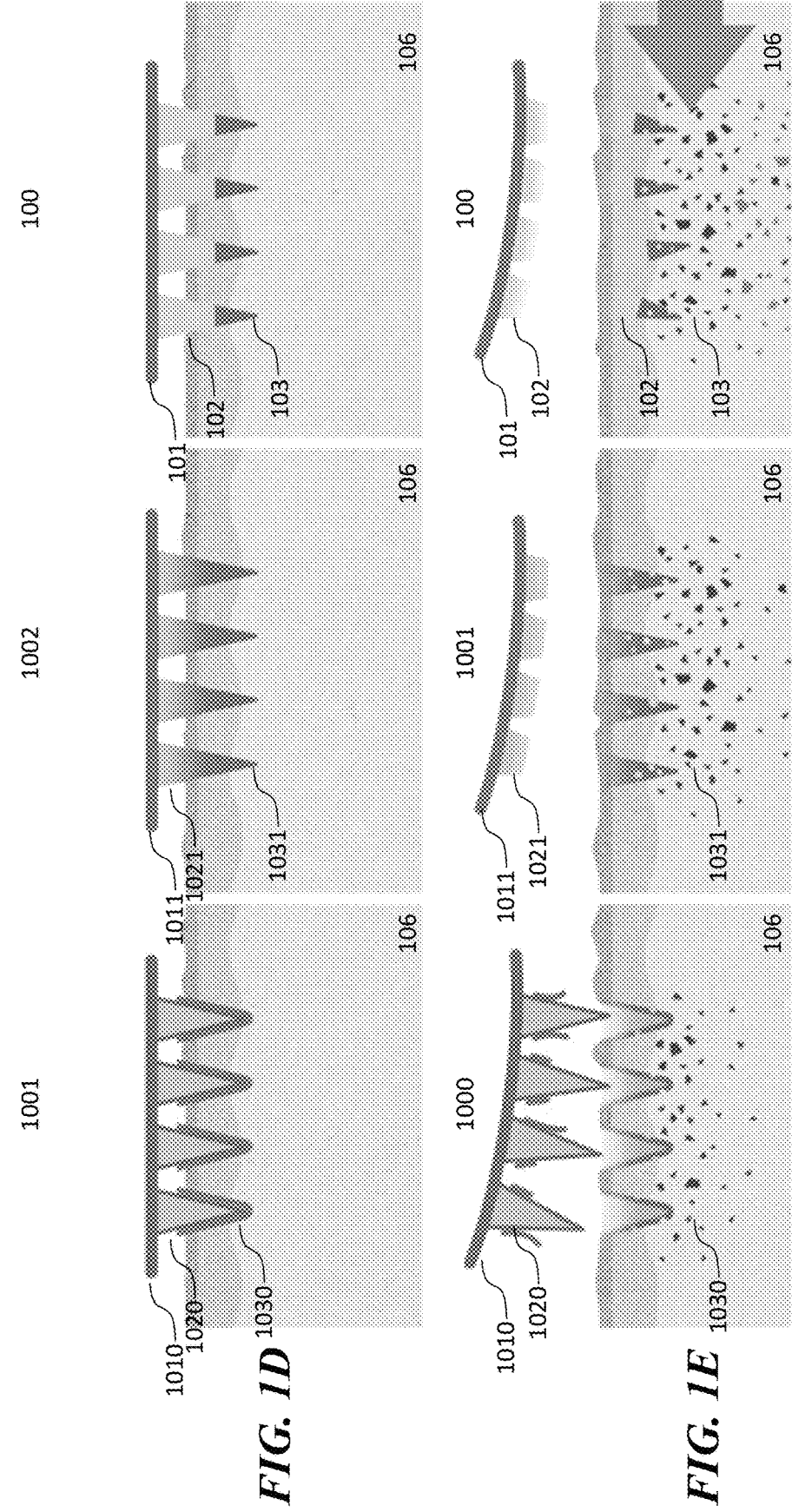
FIG. 1D shows various microneedle configurations inserted into a subject's skin.
FIG. 1E illustrates the deployment of various microneedle configurations into a subject's skin.

Additional details with respect to the dissolvability of the base 102 and deployment of the tips 103 are discussed in relation to FIGS. 1D and 1E. Once the backing 101, base 102, and tip 103 are removed from the mold 104, they form the array 105 that is part of the MAP 100, as shown on the right-hand side of the figure. In some embodiments, the backing 101 can serve as a mechanical carrier for the various microneedles. Moreover, the backing 101 can include a skin-compatible adhesive to protect the MAP 100 and keep the MAP 100 in place during wear time.

FIG. 1D shows various microneedle configurations inserted into a subject's skin. Microneedle configurations 1001 (left-hand side) and 1002 (middle) are existing systems that perform sub optimally compared to the systems of the present disclosure. Configuration 1001 utilizes a backing 1010, a base 1020, and a coating 1030. The API is incorporated into the coating 1030, which is only coated on as an outer layer of the needle. However, because the API extends around so much of the needle, there is a low efficiency (in terms of API delivery) to the subject 106 (see FIG. 1E). This is undesirable, inefficient, and sometimes ineffective. Configuration 1002 utilizes a backing 1011, a base 1021, and ends 1031. However, the API of configuration 1002 is spread throughout both the base 1021 and the end 2031 and typically utilizes a shearing force or dissolution of the entire needle to deliver the API. This leads to inconsistent dosing, which is also undesirable, inefficient, and sometimes ineffective (see FIG. 1E). The disclosed MAP configuration 100 (right-hand side of the figure) has improved tip deployment depth, efficiency, and consistency in dosing. The base 102 is a specifically dissolvable and separate layer from the tip 103. After the MAP 100 is inserted into the subject 106, the base 102 dissolves because of the contact with the fluids underneath the subject's skin and breaks apart. This allows the tip 103 to be, in most cases, completely deployed such that very high amounts of the API are delivered to the subject 106. This is therefore an improvement in both efficiency and consistency in dosing.

Figure 1F:
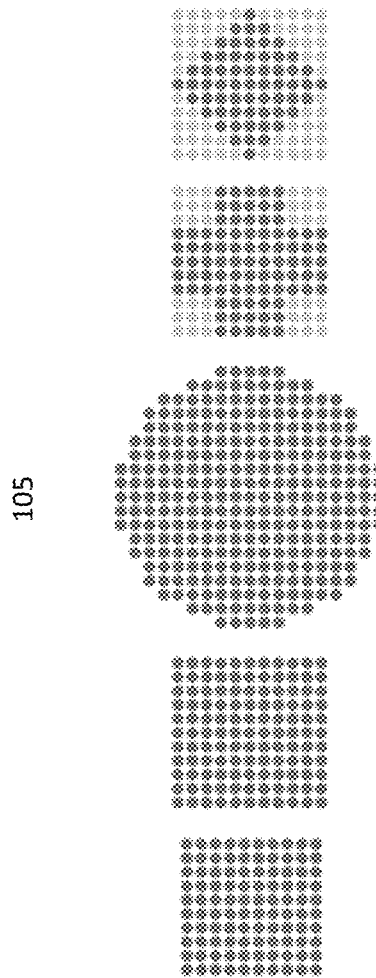
FIG. 1F shows various array configurations according to some embodiments of the present disclosure.

FIG. 1F shows various array configurations of arrays 105 according to some embodiments of the present disclosure. The disclosed manufacturing techniques (see FIGS. 16-21) allow for greater flexibility in terms of controlling dose delivery because it accommodates a broader range of payloads and dose requirements. Such array size flexibility can facilitate the development of formulations that support consistent dose delivery. For example, the disclosed manufacturing techniques can utilize different print formulations to dictate the array size and maintain a desired application energy per needle using the applicator 200. Print solutions with defined parameters (e.g., viscosity for printability) can ensure the length of the tip 103 and the overall morphology of the needle can preserve MAP function (e.g., tip deployment and dose delivery). In addition, the disclosed flexible, programmable dispensing capabilities can allow for the manufacturing of full arrays, subarrays, or arrays of different layouts all using the same mold 104. The ability to easily vary array size provides an additional dimension for establishing a formulation that meets desired parameters for printing, deploying, and dissolution.

Figure 1G:
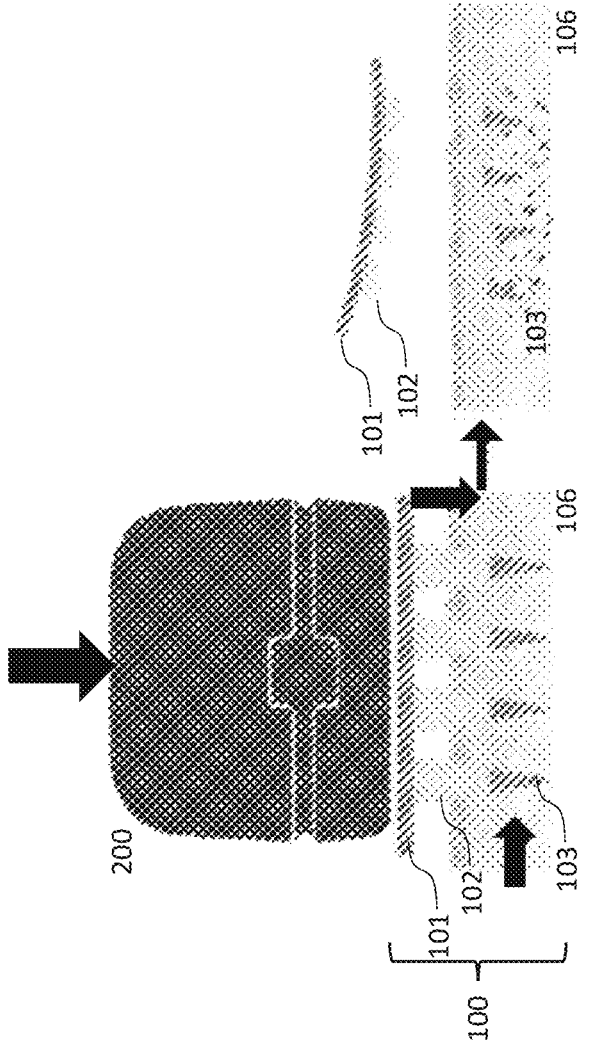
FIG. 1G shows another view of an applicator and microneedle array patch delivery system according to some embodiments of the present disclosure.

FIG. 1G shows another view of an applicator and microneedle array patch delivery system 1000 according to some embodiments of the present disclosure. As a downward force is applied to the applicator 200, an activation mechanism is activated which causes the MAP 100 to be pushed onto the skin of a subject 106. Additional details with respect to the applicator 200 are discussed in relation to FIGS. 2A-15. The tips 103 and at least a portion of the base 102 are pushed into the skin of the subject 106, and as the base 102 dissolves upon contact with a bodily fluid of the subject, the tips 103 are released and deployed such that the API is delivered. In some embodiments, at least 70% of the API can be delivered to the subject 106 at a depth of about 300 μm below the skin surface. In some embodiments, such delivery can include an apex (i.e., the point) of each of the plurality of microneedles being delivered to at least about 300 μm below the skin surface. In some embodiments, at least 8 0% of the API can be delivered to the subject 106. In some embodiments, at least 90% of the API can be delivered to the subject 106. In some embodiments, delivery can include an apex (i.e., the point) of each of the plurality of microneedles being delivered to at least about 400 μm below the skin surface. In other embodiments, delivery can include an apex (i.e., the point) of each of the plurality of microneedles being delivered to at least about 500 μm below the skin surface. In some embodiments, delivery can include an apex (i.e., the point) of each of the plurality of microneedles being delivered to at least about 600 μm below the skin surface. Moreover, the percentage of API delivered can be measured by identifying the residual amounts of API remaining on the MAP once it has been removed from the subject. This percentage can be consistent with the Post Deployment In Vitro Release parameter consistent with the embodiments described herein.

Specifically, the disclosed system 1000 and the various exemplary embodiments discussed herein can be used to deliver pharmaceuticals, vaccines (e.g., an influenza vaccine a coronavirus vaccine, or an mRNA-based vaccine, etc.), antigens, and other APIs discussed herein. In particular embodiments, the system 1000 as discussed herein can be used to deliver pharmaceuticals such as glucagon-like peptide-1 (GLP-1). Specific exemplary formulation and empirical data related to the delivery of GLP-1 is discussed in the "Exemplary Data Demonstrating Benefits of the System" section of this application. Moreover, other types of APIs can also be delivered via the disclosed system, details of which are discussed in concurrently filed (i.e., filed on Dec. 26, 2024) applications titled "An Applicator for a Microneedle Array Patch Delivery System" and "MICRONEEDLE ARRAY PATCHES (MAPS), SYSTEMS, AND METHODS FOR MANUFACTURING AND USING SAME," both of which are herein incorporated by reference in their entireties.

Figures 2A, 2B, 2C, 2D:
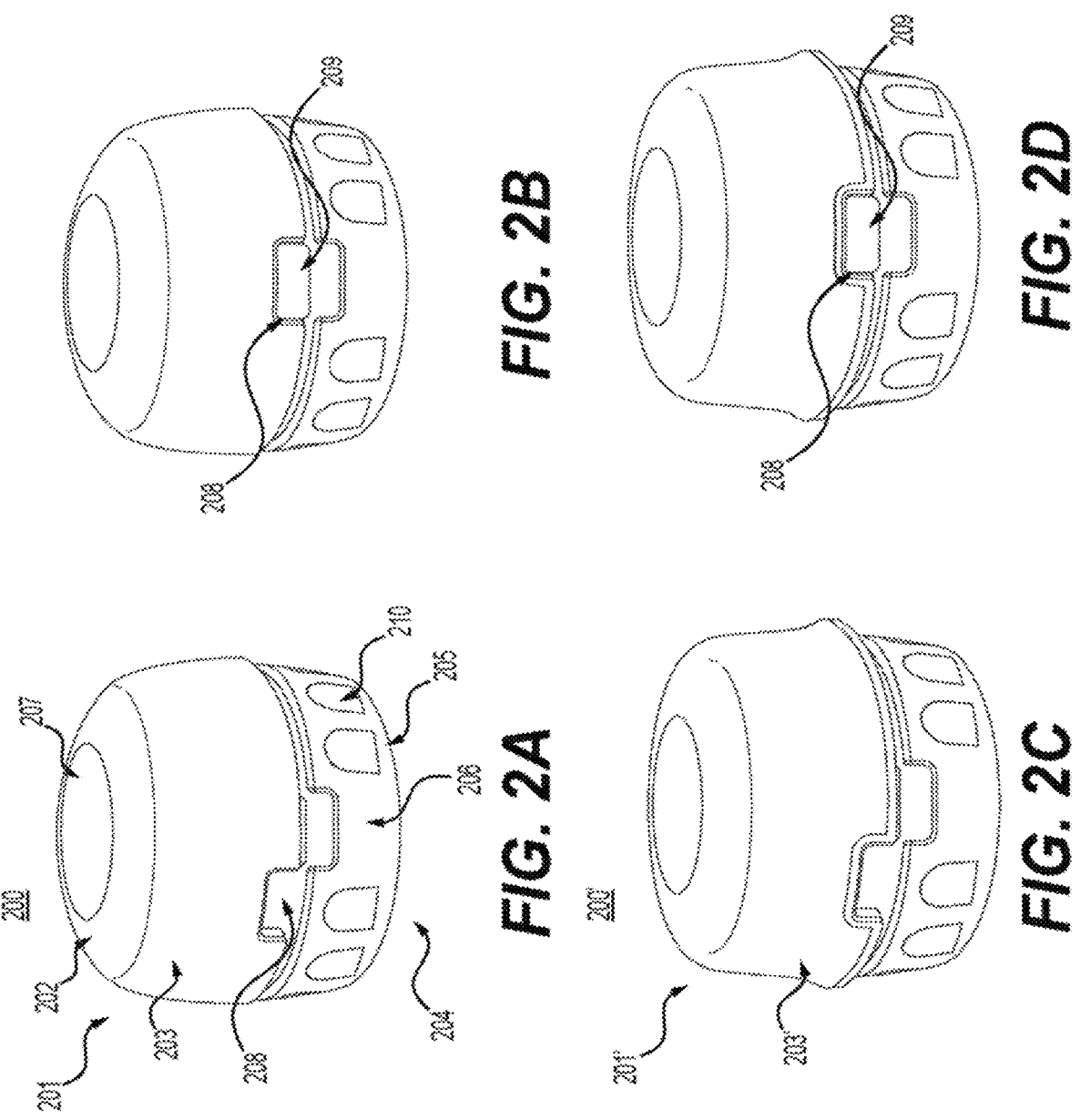
FIGS. 2A-2D are side perspective views respectively of two exemplary applicator devices for use with a medicament patch like that illustrated in FIG. 1.

FIGS. 2A-2D are side perspective views respectively of two exemplary applicator systems for use with a medicament patch 100 like that illustrated in FIG. 1. As shown in FIG. 2A, the applicator 200 has a top portion 201 and a bottom portion 204. In one embodiment, the top portion 201 has a top surface 202 and a sidewall 203, and the bottom portion 204 has a bottom surface 205 and a sidewall 206. In some embodiments, the top surface 202 may include an activation mechanism to activate the applicator and the release of the patch. The activation mechanism can be any mechanism that is suitable for the purpose of activating the applicator by causing release of a plunger to apply a medicament patch to a patient's skin. In one example, the top portion is the activation mechanism. In this example, a user can press the top portion to activate the applicator 200. In another example, the top surface 202 of the top portion includes a button, e.g., button 207 as shown, as the activation mechanism. In this example, a user can press the button to activate the applicator. In another example, the top portion may include a switch and a user can press the switch to activate the applicator. In some embodiments, the sidewall 203 includes one or more open portions 208. In one embodiment, as shown, a logo or a sticker is attached on the outer surface of top surface 202. The sidewall 206 of the bottom portion 204 may include one or more indentations 210. The indentations may be configured to encourage a patient to properly grip the device during an unlocking step.

In one embodiment, the core portion of the applicator 200 or the bottom portion may include one or more indicators. In the example depicted in FIG. 2A, the core portion, e.g., middle portion, described in more detail below includes one or more indicators 209. In one embodiment, the top portion 201 can be twisted by a user so that the one or more open portions 208 are aligned with the one or more indicators 209. In one example, the applicator 200 may make a click sound when the one or more open portions 208 are aligned with the one or more indicators 209. In one embodiment, the applicator 200 is in a locked state when the one or more open portions 208 not aligned with the one or more indicators 209, as shown in FIG. 2A. In this example, the activation mechanism of the applicator 200 may be in locked state and cannot be pressed to activate the applicator. In another example, the applicator 200 is in unlocked state when the one or more open portions 208 aligned with the one or more indicators 209, as shown in FIG. 2B. In this example, the activation mechanism of the applicator may be in unlocked state and can be pressed to activate the applicator.

Figure 15:
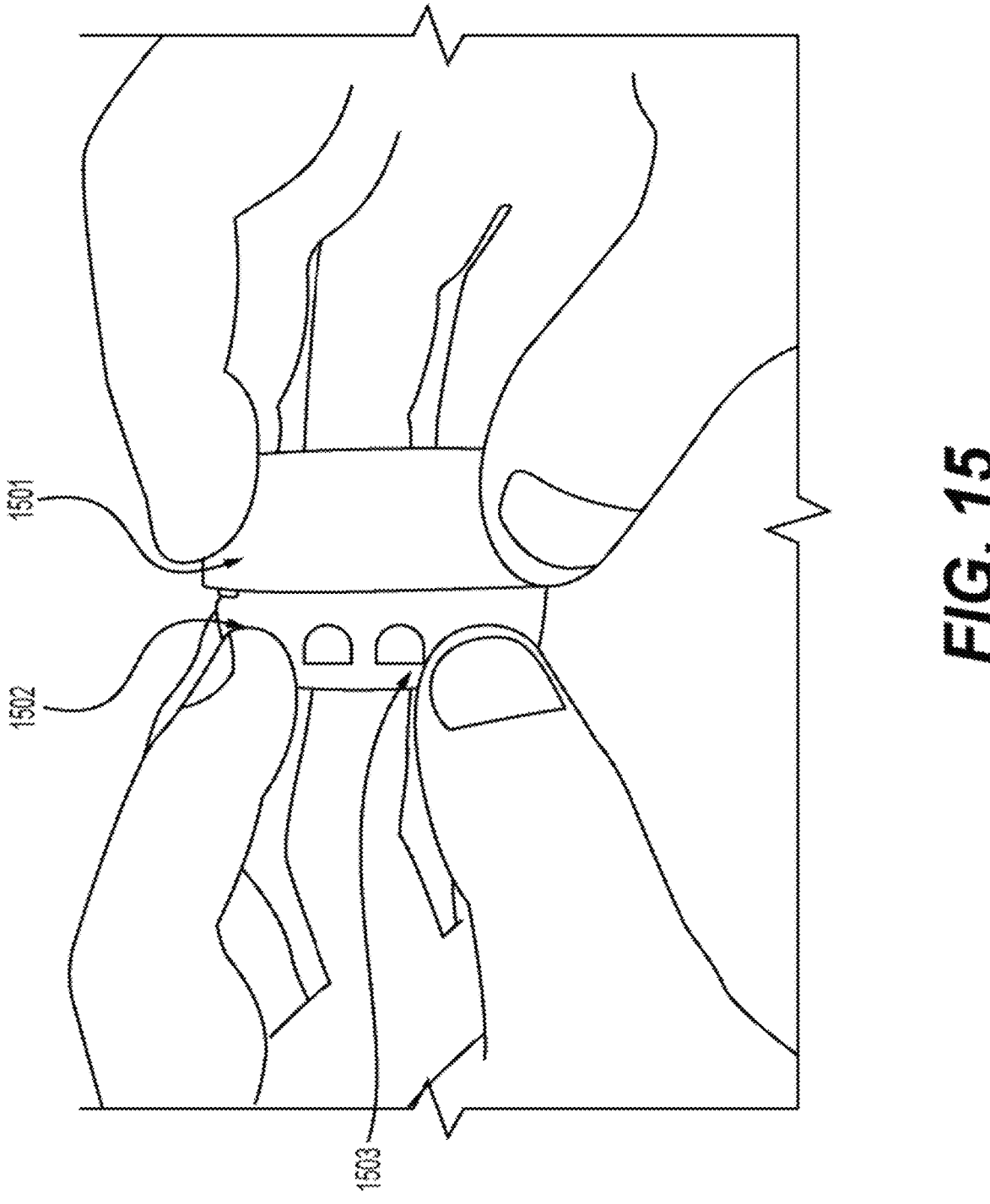
FIG. 15 is an image showing a user holding an applicator device.

When in use, a user can hold the sidewall 203 of the top portion 201 and the bottom surface 205 can be pressed against a patient's skin. The top portion can be any shape and size for easy grip (as illustrated in FIG. 15). In one example, as shown in FIGS. 2A and 2B, the sidewall 203 of the top portion 201 is substantially cylindrical. In another example, as shown in FIGS. 2C and 2D, the sidewall 203' of the top portion 201' is substantially cylindrical with a flared bottom. The bottom surface 205 can be shaped substantially like a circle or other shape with an opening, and the pressure of the bottom surface and help dome the skin within the opening to aid in application of the medicament patch by tensioning the skin.

Figures 3A, 3B, 3C:
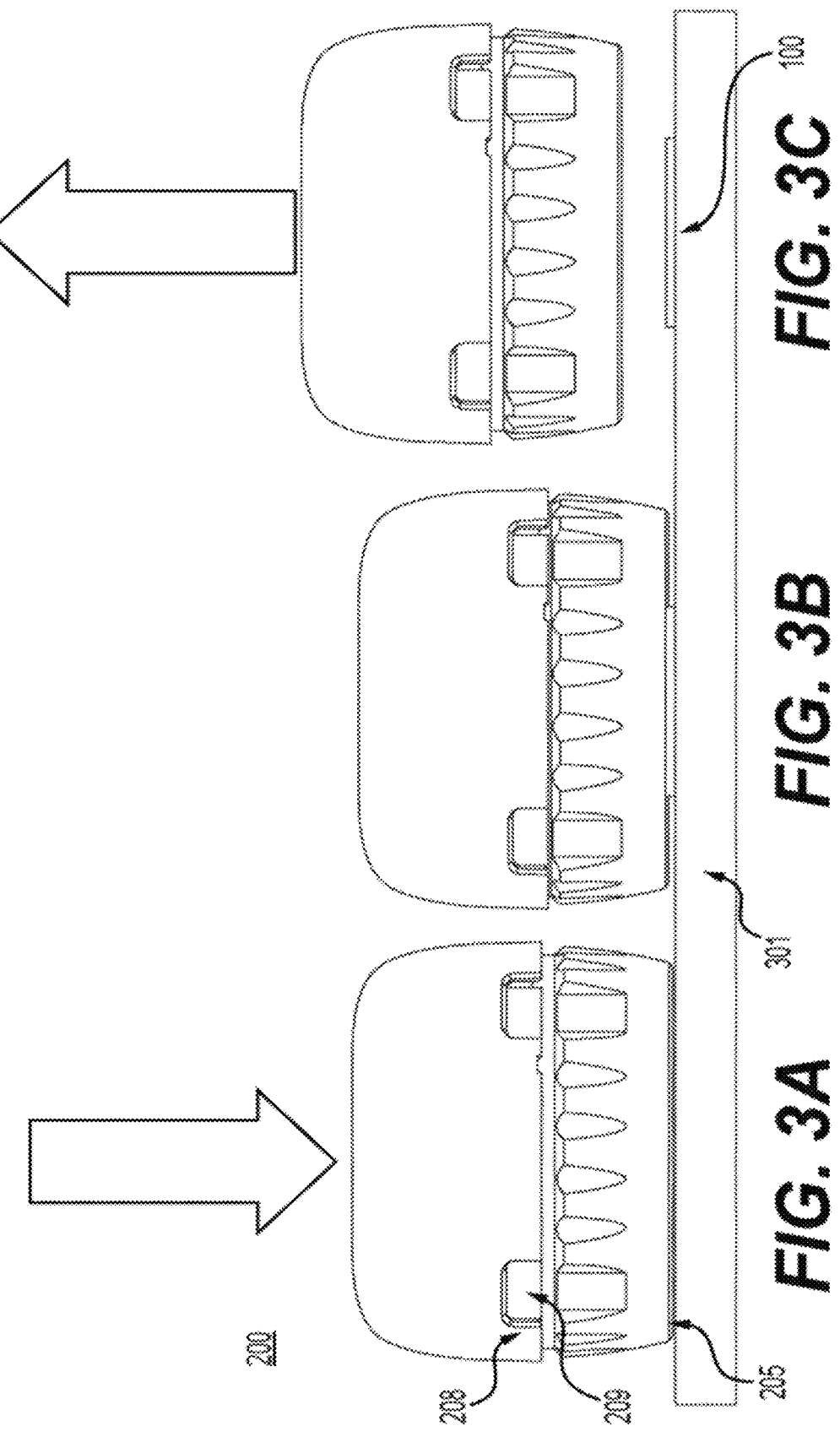
FIGS. 3A-3C are perspective views illustrating application of the medicament patch to a patient's skin by the applicator device, according to exemplary embodiments.

FIGS. 3A-3C illustrate the application of the medicament patch 100 to a patient's skin by the applicator 200, according to one exemplary embodiment. As shown in FIG. 3A, when one or more open portions 208 are aligned with the one or more indicators 209, the applicator 200 is pressed against the patient's skin 301 with the bottom surface in contact with the patient's skin 301. Next, a user activates the applicator using an activation mechanism. In one example, the user presses down the top portion to activate the applicator 200. In another example, the user presses down a button or a switch on the top portion to activate the applicator. After being activated, an internal piston portion is released and pushed downwards towards a patch holder holding the medicament patch 100 to release the patch from the applicator 200 (FIG. 3B). In some embodiments, the piston portion releases the medicament patch 100 from the patch holder, and then pushes onto the medicament patch to ensure sufficient pressure is applied so that the microneedles of the medicament patch can be positioned at an appropriate depth into the patient's skin 301. Next, as shown in FIG. 3C, after the medicament patch 100 is applied to the patient's skin, the applicator is removed. In some embodiments, a new medicament patch may be loaded in the applicator 200. An exemplary patch loading process is described in more detail below with respect to FIGS. 14A-14E.

Figure 4:
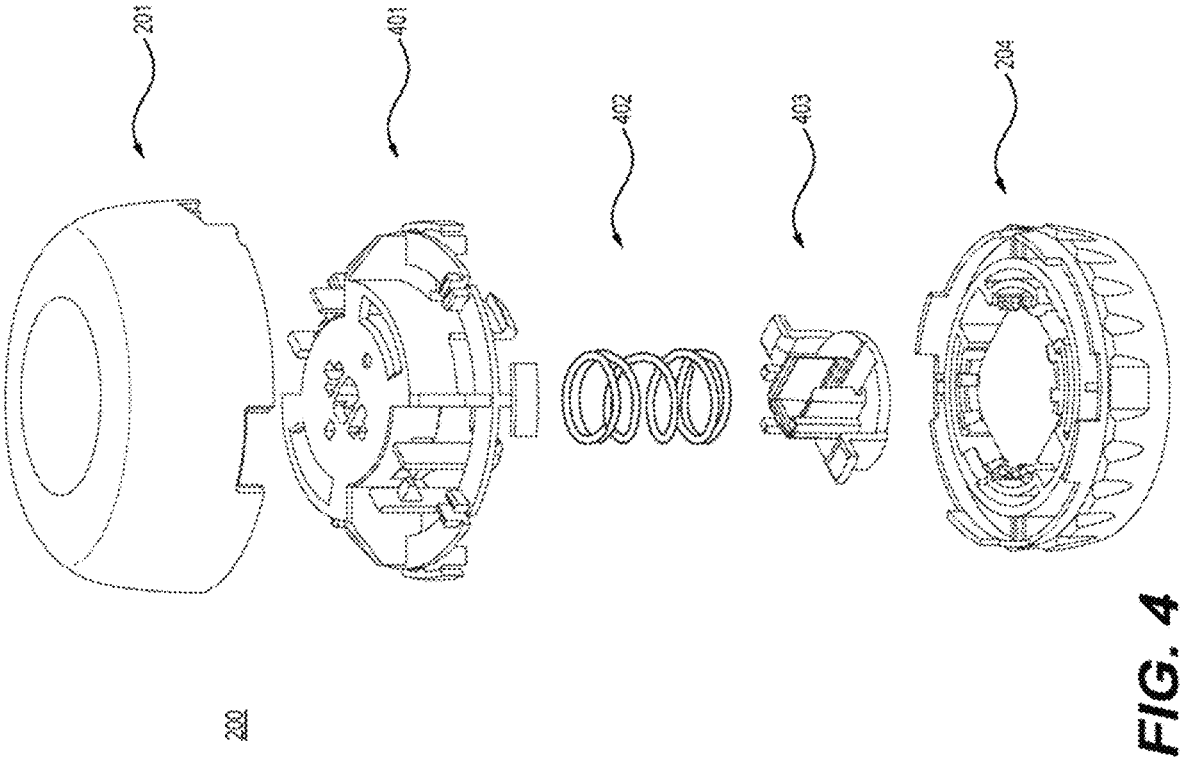
FIG. 4 is a perspective expanded view of the applicator device, according to exemplary embodiments.

FIG. 4 is an expanded view of the application device 200, according to various embodiments. As discussed with respect to FIGS. 2A-2D above, the applicator device 200 includes a top portion 201 and a bottom portion 204.

Furthermore, the applicator device 200 includes a middle portion 401 connected to the top portion 201 and the bottom portion 204 using a number of connection mechanisms. A piston portion 403 is connected to the top portion 201 and the middle portion 401 using a number of connection mechanisms. A compressible member 402 is positioned between the middle portion 401 and the piston portion 403 and configured to apply downward pressure to the piston portion 403. The compressible member 402 can be any suitable spring or other compressible structure. For example, the compressible member 402 may be a typical spring, compression spring, wave spring, dome spring, or leaf spring. Alternatively, a compressible member such as a balloon, compressible bladder, or a similar structure may be used.

Each component of applicator 200 is described in more detail in FIGS. 5A-10B below. The connection and configuration between the components of the applicator 200 is described in more detail in FIGS. 12A and 12B below.

Figures 5A, 5B:
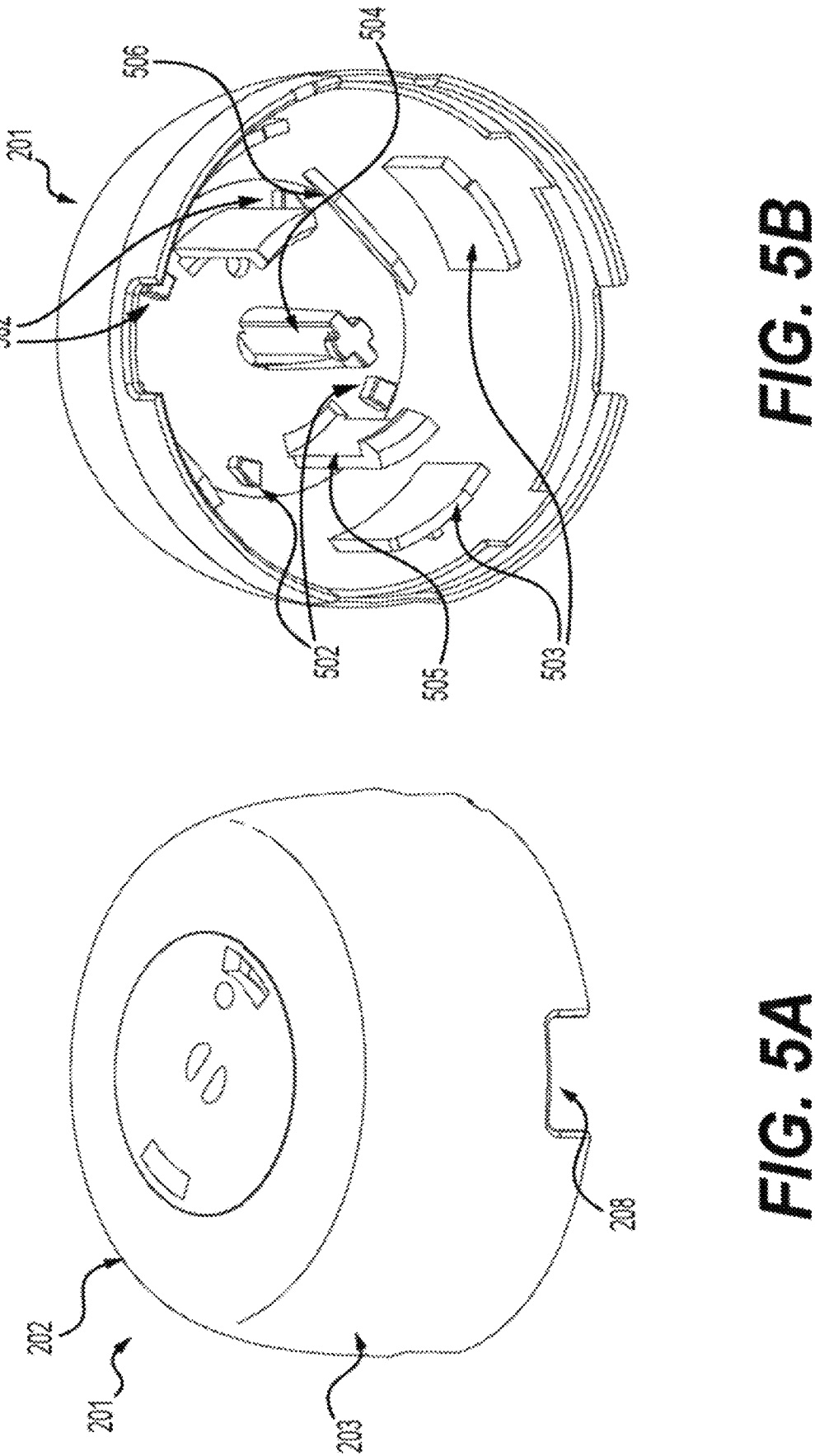
FIGS. 5A and 5B are top and bottom perspective views of a top portion, according to exemplary embodiments.

FIGS. 5A and 5B are top and bottom perspective views of an exemplary top portion 201. As shown in FIG. 5A, the top portion 201 includes a top surface 202 and a sidewall 203. In this example, a logo or a sticker can be attached to the top surface 202 (FIG. 2A-2D). As shown in FIG. 5B, the inside of the top portion 201 may include one or more vertical stops 502. As shown, the top portion 201 includes four vertical stops 502, but a number of stops can be used. In one embodiment, the one or more vertical stops 502 prevent the top portion 201 from being pressed downward to activate the plunger unless the open portions 208 are aligned with the one or more indicators 209. In particular, when the one or more open portions 208 are not aligned with the indicators 209, the stops 502 will press against the top surface of the top portion 201, thereby preventing the top portion from being pushed downward. But when the open portions 208 are aligned with the one or more indicators 209, the stops 502 will be aligned with openings 603 in the middle portion 401, such that the stops 502 can enter the openings to allow the top portion 201 to be pressed downward.

Furthermore, the top portion may include one or more first flexure interfaces 503. In one embodiment, the one or more first flexure interfaces 503 connect to the middle portion, preventing the top portion 201 from moving downwards. In one embodiment, the top portion includes one or more second flexure interfaces 506. In one example, when the device is activated, e.g., pressed down, the one or more second flexure interfaces 506 couple to the middle portion, preventing the top portion from moving upwards when the piston portion being pressed downwards. In one embodiment, top portion includes a middle beam 504 and one or more beams 505 each with a protrusion extending from the top surface.

Figure 6A:
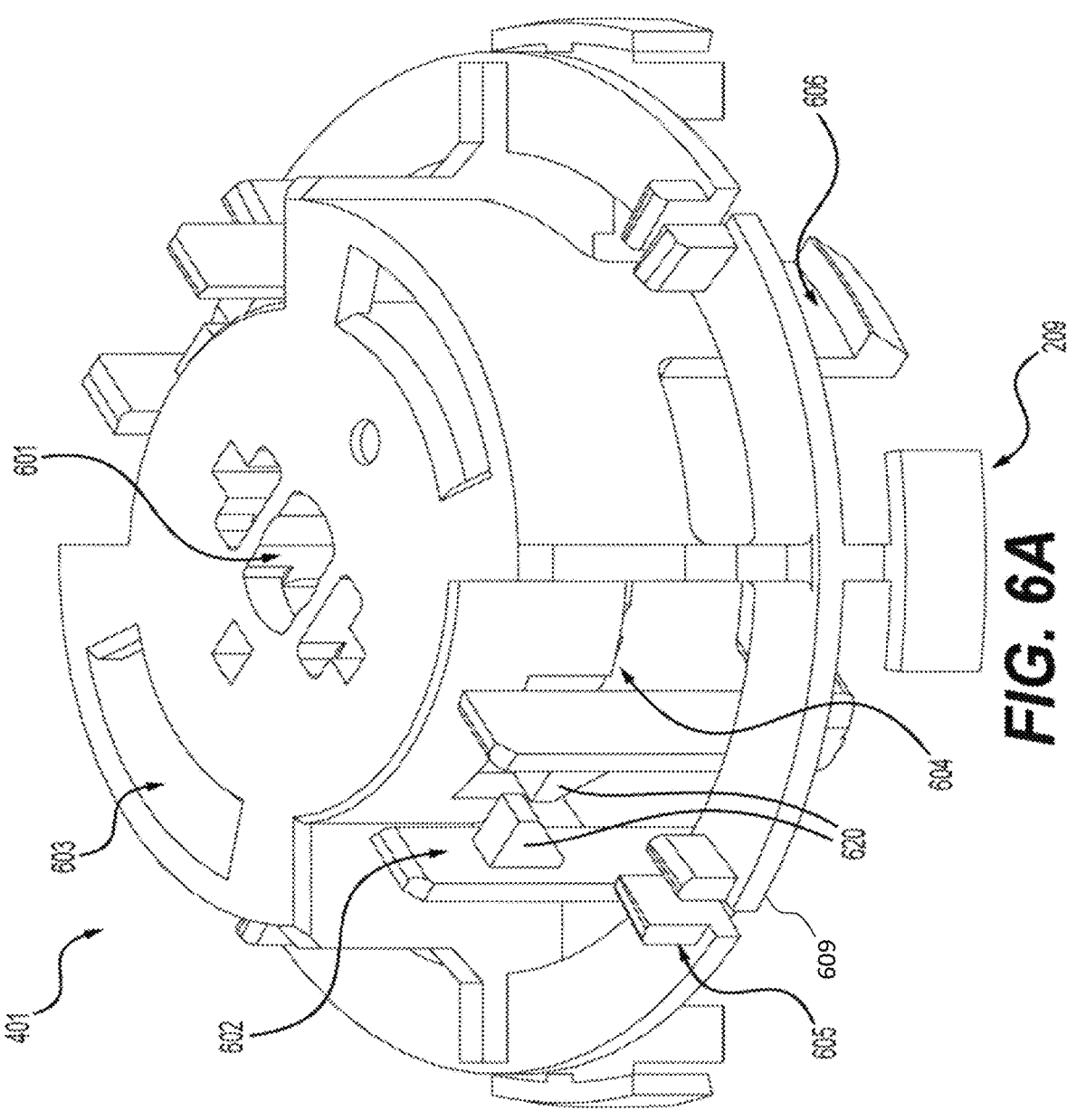
FIGS. 6A-6C are a top perspective view (6A), a side cut-away view (6B), and a bottom perspective view (6C) of a middle portion, according to exemplary embodiments.
Figure 6B:
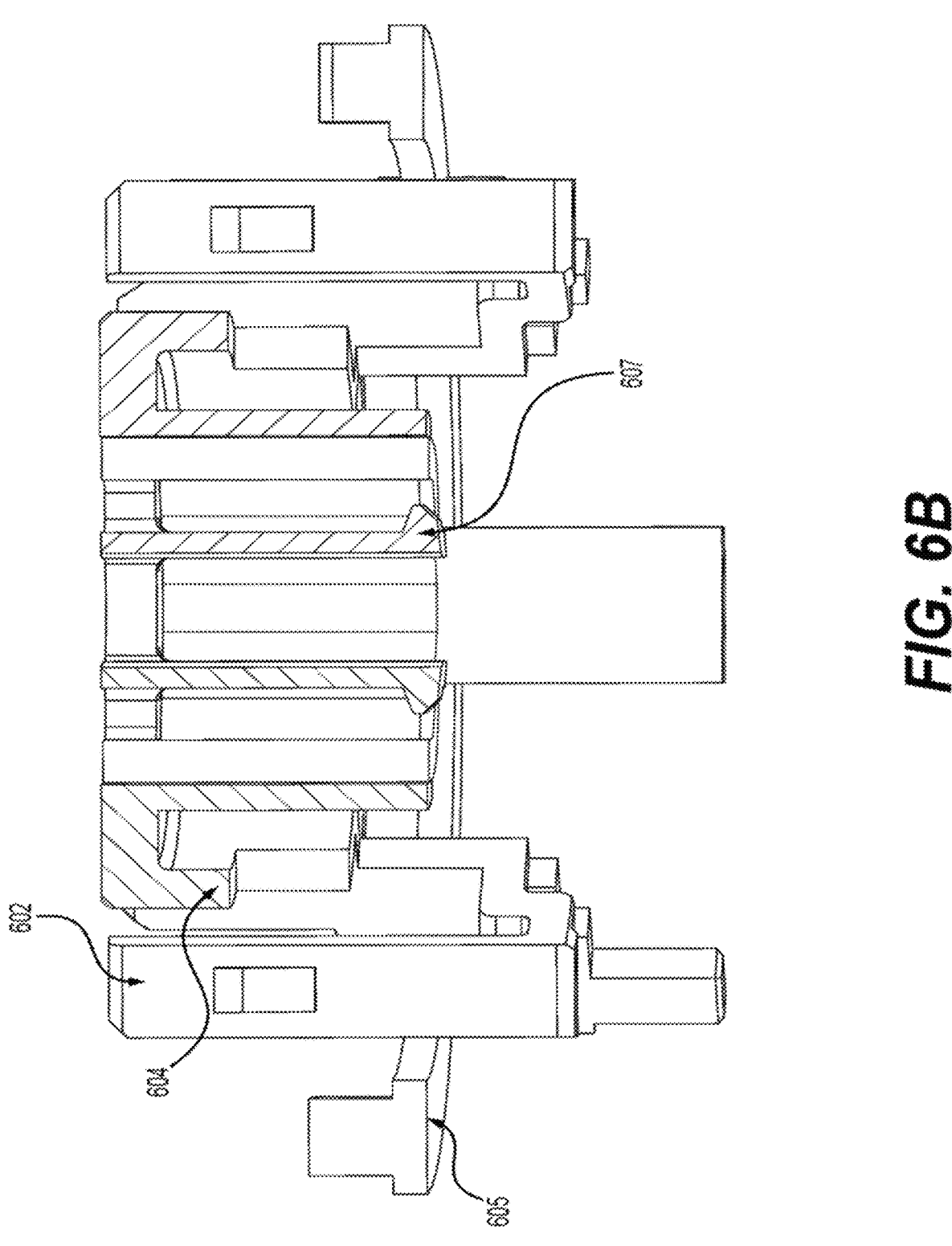
Figure 6C:
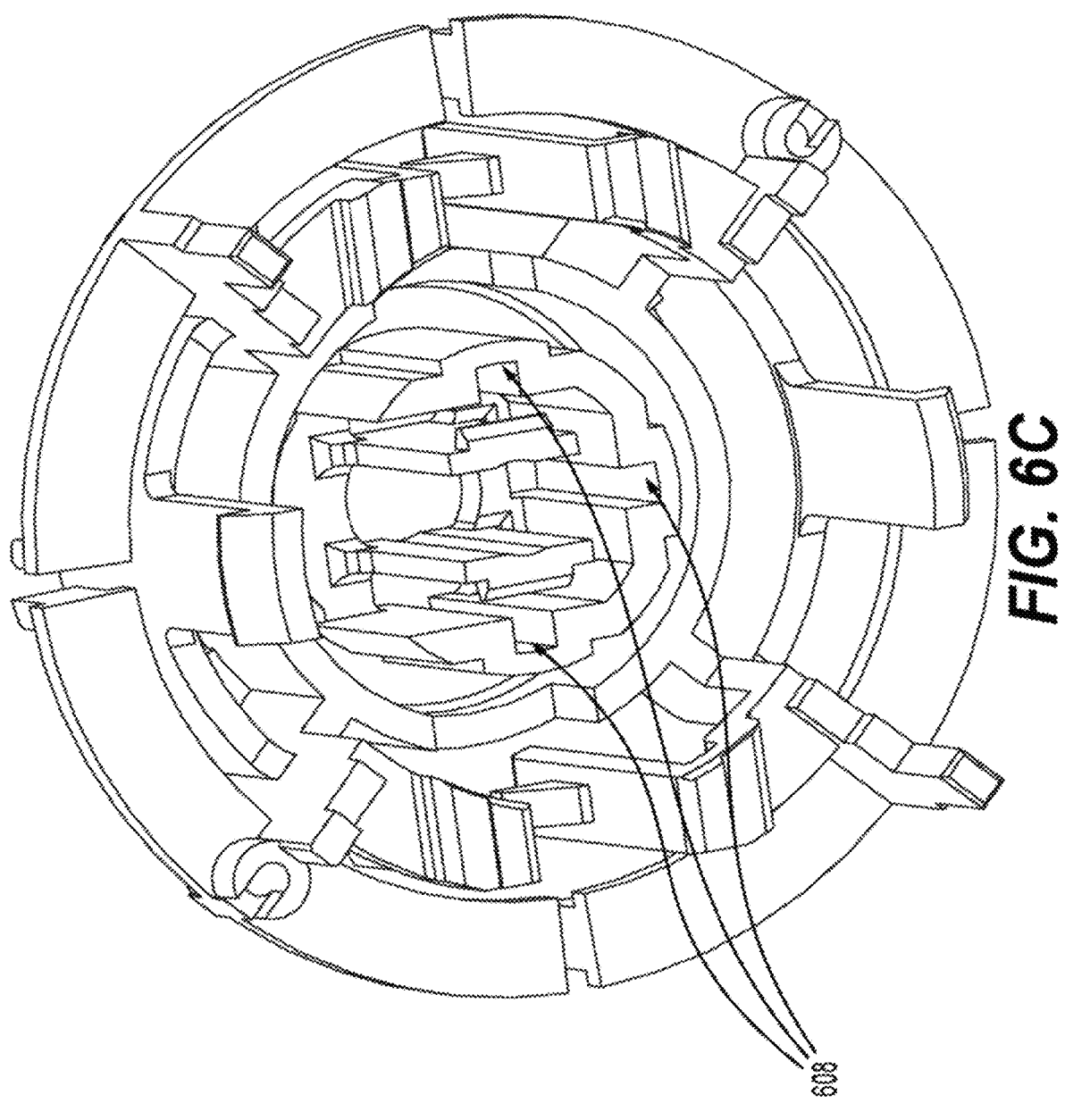

FIGS. 6A-6C are perspective views of a middle portion 401. As shown in FIG. 6A, the middle portion 401 includes one or more indicators 209. In addition, the middle portion 401 includes a center hole 601. In one embodiment, the middle beam 504 can pass through the center hole 601. In one embodiment, the protrusions of the one or more beams 505 of the top portion 201 connect to the edge 604 of the inner circle of the middle portion 401. In another embodiment, the middle portion 401 further includes one or more beams 602 each with a protrusion.

In addition, the middle portion 401 can include one or more flex arms 609. In some embodiments, the middle portion 401 can include eight flex arms 609. Each flex arm 609 can extend circumferentially around the middle portion 401. In some embodiments, the activation force of the activation mechanism (i.e., the force that initially activates the piston movement) can generally have two main contributors. First, an unlatching force can contribute, which comes from the force required to disengage the piston portion 403 from its retention features on the middle portion 401. In some embodiments, the unlatching force is about 2 lbs. second, a more significant contributor to the activation force can come from the one or more flex arms 609. The flex arms 609 can provide stiffness to the system that allows for a specific activation force to be repeatably achieved. In some previous iterations, the total activation force was about 10 lbs., where 8 lbs. of the force came from the flex arms 609, which had a thickness of about 1.22 mm. However, unexpectedly, it was discovered that increasing the activation force actually improved performance, tolerability, and comfort for the user. Increasing the activation force also improved skin tenting (the skin staying raised in a tent shape). In some embodiments, increasing the activation force to about 12 lbs., where 10 lbs. came from the stiffness of the flex arms 609, yielded improved performance and comfort. Such an increased activation force can be achieved by increasing the thickness of the flex arms 609, as the stiffness increases with the cube of thickness. Therefore, in some embodiments, the thickness of the flex arms 609 can be about 1.3 mm.

For example, Table 1 below shows the instances of participants' rankings of three different activation force options, with identical deployment energy and piston velocity. During this empirical study, users were asked to deploy all three applicators on their forearm, activating the applicator with their palm. Users deployed the applicators in a random order each time, and the order was recorded. After the three applicators were deployed, users were asked to rank the applicators 1-3, with 1 being the most comfortable and 3 being the least comfortable. Responses indicate that the 6 lbf activation force applicator is the least comfortable, with 68% of users ranking it 3rd. The 12 lbf applicator appears to be the most comfortable with almost 60% of users ranking it 1st. The responses to the 18 lbf applicator were mixed with 37%, 32%, and 20% split between 1st, 2nd, and 3rd rankings respectively. One user found there to be no difference between any of the three applicators and three users found no difference between the 12 lbf and 18 lbf applicators.

TABLE 1

| Rank | 6 lbf | 12 lbf | 18 lbf |
|------|-------|--------|--------|
| 1 | 1 | 11 | 7 |
| 2 | 4 | 5 | 6 |
| 3 | 13 | 1 | 4 |

Figure 29:
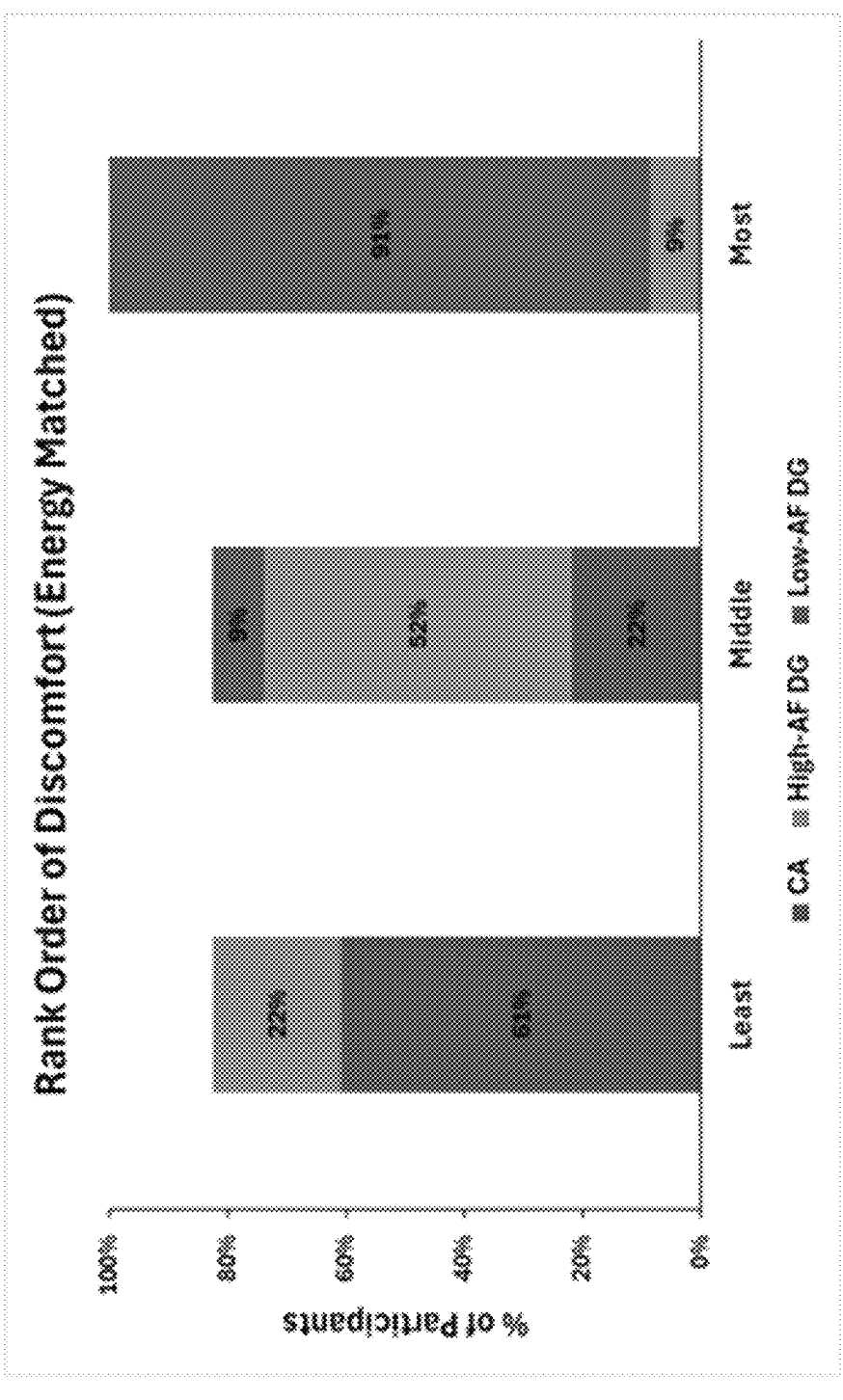
FIG. 29 illustrates the percentage of times three applicators were ranked as least, middle, or most uncomfortable in a study.

Additional empirical evidence supporting the premise that a low activation force may actually correspond to more discomfort to the user is shown in FIG. 29. FIG. 29 illustrates the percentage of times three applicators were ranked as least, middle, or most uncomfortable in a study. The three applicators were a low-activation force applicator (green), a high-activation force applicator with the same configuration (orange), and an applicator with a rounded piston face (blue), all with matched deployment energy and piston velocity. Despite having the lowest activation force, the overwhelming majority (91%) of users found the low-activation force applicator to be the most uncomfortable.

In one embodiment, the middle portion 401 may include one or more beams 606 each with a protrusion. In one example, the protrusions of the one or more beams 606 may connect to one or more grooves or one or more beams with protrusions of the bottom portion. In one example, the protrusions of the one or more beams 606 latch to protrusions of one or more beams 804 of the bottom portion 204 (illustrated in FIG. 12A). In some cases, and generally, the middle portion 401 contains two or more beams 606 with protrusions, and each protrusion engages with a groove or another protrusion of the bottom portion. For example, in one embodiment, the middle portion 401 has two beams 606 with protrusions, and the two beams 606 will be located on opposite sides of the middle portion. It is contemplated that more than two beams with protrusions could be used (e.g., three or beams with protrusions spaces evenly around the middle portion).

Furthermore, the middle portion 401 may include one or more ratchets 605. In some cases, and generally, as shown in FIG. 6A, the middle portion 401 contains eight ratchets 605. In other embodiments, the middle portion 401 may contain any numbers of ratchets 605 dispersed symmetrically around the outer circle. In some cases, the one or more first flexure interfaces 503 of the top portion 201 connect to the ratchets 605, increasing the resistance of downward movement of the top portion 201 to prevent inadvertent deployment of the device during storage, shipping, or manipulation by a user prior to use.

In one embodiment, as shown in FIG. 6B, the middle portion 401 includes one or more beams 607 each with a protrusion. In one example, the protrusions of the one or more beams 607 may connect, e.g. latch, to one or more grooves 703 of the piston portion 403 (illustrated in FIG. 12B). In some cases, and generally, the middle portion 401 contains two or more beams 607 with protrusions. For example, in the embodiment shown in FIG. 6B, the middle portion 401 has two beams 607 with protrusions.

Figures 7A, 7B, 7C:
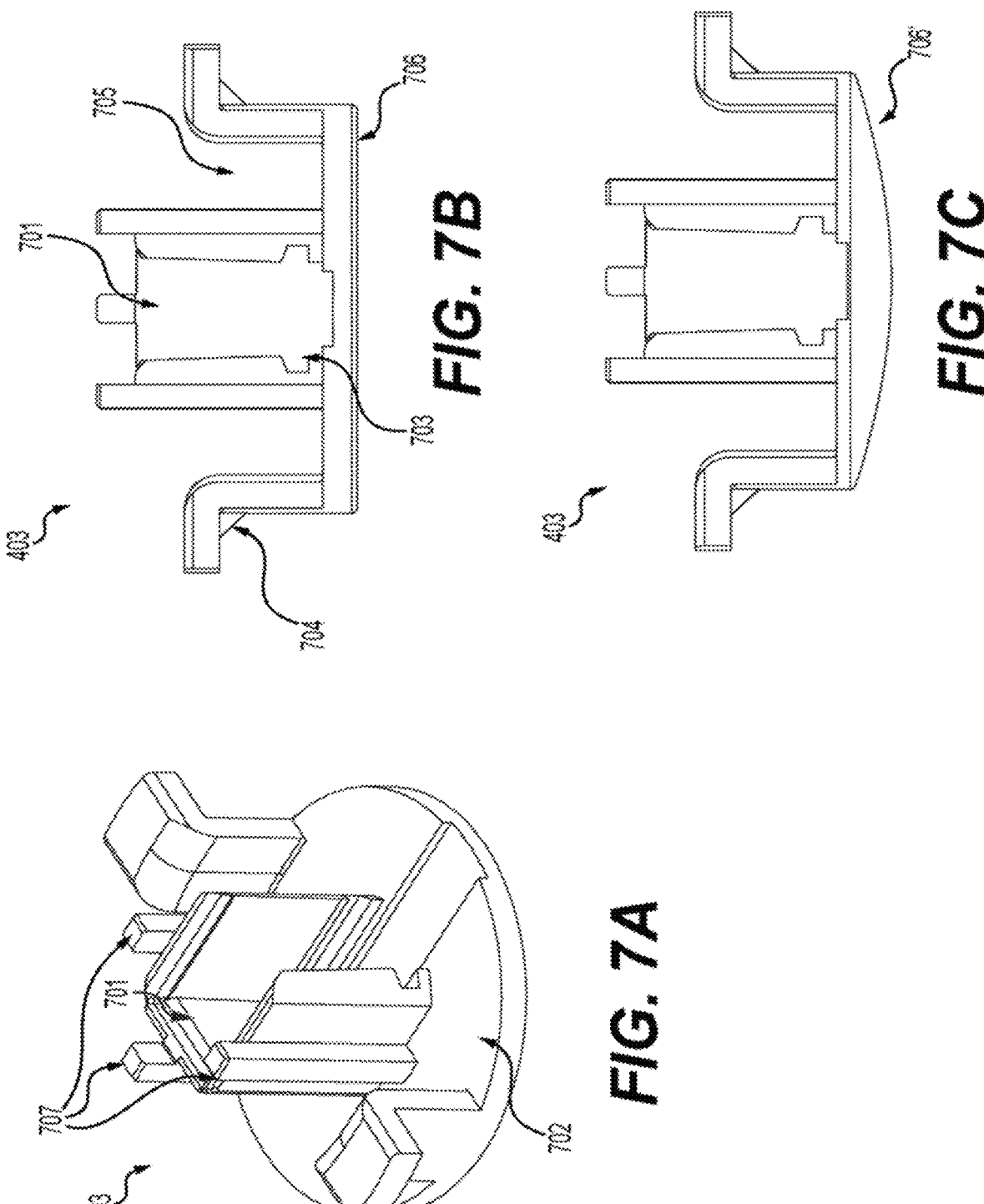
FIGS. 7A-7C are perspective (7A) and side cut-away (7B and 7C) views of a piston portion, according to exemplary embodiments.

As shown in FIG. 6C, the middle portion 401 may include one or more grooves 608. In one embodiment, the piston portion includes one or more beams, e.g., beams 707 shown in FIG. 7A below, and the one or more beams of the piston portion connect to, e.g., fit in, the one or more grooves 608. In this example, the one or more grooves 608 may act as piston guides which maintain the bottom surface of the piston, e.g., 706 and 706' as shown in FIGS. 7B and 7C below, parallel to the patient's skin during the release of the piston and the medicament patch. In one embodiment, the middle portion 401 includes one or more grooves 608. In other embodiment, the middle portion includes two or more grooves 608. For example, in the embodiment shown in FIG. 6C, the middle portion includes three grooves 608. The middle portion may include any number of grooves dispersed around the inner circle.

Figures 6D, 6E, 6F:
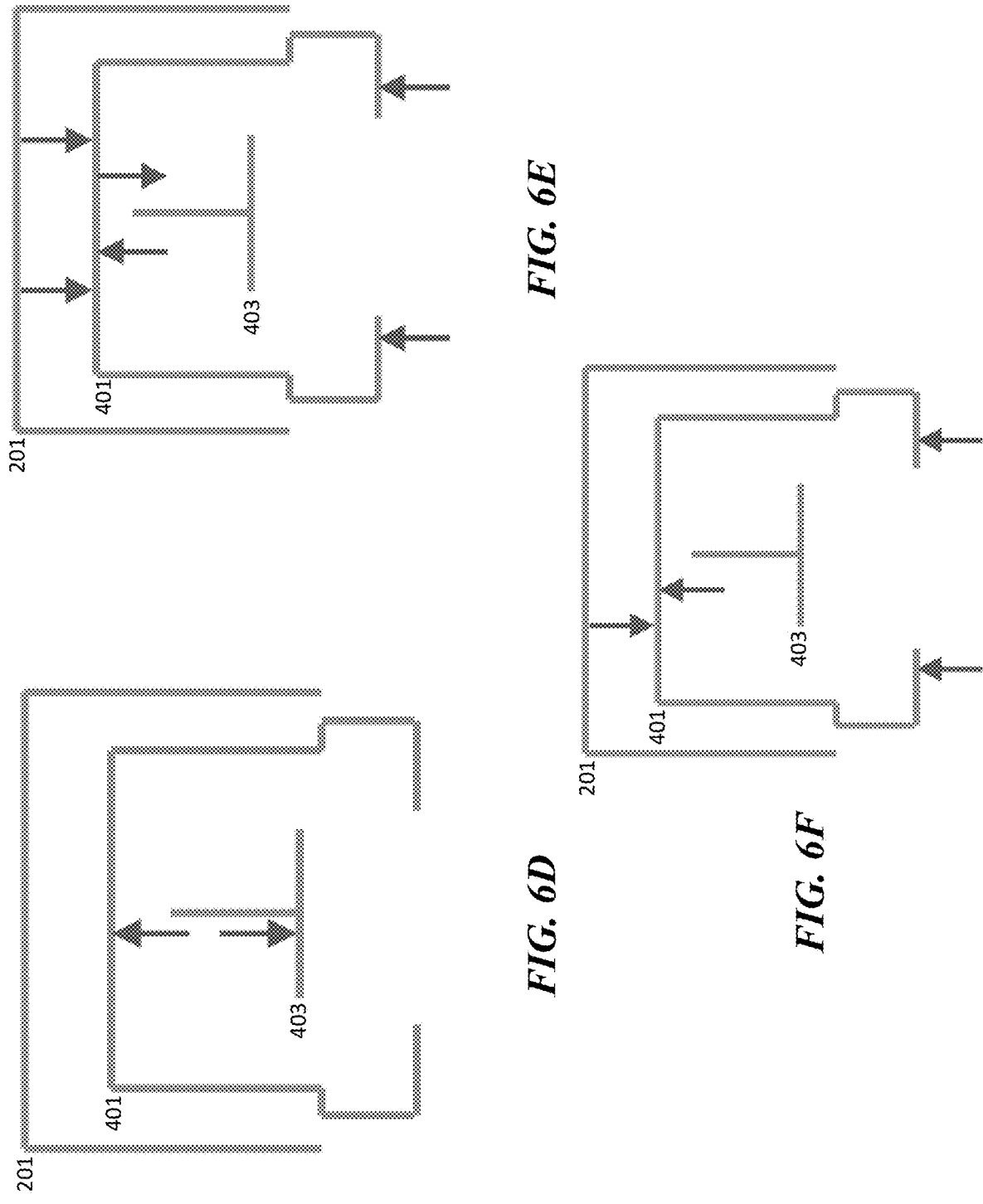
FIGS. 6D-6F illustrate the forces between various components of the disclosed applicator according to some embodiments of the present disclosure.

FIGS. 6D-6F illustrate the forces between various components of the disclosed applicator according to some embodiments of the present disclosure. In particular, FIGS. 6D-6F illustrate interactions between the top portion 201, the middle portion 401, and the piston portion 403. FIG. 6D illustrates the various forces when the system makes contact with the skin of a subject, and the spring forces between the middle portion 401 and the piston portion 403 are in opposite directions but in equilibrium. When the piston portion 403 is released, the compressible member 402 (not shown) can accelerate the piston portion 403 downward, such as via a spring force. At the same time, the top of the compressible member 402 can exert an equal and opposite force on the middle portion 401, causing it to accelerate upward. In some embodiments, the middle portion 401 is heavier than the piston portion 403 and therefore moves less.

However, upward motion of the middle portion 401 is undesirable and it is beneficial to reduce this as much as possible. Moreover, in the absence of other force interactions, conservation of momentum may dictate that the ratio of the downward travel distance of the piston portion 403 to the upward travel distance of the middle portion 401 is equivalent to the ratio of their respective masses.

In FIG. 6E, which is before release of the piston portion 403, the forces influencing the upward travel of the middle portion 401 immediately before and after release of the piston portion 403 can include the force of the compressible member 402 (20 lbs.), the activation force from the flex arms 609 (not shown, 10 lbs.), the activation unlatching force (2 lbs.), and a skin contact force (12 lbs.). Therefore, the net force acting on the middle portion 401 after release (FIG. 6F) is approximately equivalent to the force of the compressible member 402 plus the unlatching force (about 22 lbs.). While it can be difficult to adjust the forces, the masses of the components can be adjusted to more effectively manage movement.

In some embodiments, the piston portion 403 can have the lowest mass of the three components and the combination of the masses of the middle portion 401 and the piston portion 403 can be slightly higher than the mass of the top portion 201. The largest mass generally can be the top portion 201 combined with the user's hand that will be pressing and activating the system. In some embodiments, because the top portion 201 and the middle portion 401 can move relative to each other to initiate release of the piston portion 403, these masses do not combine together at the moment of release. In some embodiments, the term "overtravel" can be used to describe the distance between the top portion 201 and the middle portion 401 when the piston portion 403 is released. The overtravel distance can be used to accommodate manufacturing tolerances and other real world dimensional variations.

Figure 6H:
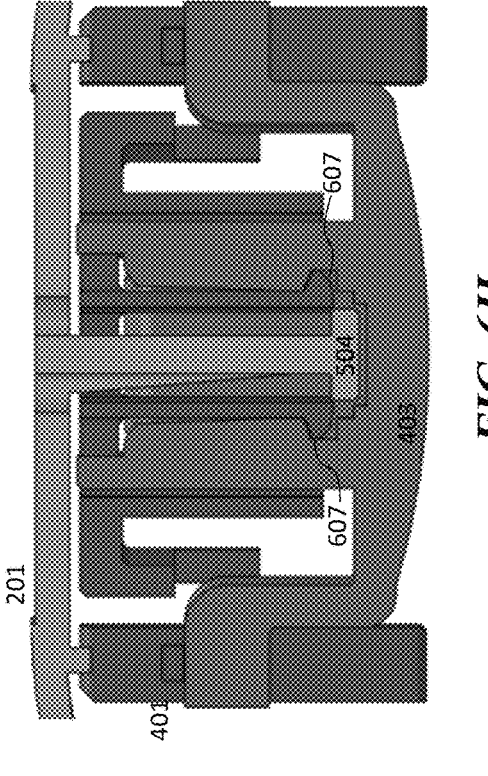
FIGS. 6G-6I illustrate an overtravel management configuration of the disclosed applicator according to some embodiments of the present disclosure.
Figure 6G:
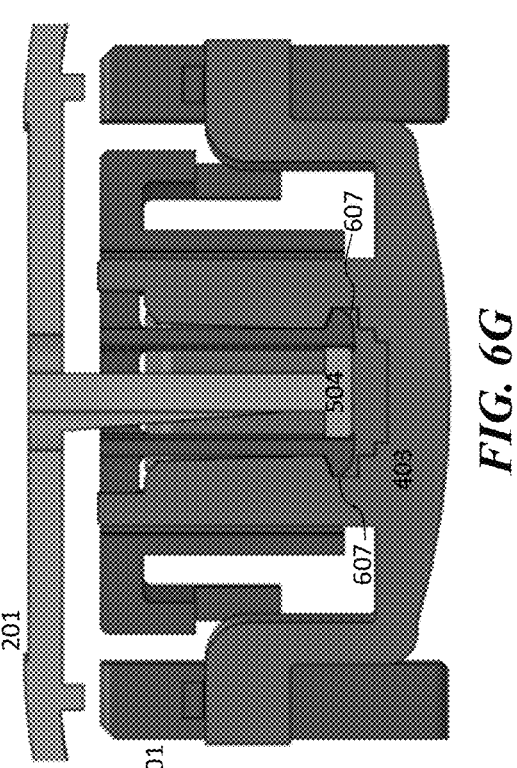
Figure 6I:
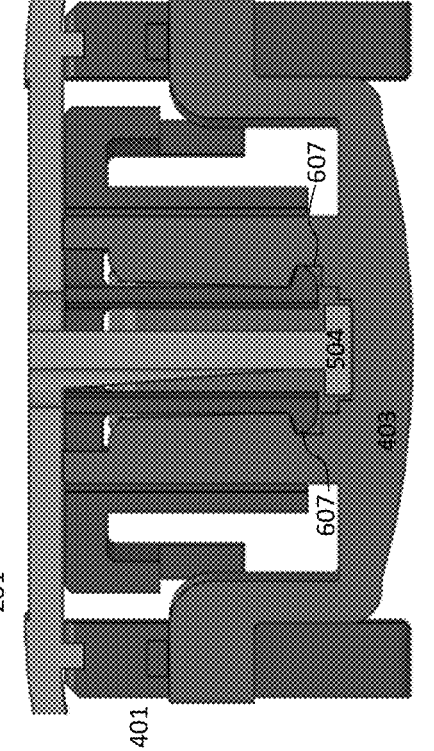

FIGS. 6G-6I illustrate an overtravel management configuration of the disclosed applicator 200 according to some embodiments of the present disclosure. In FIG. 6G, which is prior to release of the piston portion 403, the middle beam 504 of the top portion 201 locks the beams 607 of the middle portion 401 to hold the piston portion 403 in place. In FIG. 6H, which illustrates the moment of activation and release, the top portion 201 moves downward and the middle beam 504 clears the beams 607 to release the piston portion 403. FIG. 6I illustrates overtravel, the subsequent distance traveled between the top portion 201 and the middle portion 401 before they physically contact each other. In some embodiments, once the overtravel distance is traversed, the masses of the top portion 201 and the user's hand can combine with the masses of the middle portion 401 and the bottom portion 204 (not shown) to slow the upward travel of the middle portion 401.

Figure 6K:
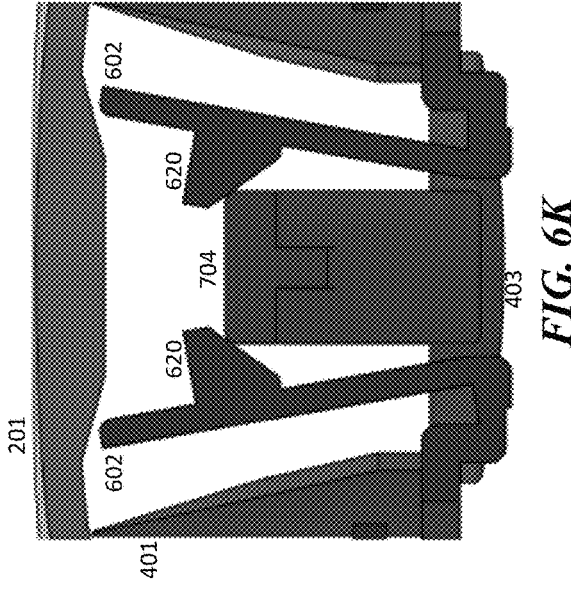
FIGS. 6J-6L illustrate a zip-tie configuration of the disclosed applicator according to some embodiments of the present disclosure.
Figure 6J:
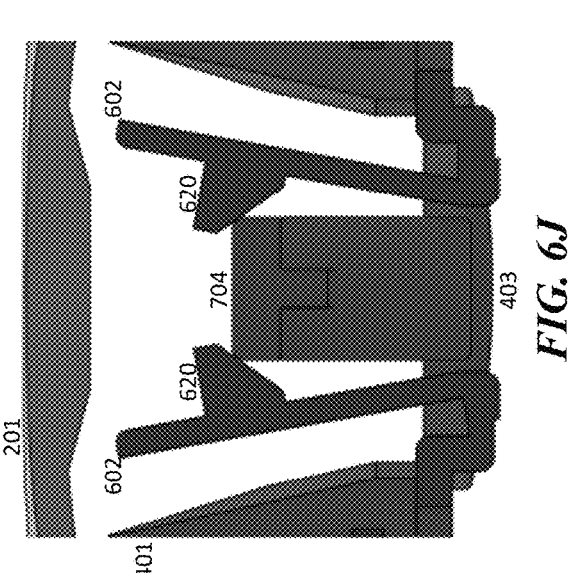
Figure 6L:
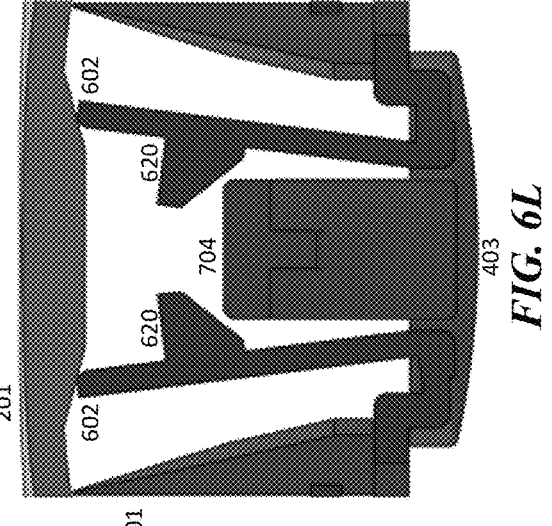

FIGS. 6J-6L illustrate a zip-tie configuration of the disclosed applicator 200 according to some embodiments of the present disclosure. In some embodiments, a "zip-tie" can refer to the combination of the beam 602 and associated protrusion 620. Therefore, FIGS. 6J-6L illustrates two "zip-ties." In some embodiments, the purpose of the zip-ties can be to lock the middle portion 401 to the top portion 201 after the piston portion 403 begins downward travel and before the full overtravel distance has been traversed. Prior to release, as shown in FIG. 6J, the arm 704 of the piston portion 403 holds the zip-ties such that they are splayed outwards (i.e., the arm 704 contacts the protrusions 620 and forces the beams 602 to bend outwardly). At the moment of release, as shown in FIG. 6K, the top portion 201 descends but does not yet contact the middle portion 401 or the zip-ties yet. As the piston portion 403 initiates its downward motion, as shown in FIG. 6L, the arm 704 of the piston portion 403 comes out of contact with the protrusion 620, allowing the zip-ties to unbend and move inward. As they move inward and straighten out, they will eventually come into contact with the inner surface of the top portion 201. In some embodiments, the inner surface of the top portion 201 can be a ramped surface. As this contact occurs, the upward travel of the middle portion 401 is arrested.

FIG. 7A-7C are perspective views of a piston portion 403. The piston portion 403 may include a middle portion 701 and a bottom portion 702. Generally, as shown in FIG. 7A, the bottom portion 702 is substantially cylindrical. In some embodiments, the piston portion 403 may include one or more beams 707 dispersed around the middle portion 701. As discussed above, the one or more beams 707 of the piston portion may connect to, e.g., fit in, the one or more grooves 608 of the middle portion. In one embodiment, the piston portion 403 includes one or more beams 707. In another embodiment, the piston portion includes two or more beams 707. For example, in the embodiment shown in FIG. 7A, the piston portion includes three beams 707. The piston portion may include any number of beams.

As shown in FIG. 7B, the middle portion 701 may include one or more grooves 703. In one example, the protrusions of the one or more beams 607 of the middle portion 401 arc connected, e.g., latched, onto the one or more grooves 703 (illustrated in FIG. 12B). In one embodiment, the piston portion 403 includes one or more arms 704 as retention arms. The arms 704 can fit within the beams 602 of the middle portion 401. When placed within the middle portion 401, the arms 704 spread inner protrusions 620 of the beams 602. The position of the arms 704 within the beams 602 and compression by the protrusions 620, serves to the stabilize the piston position and aid in downward motion of the piston 403. In one embodiment, the compressible member, e.g., springs, are positioned in the opening 705 of the piston portion 403. Furthermore, the piston portion has a bottom face 706, 706' that pushes downwards onto the patch holder holding the medicament patch. The bottom face 706, 706' may be any shape and/or geometry to facilitate a reliable and quick release of the medicament patch. As an example, the bottom face 706, 706' may be flat (FIG. 7B) or round (FIG. 7C).

In some embodiments, a smaller and rounder bottom face is most desirable and yields the most comfortable user experience while maintaining effective delivery efficiency. In some embodiments, this means that the skin contact diameter can be smaller. In some embodiments, the piston portion 403 can have a diameter of about 22.0 mm and the rounded face can have a radius of curvature of about 40 mm. If the face 706 is too big, a lot of energy can be lost to the skin surrounding the MAP. However, by using a smaller and rounder piston face 706, the energy can be more effectively focused on the center of the MAP. The force then moves outward on the MAP to more comfortably deliver the MAP to the skin of the subject, such as by reducing skin tenting.

Table 2 below illustrates a summary of empirical evidence comparing various iterations of an applicator with the smaller and round bottom piston face (22.0 mm diameter and 40 mm radius of curvature of the dome) and increased activation force (10 lbf) according to the disclosed embodiments (rows 2-5). Row 1 is an applicator that is used as a benchmark for testing that has effective delivery efficiency but is undesirable for real-world applications to patients because of its intolerability. The air gap measurement, performed via Optical Coherence Tomography (OCT) on the MAP just after deployment, refers to the distance between the backing of the MAP and the subject's skin. The residual needle height refers to the measurement of the needles post deployment. The penetration depth reflects the amount the microneedle has penetrated the skin of the subject and can be estimated by subtracting the air gap from the total length of the microneedle (900 μm in this case).

TABLE 2

| Group | Applicator | Air Gap [um] | Residual Needle Height [um] | Penetration depth (900 um assumed starting height) [μm] |
|---|---|---|---|---|
| 1 | Clinical, benchmark (7.3 m/s, 1.9 mJ) | 341 | 484 | 559 |
| 2 | 14 m/s 2.5 mJ | 267 | 422 | 633 |
| 3 | 12 m/s 2.0 mJ | 329 | 502 | 571 |
| 4 | 10.4 m/s 2.0 mJ | 341 | 512 | 559 |
| 5 | 9 m/s 1.5 mJ | 327 | 513 | 573 |

Air gap results show that groups 2-5 performed as well or better than group 1. There was no significant difference in air gap between group 1 and groups 3, 4, and 5. Groups 2, 3, and 5 had air gaps smaller than group 1. Most notably, group 2 had air gaps below 300 μm, significantly smaller than that of group 1. Analysis of residual needle height again shows superior performance of group 2 with needle heights 422 μm on average, significantly smaller than group 1. Groups 3, 4, and 5 had residual needle heights not significantly different from group 1, as well.

Group 2 performed the best overall compared to both group 1 and groups 3-5 with air gaps below 300 μm and residual needle height in the low 400 μm. Groups 3, 4, and 5 also performed well with no differences between their deployment outcomes and the clinical applicator. Most surprisingly, group 5 performed as well as group 1 and groups 2-4 despite the significant reduction in energy per needle (1.5 mJ) and low velocity (9.0 m/s). This may demonstrate how the disclosed modifications made to the applicator create conditions that help to reduce deployment outcomes like increased skin doming. Therefore, all the disclosed applicator groups (groups 2-5) meet the goal of performing as good or better than the group 1 applicator.

Table 3 below illustrates a summary of empirical evidence comparing various iterations of an applicator with the smaller and round bottom piston face (22.0 mm diameter and 40 mm radius of curvature of the dome) and increased activation force (10 lbf) according to the disclosed embodiments (rows 2-6). Rows 1 and 7 are applicators that are used as a benchmark for testing that has effective delivery efficiency but are undesirable for real-world applications to patients because of its intolerability. The pre-deployment needle height refers to the length of the microneedle (including base and tip). The height delivered refers to the residual needle height subtracted from the pre-deployment needle height.

TABLE 3

| Group | Pre-deployment needle height [um] | Air Gap [um] | Residual Needle Height [um] | Height Delivered (Primary-Residual NH) [um] | Penetration Depth (Primary NH-Air Gap) [um] |
|---|---|---|---|---|---|
| 1 | 907 | 366 | 530 | 377 | 541 |
| 2 | 901 | 274 | 471 | 430 | 627 |
| 3 | 913 | 490 | 644 | 269 | 423 |
| 4 | 892 | 317 | 510 | 381 | 574 |
| 5 | 903 | 311 | 531 | 372 | 592 |
| 6 | 890 | 367 | 556 | 334 | 526 |
| 7 | 904 | 368 | 566 | 338 | 536 |

Table 4 below illustrates the dimensions and specifications of the various applicators referenced in Table 3.

TABLE 4

| Group | Velocity [m/s] | Energy/needle [mJ] | Piston mass [g] | Array size |
|---|---|---|---|---|
| 1 | 7.3 | 1.9 | 7.5 | 121 |
| 2 | 14 | 2.7 | 7.4 | 277 |
| 3 | 14 | 0.7 | 2.0 | 277 |
| 4 | 12.5 | 2.1 | 7.4 | 277 |
| 5 | 10 | 1.4 | 7.4 | 277 |
| 6 | 9 | 1.1 | 7.4 | 277 |
| 7 | 7.3 | 1.9 | 7.5 | 121 |

Air gap data demonstrated good performance of groups 2-6. All but one group (group 3) performed statistically no different from the clinical applicator even when velocity was as low as 9 m/s. The 14 m/s, 2.7 mJ group performed significantly better than group 1, with average air gaps of about 274 μm. Groups 2 (14 m/s), 4 (12 m/s), and 5 (10 m/s) performed well, with air gaps and undeployed release equal to or lower than that of group 1. Group 5 is the lead configuration as it appears to perform well compared to group 1 with the lowest velocity and therefore highest comfort.

Table 5 below illustrates a summary of empirical results of applicators with varying piston face diameters.

TABLE 5

| Group | Piston type, Energy/needle | Pre-deployment needle height [um] | Air Gap [um] | Residual Needle Height [um] | Height Delivered (Primary Residual NH) [um] | Penetration Depth (Primary NH-Air Gap) [um] |
|---|---|---|---|---|---|---|
| 1 | Clinical, benchmark, 1.9 mJ | 885 | 306 | 442 | 443 | 579 |
| 2 | 24.6 mm, flat, 2.34 mJ | 905 | 425 | 556 | 349 | 480 |
| 3 | 20 mm, bossed 2.28 mJ | 906 | 370 | 514 | 391 | 536 |
| 4 | 24.6 mm, domed 2.34 mJ | 905 | 353 | 498 | 406 | 552 |

The first deployment outcome is air gap height, measured between the backing and the skin surface. A small air gap height can be correlated with deeper penetration depths and better deployment outcomes. Group 1 produced air gaps of 425 μm on average, significantly larger than group 1 (306 μm), despite having a larger energy per needle. Groups 3 and 4 produced reduced air gaps compared to group 2. Compared to group 1, air gap height was significantly larger for groups 2 and 3, while group 4 produced air gaps around 353 μm on average.

The second primary outcome is needle height delivered, determined by subtracting the residual needle height from the primary needle height. This represents the length of needle delivered into the skin during deployment and is an important metric for delivery efficiency. Data analysis shows group 1 delivered the most needle length (443 μm), followed by group 4 (406 μm). Group 2 performed the worst, delivering only 350 μm in length.

The results of this study indicate there is some improvement in deployment efficiency generated by the boss piston and domed piston. Both groups had smaller air gaps, smaller residual needle height, and delivered more needle height than the standard piston. However, neither group performed as well as the clinical applicator. Piston shape and size are likely not the only advantages of the clinical applicator, and activation force and lower diameter may also play a role in creating the continued superior deployment outcomes, as discussed above in relation to Tables 1-4.

Table 6 illustrates a comparison between various applicators, including the benchmark clinical applicator; an applicator with a reduced inner diameter (ID) of the piston (27 mm and flat face); an applicator with increased activation force (10 lbf), a reduced inner diameter of the piston (27 mm), and the domed piston face; and an applicator without such modifications (35.5 mm and flat face).

TABLE 6

| Group | Applicator | Pre-deployment needle height [um] | Air Gap [um] | Penetration Depth (Primary NH-Air Gap) [um] |
|---|---|---|---|---|
| 1 | Benchmark | 921 | 311 | 611 |
| 2 | Standard | 910 | 445 | 465 |
| 3 | Reduced ID | 905 | 414 | 492 |
| 4 | Combined modifications | 900 | 277 | 623 |

Air gap results show that the reduced diameter lower improved deployment outcomes only marginally. Group 3 (reduced ID) produced a non-statistically significant reduction in air gap of 30 μm compared to group 2 (standard). Group 4 combined all current improvement concepts including, increased activation force, reduced ID lower, and domed piston. The resulting air gap (277 μm) was the best overall, even compared to group 1 (311 μm). Penetration depth data demonstrates again that Group 4 had improved performance compared to other groups and was not significantly different from the clinical applicator. The reduced ID lower marginally improved penetration depth compared to the standard, though there was no significant difference between the two groups.

The results of this experiment demonstrate that the combined effect of all disclosed improvement concepts can generate deployment outcomes as good or better than the clinical applicator. The data showed group 4 significantly reduced air gap compared to other groups and was not significantly different from the clinical applicator. The reduced ID lower used in group 3 did show a small, non-significant improvement in deployment outcomes compared to the standard when all other parameters were matched. However, the improvement did not create enough of an effect to reach the performance of the clinical applicator. The reduced diameter lower attempted to improve deployment outcomes by creating a larger skin dome height. It is possible that the skin dome was not maximized due to the low activation force of the DG (~6 lbf), which led to only a small improvement in deployment outcomes. The configuration of group 4 included the small ID lower and an increased activation force that could have generated a maximum height skin dome, which helped to generate the improved deployment outcomes. The results demonstrate that the combined effect of a few small changes to the geometry and mechanics may lead to significant improvements in deployment outcomes. With an optimized applicator design, work can be done to improve factors that impact user experience like decreasing velocity.

Table 7 illustrates empirical data regarding deployment outcomes from applicator pistons with different outer diameters. Both groups utilize a reduced 27 mm inner diameter, 2.0 mJ per needle, and 10-12 lbf activation force.

TABLE 7

| Group | Piston | Pre-deployment needle height [um] | Air Gap [um] | Residual Needle Height [um] | Height Delivered (Primary Residual NH) [um] | Penetration Depth (Primary NH-Air Gap) [um] |
|---|---|---|---|---|---|---|
| 1 | 24.6 mm, domed | 918 | 309 | 509 | 408 | 609 |
| 2 | 22 mm, domed | 932 | 276 | 478 | 453 | 655 |

Deployment data demonstrates that the small diameter piston reduced the air gap by 32 μm on average. Similarly, the small diameter piston produced, on average, smaller residual needle heights than the standard piston, which suggests better penetration depth. The small diameter piston may deliver more energy to the array than the larger piston which loses some of its energy into the skin around the array. Small changes to the applicator can contribute significantly to the overall performance when accompanied by other changes proven to be impactful.

Generally, to allow the patch to be oriented correctly with respect to a target area of a patient's skin, and to provide a configuration wherein the piston 403 can push the patch off the applicator 200, the patch 100 is held in a cylindrical shaped holder. Specifically, the patch is held by a holder that has a generally open region and a rigid rim or periphery. The patch is secured at one or more points along the patch's edge to the inner rim of the holder with the patch spanning the open region. The piston passes through the open region when activated to push the patch downward.

Figure 8A:
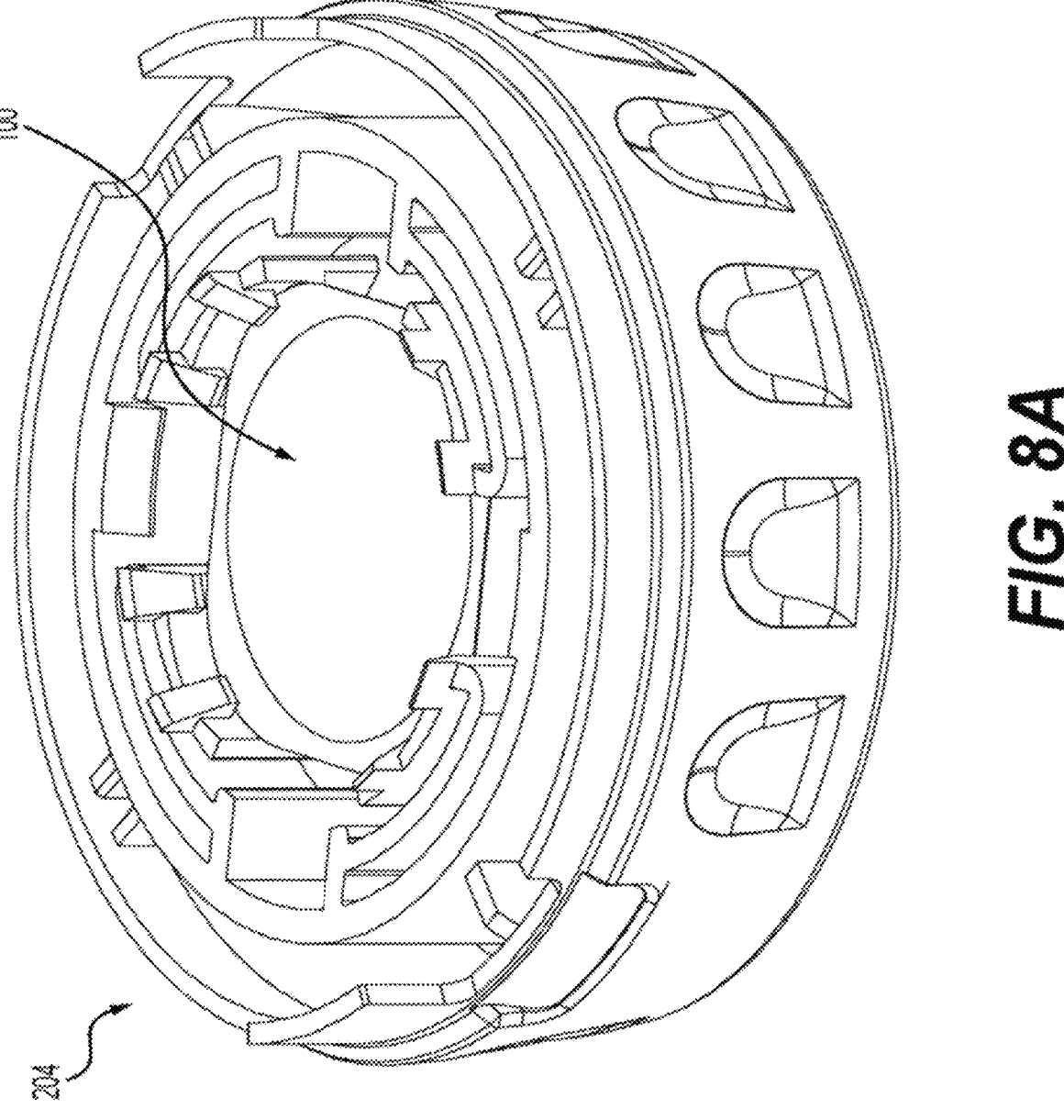
FIGS. 8A-8C are perspective views (8A and 8B) and a side cut-away view (8C) of a bottom portion holding a medicament patch, according to exemplary embodiments.
Figure 8B:
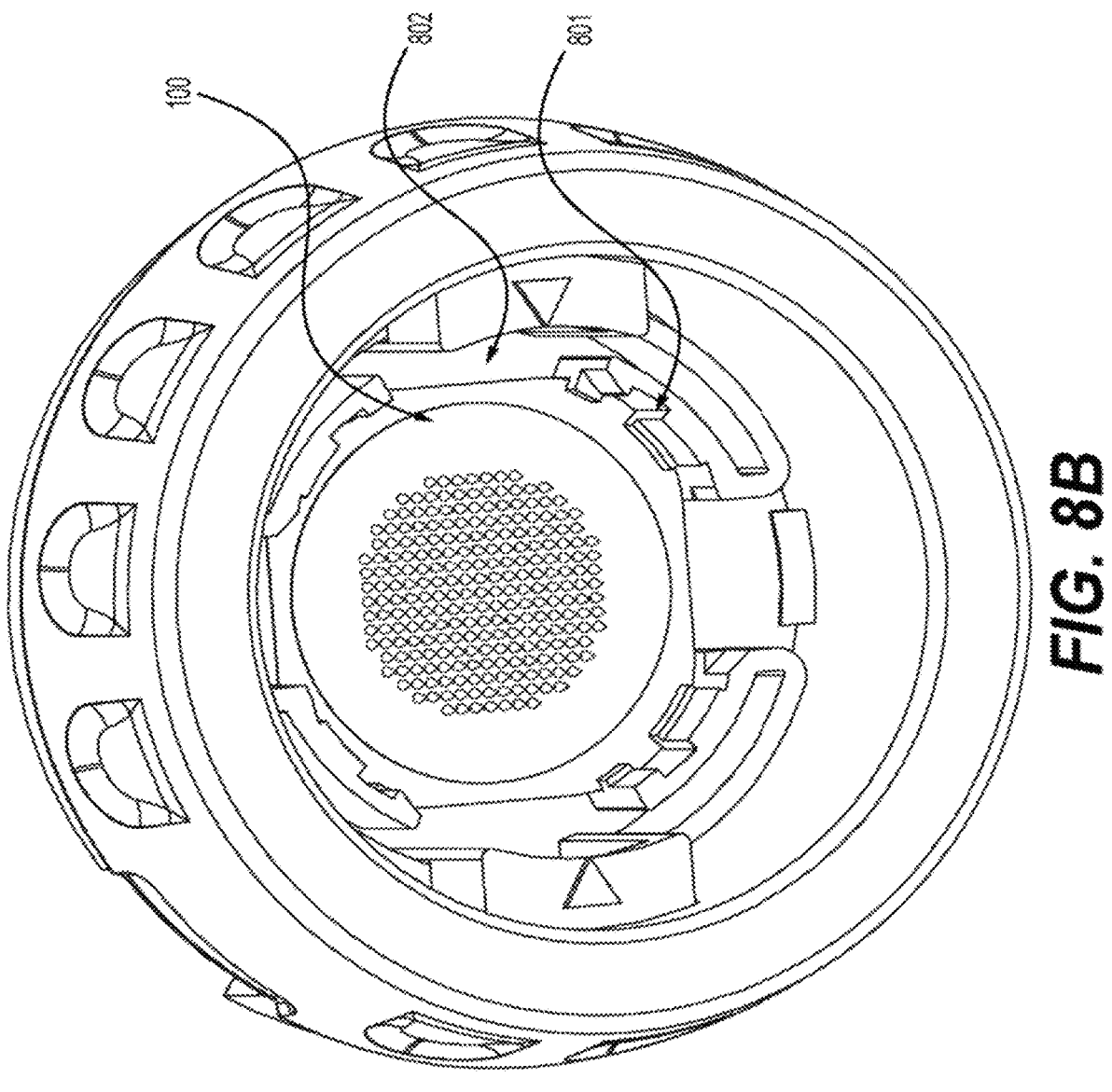
Figure 8C:
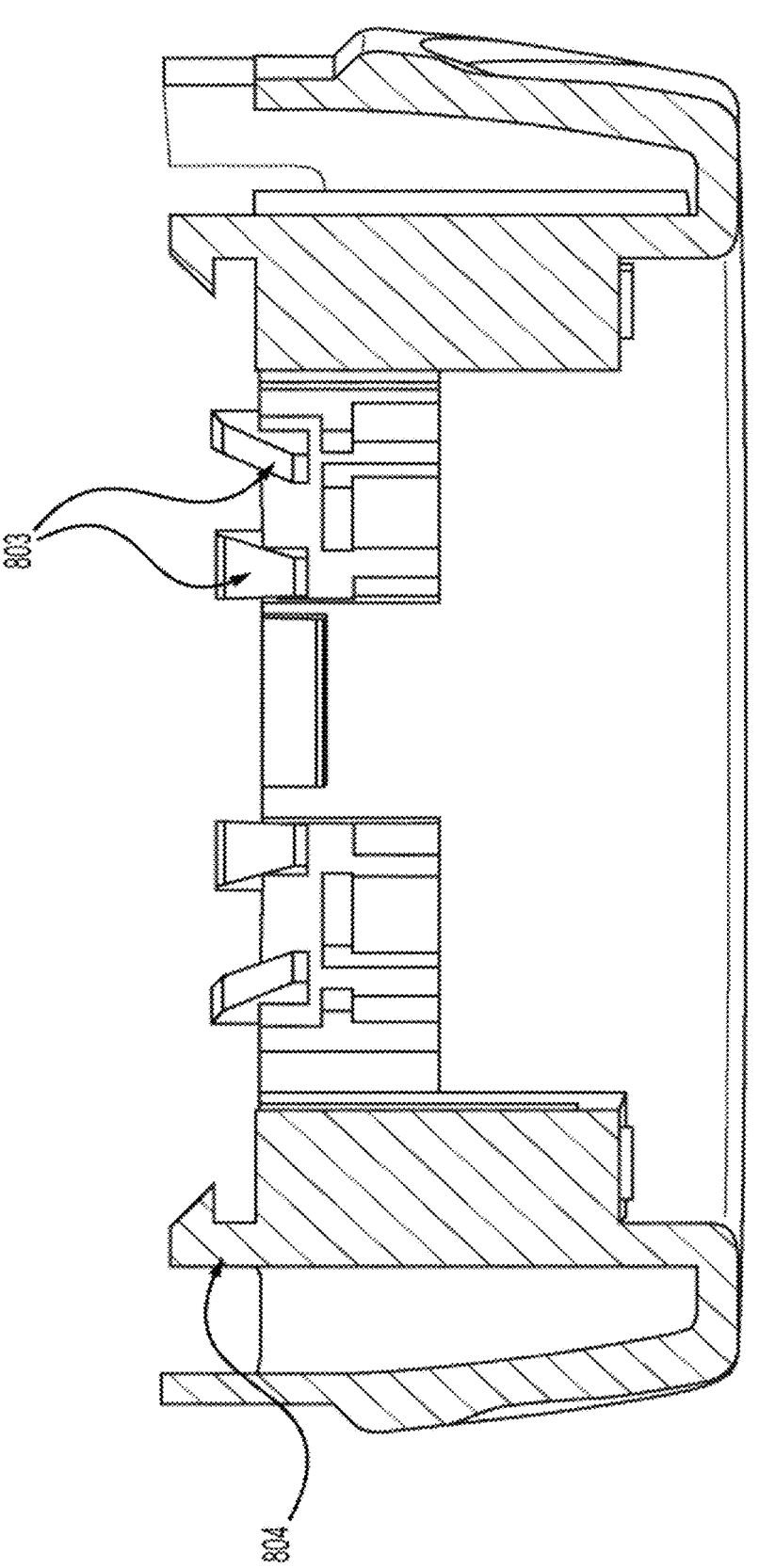
Figure 12A:
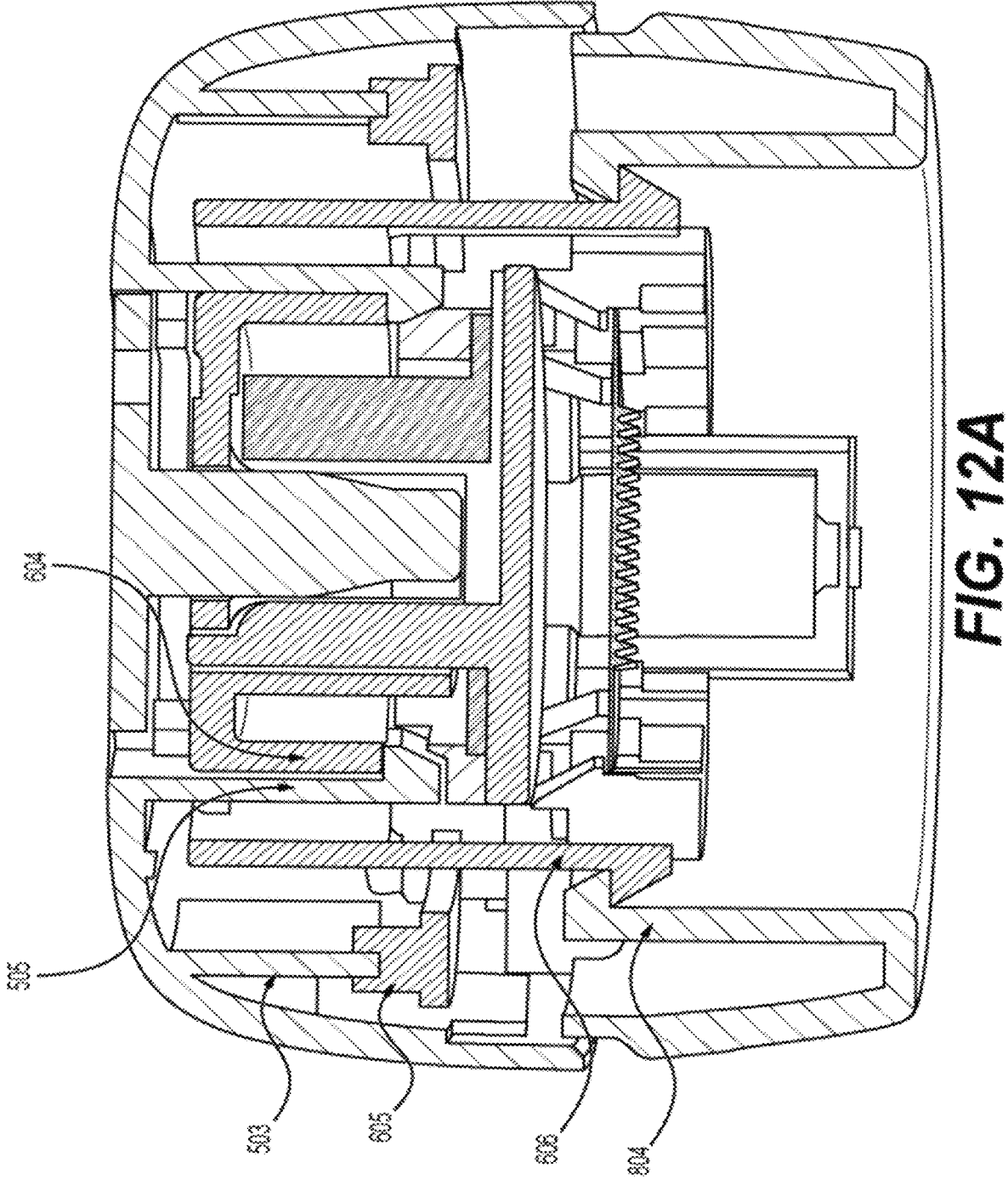
FIGS. 12A and 12B are side cut-away views of the applicator device, according to exemplary embodiments.

Specific embodiments of the patch holder and the bottom portion are discussed below. FIG. 8A-8C are perspective views of a bottom portion 204 holding a medicament patch 100. In one embodiment, the bottom portion 204 includes a patch holder 801 that holds the medicament patch 100 and an open center portion 802. In one example, the patch holder 801 the medicament patch with one or more ramps 803. In one embodiment, the medicament patch 100 and the patch holder 801 are sized such that the patch 100 is larger than the open center portion 802 in at least one dimension such that the medicament patch 100 can be held by the one or more ramps 803 of the patch holder 801 without passing through the center portion 802. In one embodiment, the bottom portion 204 includes one or more beams with protrusions 804. In one example, the protrusions of the one or more beams 804 connect (e.g., latch) to the protrusions of one or more beams 606 of the middle portion (FIG. 12A).

As shown in FIG. 8B, the holder 801 is formed by a hook shaped arm. The holder can be formed of a semi-rigid material that flexes to allow loading of the patch. It is contemplated that the holder 801 can have other shapes and can be formed of a variety of suitable materials. In some embodiments, movement of the piston 403 pushes the holder 801 outward to release the patch, as described further below.

Figures 9A, 9B:
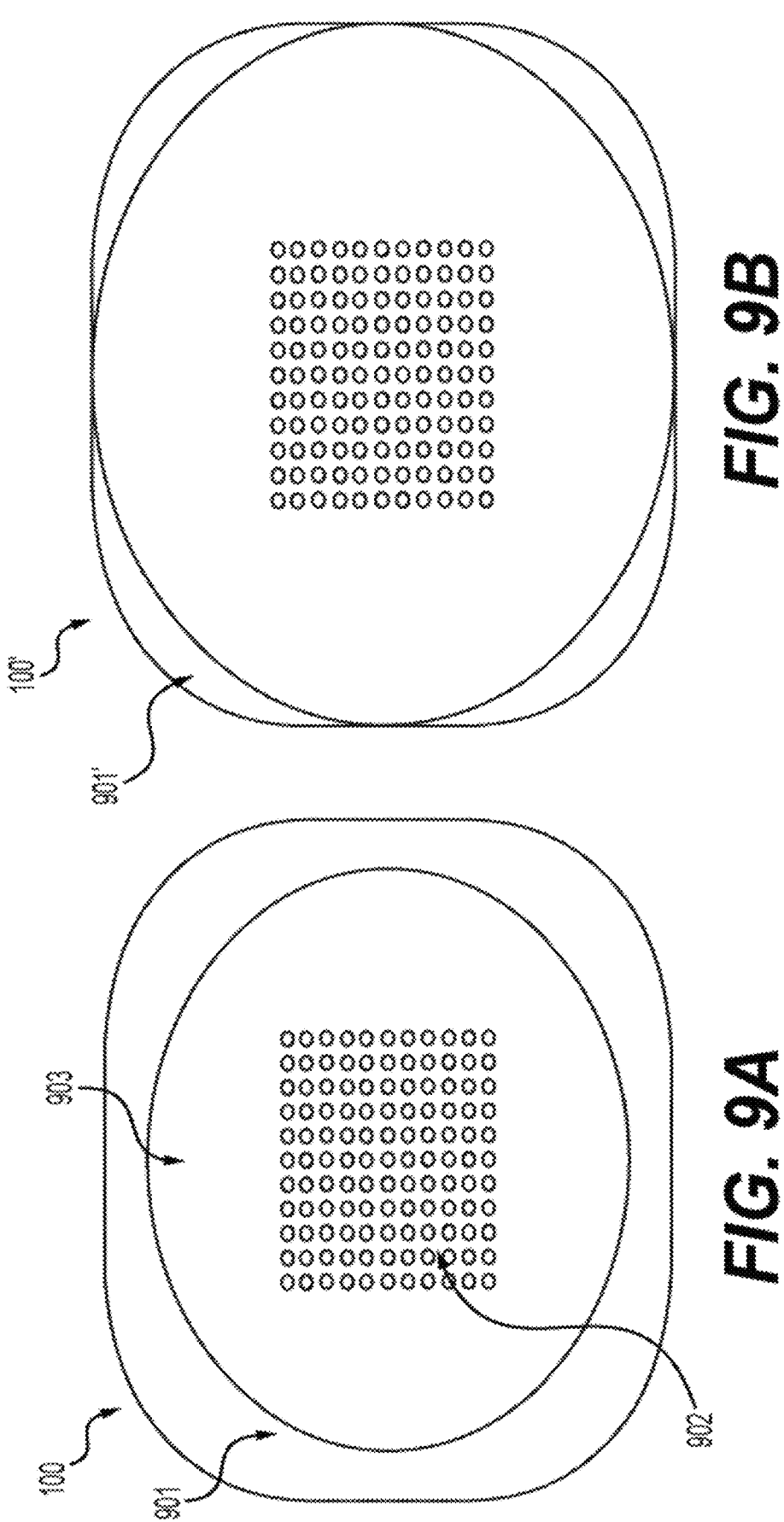
FIGS. 9A and 9B are exemplary patch configurations for use with disclosed applicator and patch systems.

Suitable patches should be designed to be released from the bottom portion by application of pressure from the piston. FIGS. 9A and 9B are exemplary patch configurations for use with disclosed applicator and patch systems. As shown, the patch 100, 100' can include a backing layer 901, 901', and adhesive region 903, and an area containing medicament 902. The adhesive region 903 may extend into the area containing medicament 902 (e.g., a microneedle an-ay) so long as the adhesive is not placed in a manner that adversely affected the microneedles or their detachment into the skin.

The backing layer can extend from the periphery of the adhesive region 903 along the entire periphery, as shown in FIG. 9A, or from a portion of the adhesive, e.g., at corners, as shown in the FIG. 9B. In some embodiments, at least a portion of the patch, e.g., the backing layer, may have sufficient flexibility to allow the patch to be pushed through the bottom portion of the applicator device 200. To provide sufficient flexibility, the backing layer can be formed of materials having mechanical properties and or dimensions that provide a desired degree of flexibility. For example, suitable materials for the backing layer can be polyesters (e.g., polyethylene terephthalate or polyethylene terephthalate glycol between about 0.002' or 0.005" thick), paper, aluminum or other flexible materials.

Figures 10A, 10B, 10C:
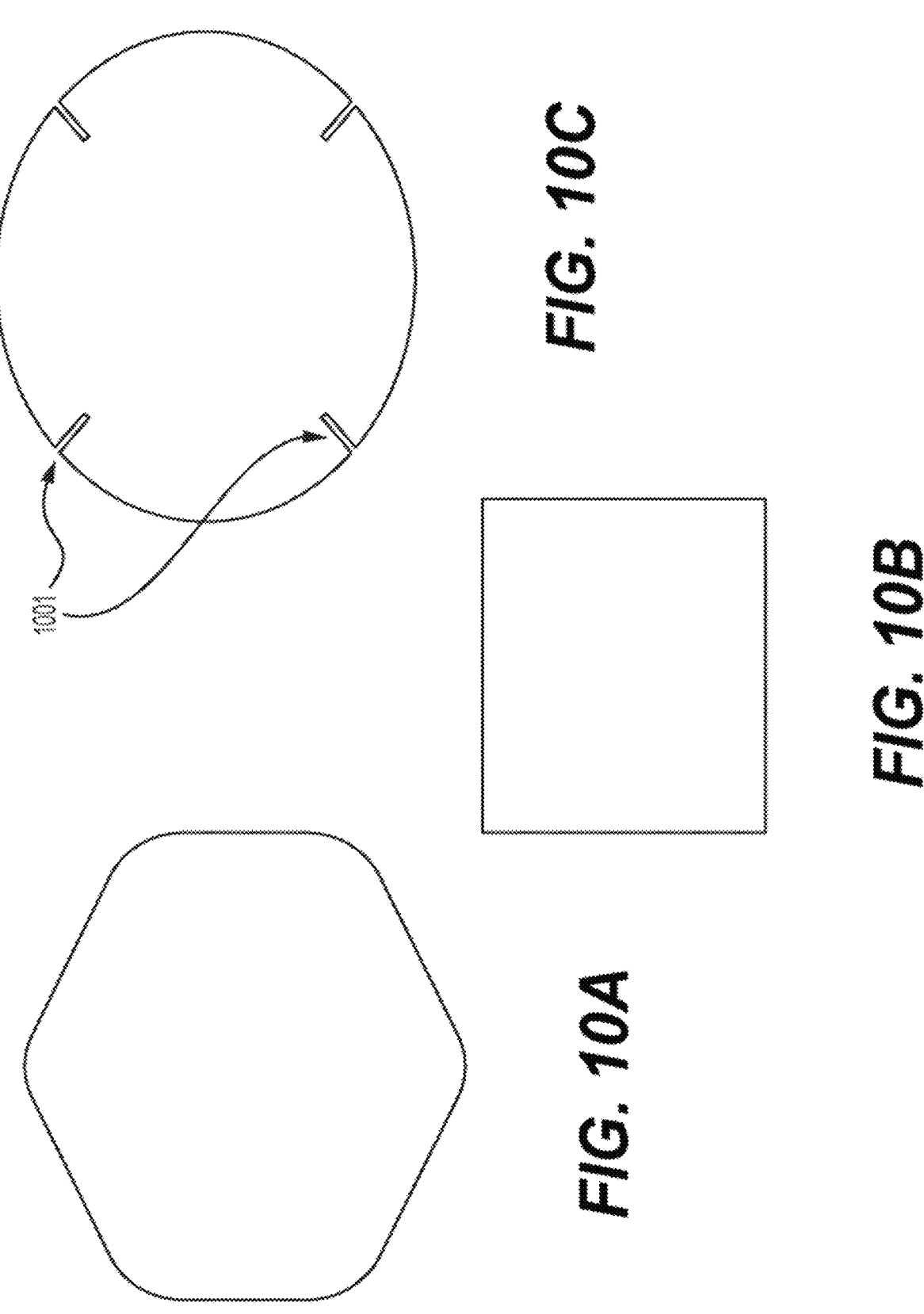
FIGS. 10A-10C are alternative exemplary embodiments for a backing portion of a medicament patch.

Furthermore, the patch 100, including the entire patch or backing layer, can have a variety of shapes. For example, FIGS. 10A-C are alternative exemplary embodiments for a backing portion of a medicament patch. The patches include polygon (e.g., hexagon (FIG. 10A) or octagon), square (FIG. 10B), or circular (FIG. 10C). Further, other shapes are contemplated such as triangles, ovoid, square with rounded edges (scround or squircle) as shown in FIG. 9A or 9B. In addition, the backing layers can be modified to allow increased flexibility in certain areas. For example, cuts or indentations 1001 can be provided at certain areas along the backing layer periphery, as shown in FIG. 10C.

Figure 11B:
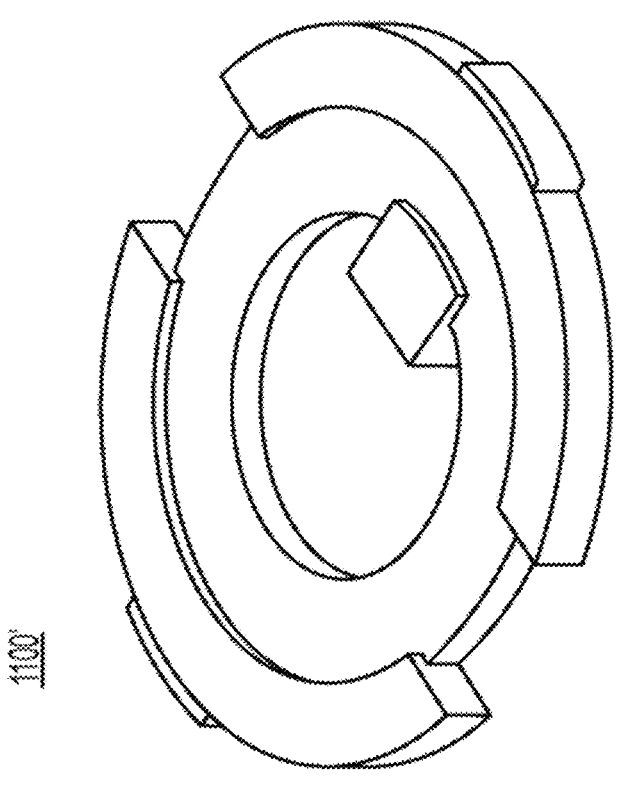
FIGS. 11A and 11B are illustrations of piston weights for use in the applicator device, according to exemplary embodiments.
Figure 11A:
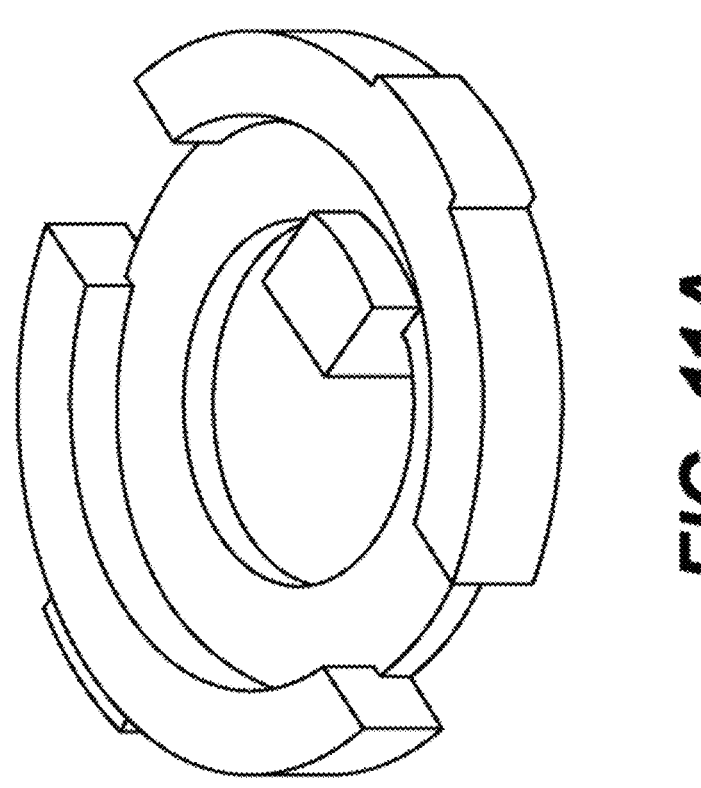

In some embodiments, the applicator device further includes a piston weight. FIGS. 11A and 11B are piston weights 1100 and 1100' according to exemplary embodiments. In one embodiment, the piston weight is added to increase the momentum of the piston portion when being pushed downwards, thereby increasing the energy applied to the medicament patch 100 to facilitate the deposit of the needles at a desired depth within the skin. In one embodiment, the piston weight is positioned between the piston portion 403 and the middle portion 401. In one example, the piston weight is positioned between the compressible member, e.g., a spring, and the piston portion. The piston weight can be made of any suitable material, shape, and weight to meet the needs. Generally, the piston weight is substantially cylindrical, as it can sit on top of the cylindrical bottom portion of the piston. In one example, the piston weight is made of copper or copper alloy. For example, the piston weight can weigh 7.5 gram (FIG. 11A) and 5 gram (FIG. 11B).

Figure 12B:
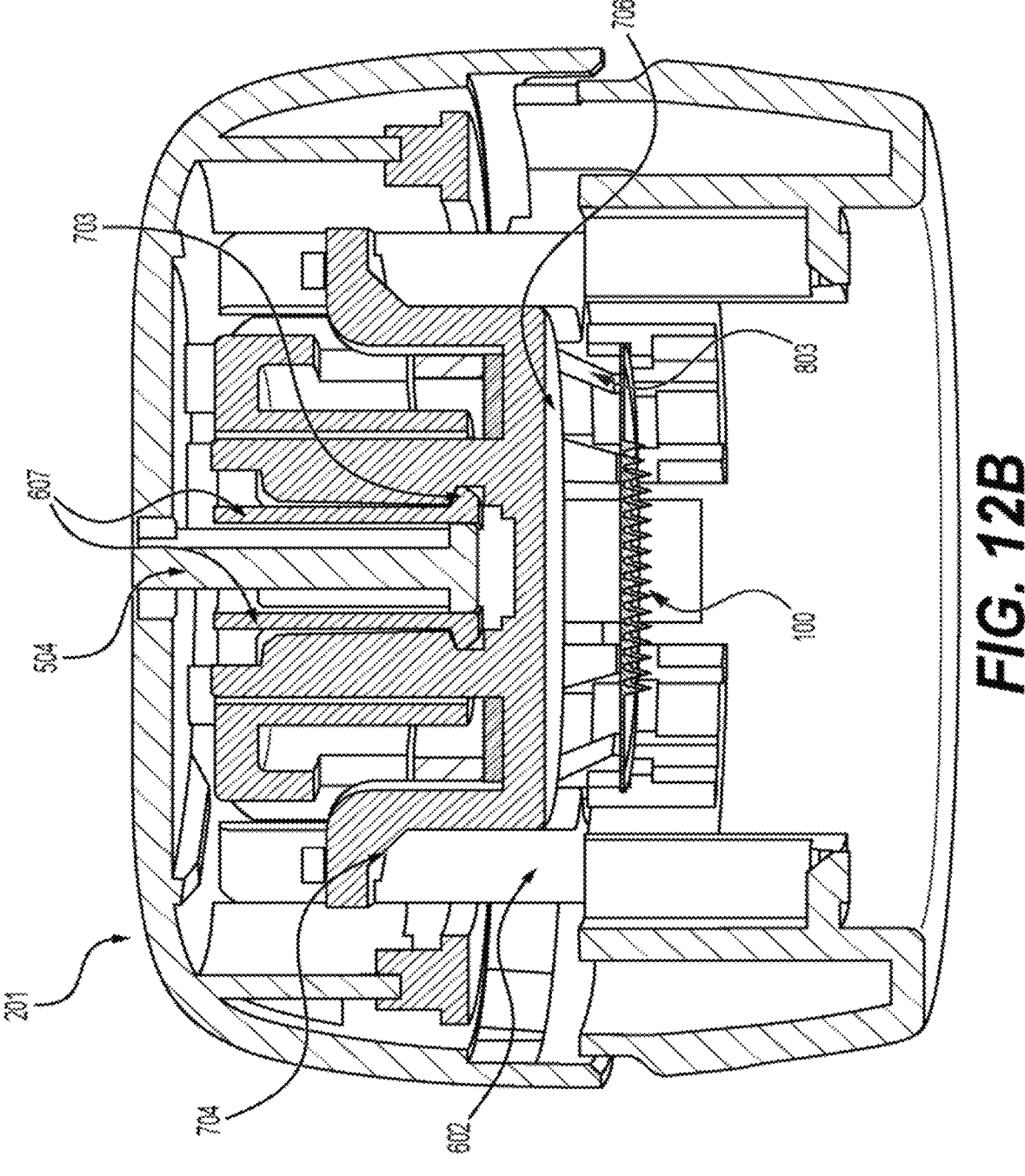

FIGS. 12A and 12B provide more details relating to the connection and configuration of different components of the applicator device. FIGS. 12A and 12B are side cut-away views of the applicator device 200 at different angles. The components of the applicator device, e.g., the top portion, the middle portion, the piston portion, and the bottom portion, can be connected to one another using a number of connection mechanisms.

For example, as shown in FIG. 12A, the protrusions of the one or more beams 505 of the top portion latch onto the edge 604 of the inner circle of the middle portion, securing the top portion to the middle portion. In addition, the protrusions of the one or more beams 606 of the middle portion latch onto the protrusions of one or more beams 804 of the bottom portion, securing the middle portion to the bottom portion. Furthermore, the one or more first flexure interfaces 503 of the top portion sits on the one or more ratchets 605 of the middle portion, increasing the resistance of the top portion from moving downwards. Additionally, as shown in FIG.

12B, the middle beam 504 of the top portion holds the one or more beams 607 of the middle portion in the one or more grooves 703 of the piston portion when the applicator device 200 is in locked state. In this example, the middle beam 504 of the top portion has a protrusion on the top of the beam and the protrusion pushes the protrusions of the one or more beams 607 of the middle portion in the one or more grooves 703 of the piston portion. When the applicator device is activated, the protrusion of the middle beam 504 moves downwards, thereby releasing the one or more beams 607 from the one or more grooves 703. Thus, the piston portion is released from the top portion and the middle portion and move downwards. Furthermore, the bottom face 706 of the piston portion pushes the one or more ramps 803 of the patch holder 801 outwards, releasing the medicament patch 100 from the applicator device.

Figures 13A, 13B, 13C:
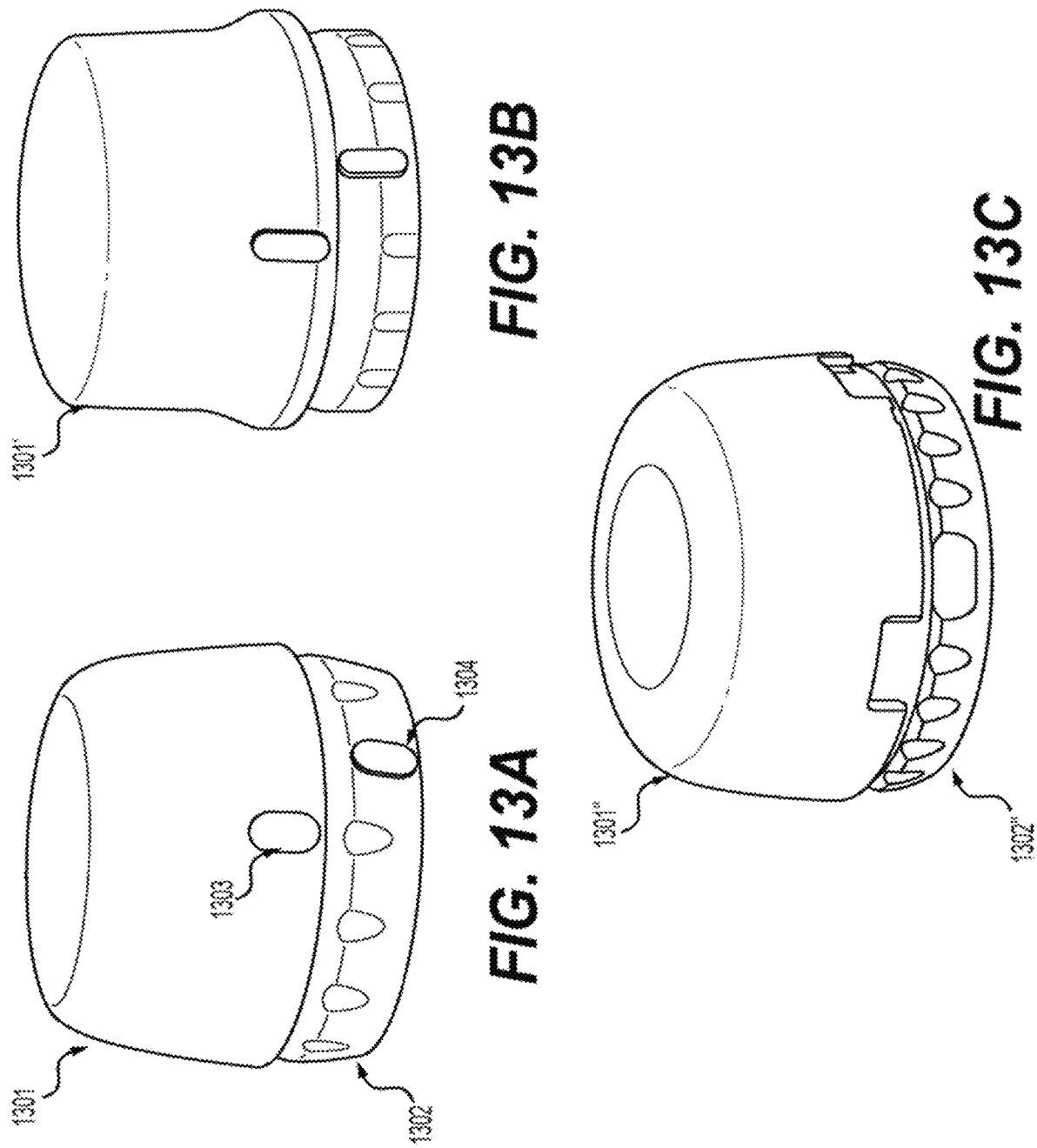
FIGS. 13A-13C are alternative exemplary embodiments of applicator devices.

Furthermore, the applicator device can have a variety of shapes and designs for easy grip of the user and reliable application of the patch onto a patient. For example, FIGS. 13A and 13C are alternative exemplary embodiments of the applicator device. In the examples depicted in FIGS. 13A, the top portion 1301 includes a protrusion-style indicator 1303 and the bottom portion 1302 also includes a protrusion-style indicator 1304. In this example, the application device is unlocked when the indicator 1303 is aligned with the indicator 1304. In this example, the top portion 1301 is substantially cylindrical. In the example depicted in FIG. 13B, the top portion 1301' is substantially cylindrical with a flared bottom. In other embodiments, the size of the top portion or the bottom portion may be adjusted to make it easier for the user to use the applicator device. As an example, the bottom portion of the applicator device may be shorter so the user is more likely to hold the top portion when using the applicator, which may facilitate the application of the device. For example as shown in FIG. 13C, the bottom portion 1302 is shorter. In one example, the bottom portion 1302 may be shorter by up to 6 mm.

Figures 14A, 14B, 14C:
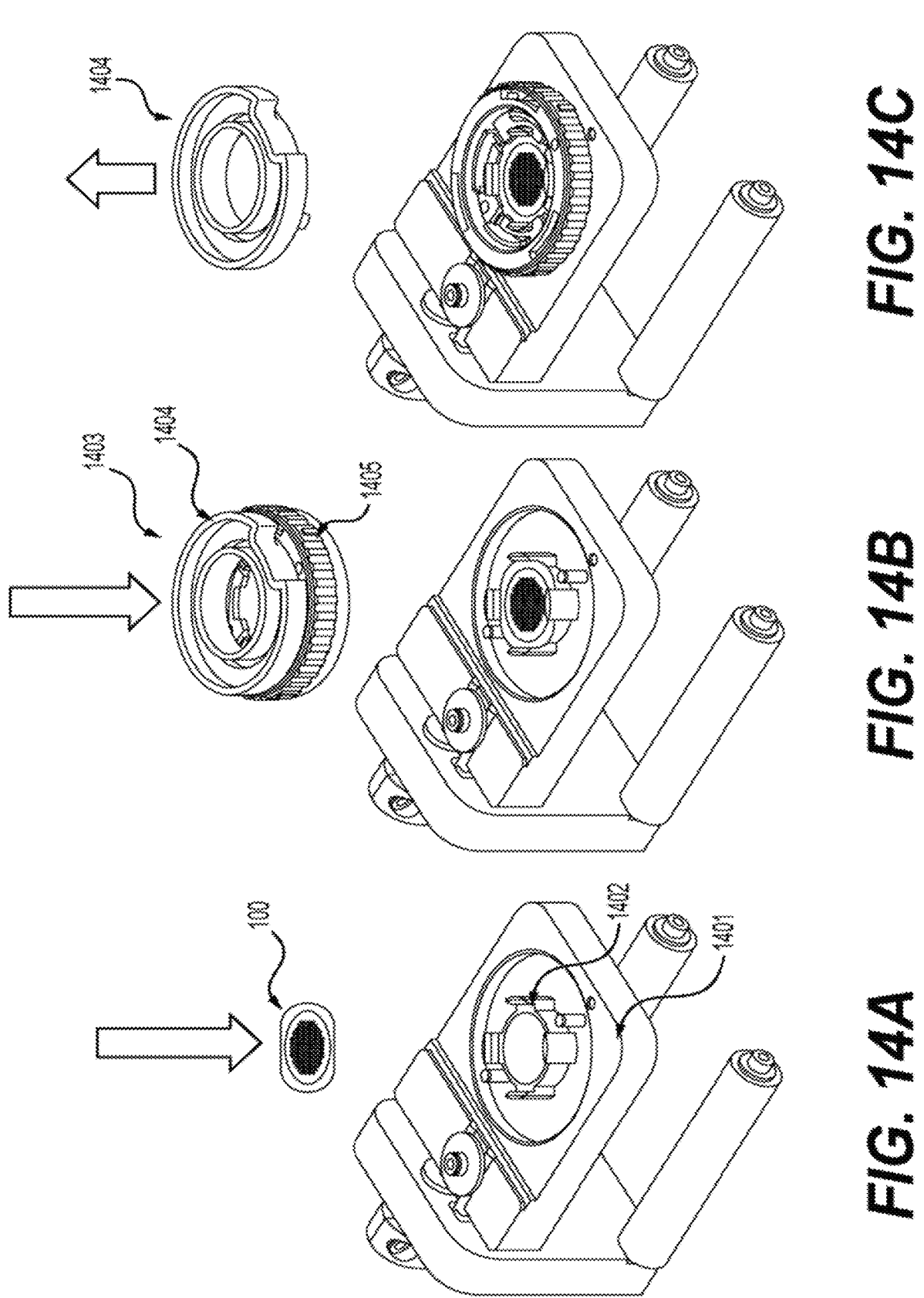
FIGS. 14A-14E illustrate steps in part of a process of assembling an applicator device, according to exemplary embodiments.
Figures 14D, 14E:
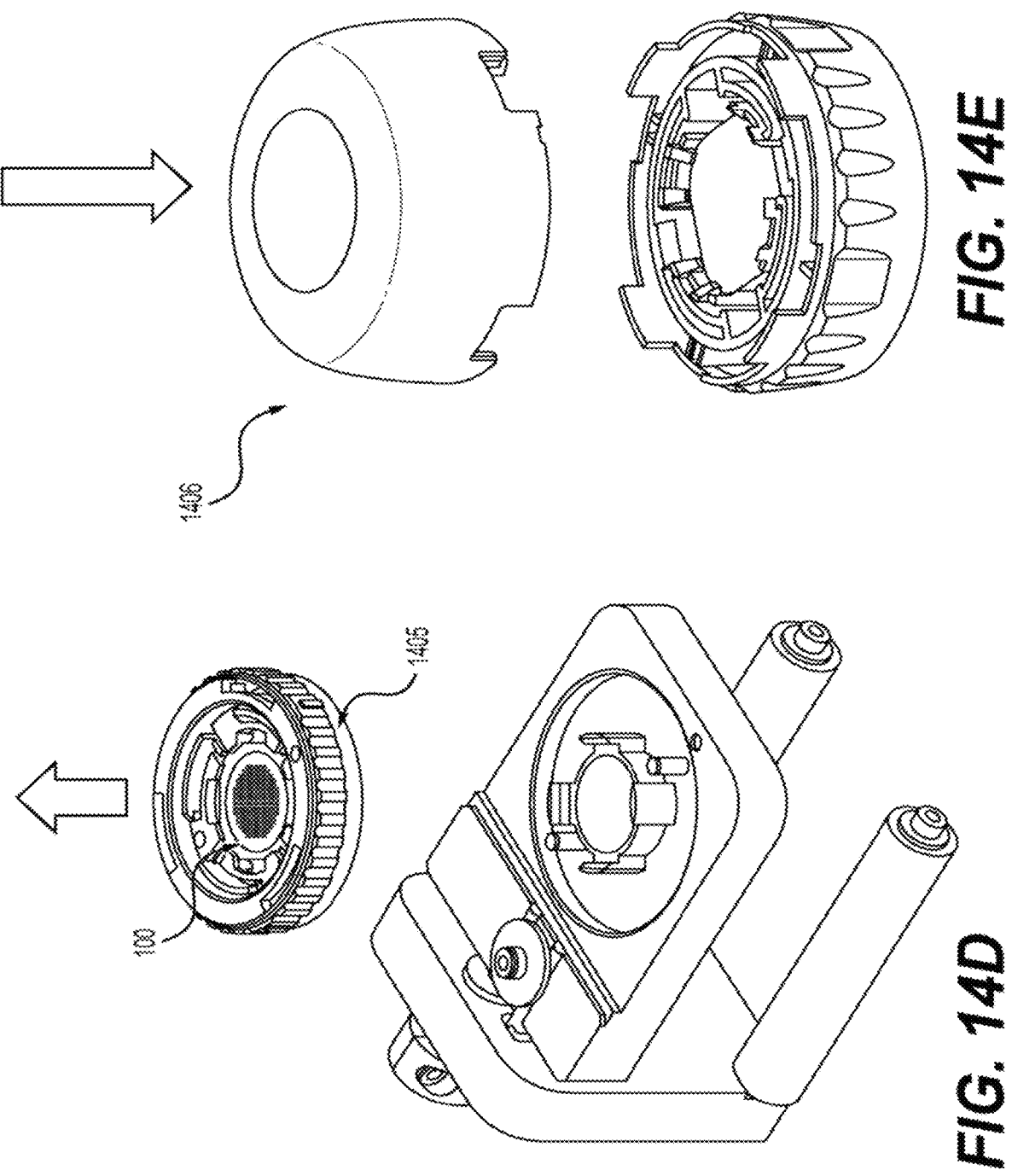

FIGS. 14A-14E illustrate the process of assembling an applicator device 200. First, a medicament patch 100 is installed onto an inspection fixture 1401 to sit a stage 1402 (FIG. 14A). Next, a cartridge 1403, which contains a locking/unlocking fixture 1404 and a bottom portion 1405, onto the inspection fixture 1401. In this process, the patch 100 is held by a patch holder of the inspection fixture 1401 (FIG. 14B). Next, the locking fixture 1404 is rotated, flexing the holding features of the bottom portion 1405 which the mounts the patch 100 onto the bottom portion. Further rotation of the locking/unlocking fixture 1404 causes the holding features of the bottom portion 1405 to return to their original configuration, locking the patch 100 onto the bottom portion 1405. The locking/unlocking fixture 1404 is then removed from the inspection fixture 1401 (FIG. 14C). Then, the bottom portion 1405 with the medicament patch 100 is removed from the inspection fixture 1401 (FIG. 14D).

Next, an inner core assembly, which contains a middle portion, a compressible member, a piston portion, and a top portion is loaded onto of the bottom portion 1405. The inner core can be connected to the bottom portion through a number of connection mechanisms. In one example, the inner core assembly is connected to the bottom portion with the middle portion snap-connected to the bottom portion (not shown). (FIG. 12E).

FIG. 15 is an image showing a user holding an applicator device. The shape and size of the top portion 1501 and the bottom portion 1502 may be designed for easy grip when twisting the top portion and to encourage the user to hold the sidewall of the top portion when using the applicator. In one embodiment, as illustrated in FIG. 15, the bottom portion has one or more indentations 1501, making it easier to twist the top portion 1501 of the device to unlock the device. In addition, the bottom portion 1502 is shorter than the top portion 1501, so the user is more likely to hold the top portion when pressing the device against a patient's skin and applying the patch to the patient's skin.

Figure 16:
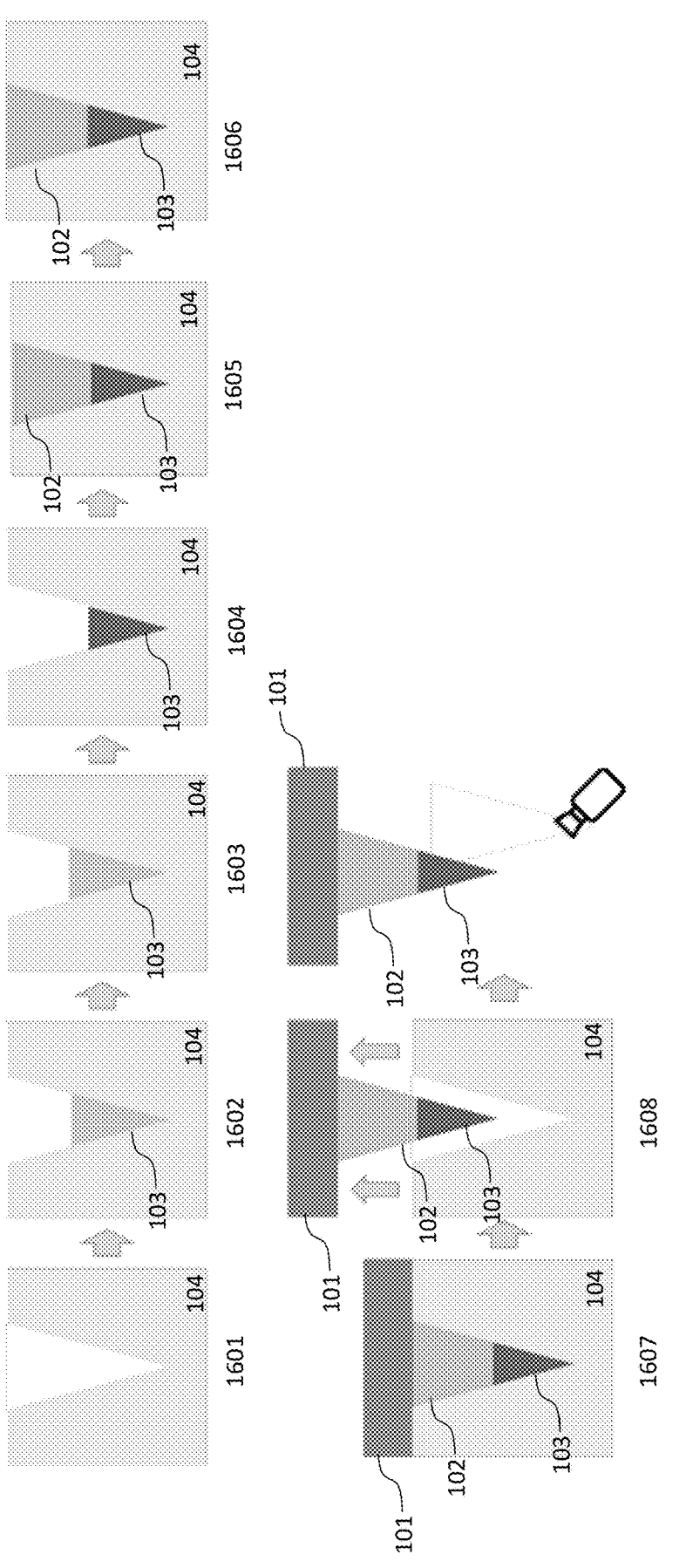
FIG. 16 illustrates a manufacturing process according to some embodiments of the present disclosure.

FIG. 16 illustrates a manufacturing process according to some embodiments of the present disclosure. Additional details with respect to and parameters of the manufacturing process are discussed in relation to FIG. 18. At 1601, a mold 104 is provided that includes one or more microneedle cavities. In some embodiments, the mold 104 can be formed by liquid silicone injection molding. It is important to note that, while a single microneedle cavity is shown in 1601, the mold 104 may comprise a plurality of microneedle cavities arranged in an array. At 1602, the microneedle cavity within the mold 104 is filled with a print solution, such as via nanoliter printing. The print solution eventually can form the tip 103. At 1603, the print solution can be inspected to ensure sufficient filling was performed. At 1604, the print solution can be dried such that it forms the tip 103. At 1605, the rest of the microneedle cavity is filled with base solution on top of the dried tip 103. At 1606, the base solution is dried. At 1607, the backing 101 is applied to the top of the mold such that it contacts the mold 104 and the base 102. At 1608, demolding can be performed to separate the backing 101, base 102, and tip 103 from the mold 104, and the demolded MAP can then be inspected.

Figure 17:
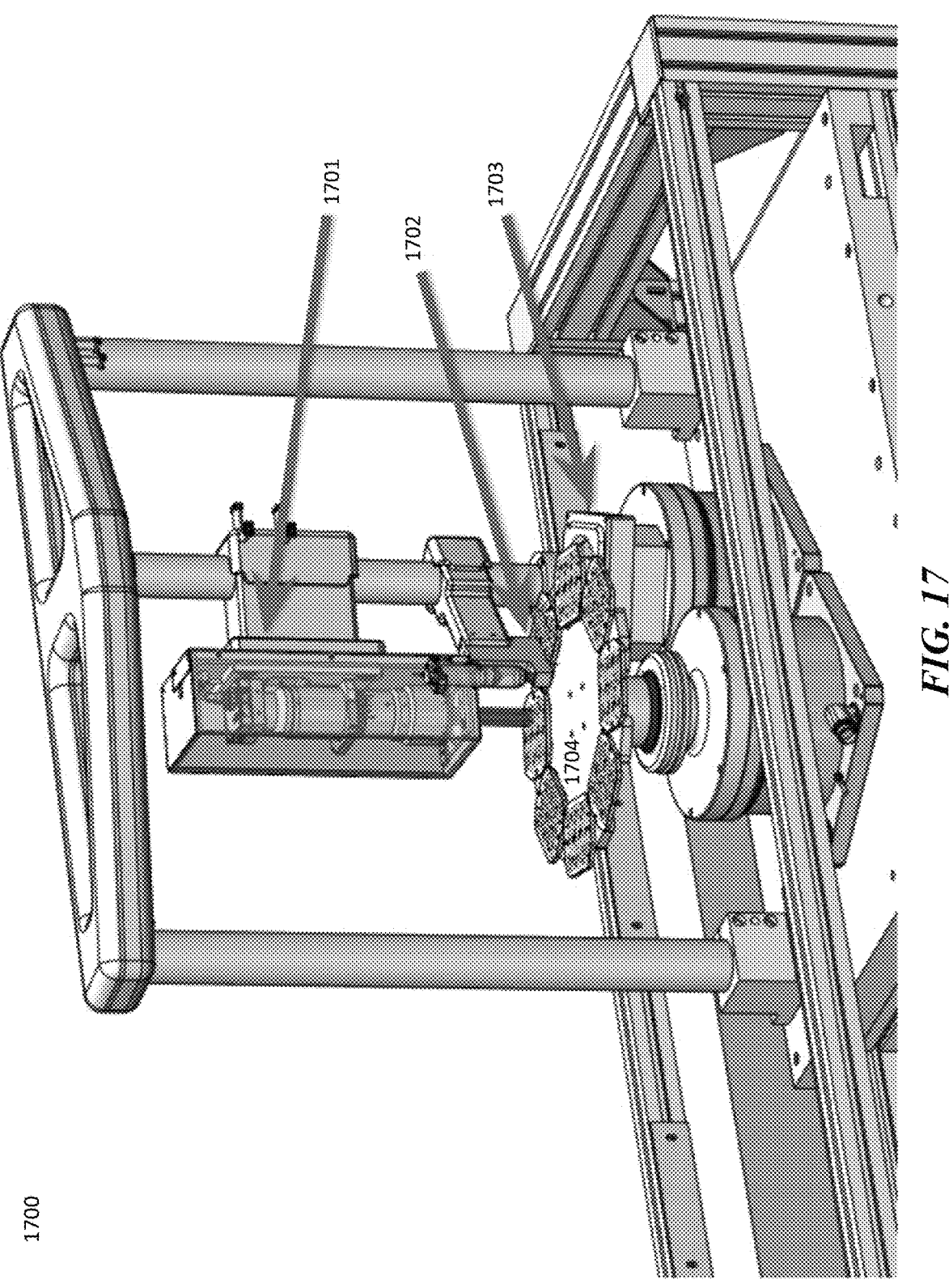
FIG. 17 illustrates an example machine-vision-guided dispensing cell according to some embodiments of the present disclosure.

FIG. 17 illustrates an example machine-vision-guided dispensing cell 1700 according to some embodiments of the present disclosure. In some embodiments, the dispensing cell 1700 can include a camera 1701, a dispenser 1702, and a backlight 1703. The dispensing cell 1700 can be configured to dispense various array subsets or layouts of microneedles within molds 1704. In some embodiments, the dispensing cell 1700 can include a piezo-actuated jetting valve and a high energy jet dispenser to enable filling of viscous formulations fully into a tip of the microneedle cavity.

FIG. 18 is a flowchart for a manufacturing process 1800 according to some embodiments of the present disclosure. At block 1801, the process 1800 can include dispensing a print solution into a plurality of microneedle cavities within a mold (e.g., mold 104). In some embodiments, the plurality of microneedle cavities can be arranged in an array within the mold. In some embodiments, dispensing the print solution into each microneedle cavity of the array of microneedle cavities can include dispensing a volume of about 20 or 30 nL. The print solution can include the API that will ultimately be delivered to a subject. In some embodiments, dispensing the print solution into each microneedle cavity of the array of microneedle cavities can include dispensing the print solution via machine vision guided printing, such as via the machine-vision-guided dispensing cell 1700 of FIG. 17.

At block 1802, the process 1800 can include drying the print solutions within the various microneedle cavities of the mold to form tips (e.g., tips 103). In some embodiments, the drying of the dispensed print solution can be performed in a drying environment with a humidity of at least about 50%. In some embodiments, it can be desirable to lengthen the drying time of the dispensed print solution, and higher humidity levels can contribute to this lengthening. As the drying time increases, more of the print solution consolidates into the bottom of the microneedle cavity, which increases the overall consolidation of and decreases the total length of the resulting tip 103. Additional details related to drying and tip consolidation are discussed in relation to FIGS. 20 and 21.

At block 1803, the process 1800 can include dispensing a base solution into the microneedle cavities. The base solution can be dispensed onto the top of the dried print solution (i.e., the tip 103) to form a base for each of the microneedles. In some embodiments, dispensing the base solution into each microneedle cavity of the array of microneedle cavities can include dispensing a volume of about 85 nL+/−10%.

At block 1804, the process 1800 can include drying the base solution to form the base 102 in each of the plurality of microneedle cavities. In other words, a base 102 will therefore be formed on top of each of the tips 103. In some embodiments, the drying of the dispensed base solution can be performed in a drying environment with a humidity of at least about 50%.

At block 1805, the process 1800 can include applying a backing 101 to the bases 102 and the mold 104. In some embodiments, the backing 101 can be applied by pressing the backing 101 down onto the mold 104 and bases 102 such that an adhesive layer causes the components to stick together. In some embodiments, applying the backing 101 to the array of bases 102 and the mold 104 can include pressing the backing 101 with a force of about 60 psig.

At block 1806, the process 1800 can include demolding the microneedle mold 104 from the backing 101 such that only the bases 102 and their associated tips 103 are adhered to the backing 101.

FIG. 19 is another flowchart for a manufacturing process 1900 according to some embodiments of the present disclosure. While 1900 is discussed in relation to the print solution, the method can also be applied to the base solution. In some embodiments, process 1900 can be a method of progressive filling that has various benefits and both the print solution and the base solution can be progressively inserted into the various microneedle cavities of the mold 104. Such benefits can include the prevention of tip dislodgement and yield improvement. Process 1900 can therefore be performed at one or more of blocks 1801 and 1803 of FIG. 18.

At block 1901, the process 1900 can include dispensing a first volume of print solution into a plurality of microneedle cavities within a mold (e.g., mold 104). In some embodiments, similar to above, the plurality of microneedle cavities can be arranged in an array within the mold. The first volume of print solution can include the API that will ultimately be delivered to a subject. In some embodiments, dispensing the first volume of print solution into each microneedle cavity of the array of microneedle cavities can include dispensing the print solution via machine vision guided printing, such as via the machine-vision-guided dispensing cell 1700 of FIG. 17.

At block 1902, the process 1900 can include drying the first volume of print solution to form a first portion of the tips 103. In some embodiments, similar to the steps discussed above, the drying of the dispensed first volume of print solution can be performed in a drying environment with a humidity of at least about 50%.

At block 1903, once the first volume of print solution is dried, the process 1900 can include dispensing a second volume of print solution into the plurality of microneedle cavities within the mold 104. The second volume of print solution can be dispensed on top of the first volume of print solution in a similar manner to how the first volume was dispensed. At block 1904, the process 1900 can include drying the second volume of print solution to form a second portion of the tips 103. In some embodiments, similar to the steps discussed above, the drying of the dispensed first volume of print solution can be performed in a drying environment with a humidity of at least about 50%. Once dried, the first and second portions of the tips 103 can therefore form the full tips 103.

FIG. 20 is a visualization of tip morphology according to some embodiments of the present disclosure. As discussed above in relation to FIG. 18, it can be desirable to lengthen the drying time of the dispensed print solution. As the drying time increases, more of the print solution consolidates into the bottom of the microneedle cavity, which increases the overall consolidation of and decreases the total length of the resulting tip 103, allowing for more optimal delivery of the API to the subject. The right-hand side of FIG. 20 illustrates a mold with a dried tip 103 that is consolidated. This means that the tip 103 is most effectively deployed as it is likely that the entire tip 103 will be deployed at the proper depth and a high percentage of the API will be delivered to the subject. The left-hand side of FIG. 20 illustrates an exaggerated version of an initial fill of the print solution into a microneedle cavity. There are contact lines 2000*a-b* which are the tops of the liquid solution within the cavity. The middle of FIG. 20 illustrates an undesirable morphology of the tip 103 as it is a shell; the API is therefore spread over a larger area and it is likely only a low percentage will be delivered to the subject.

Figure 21:
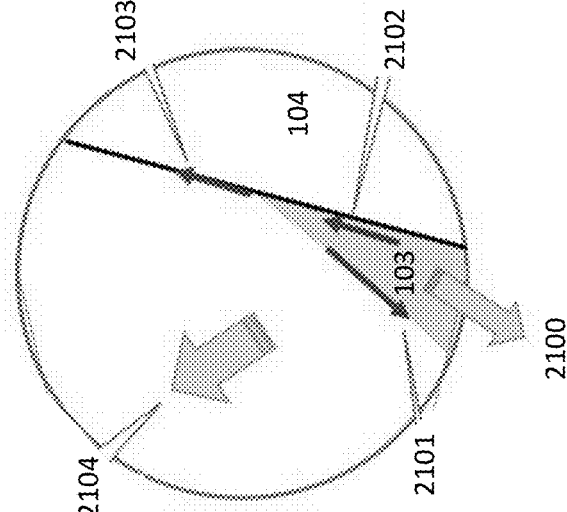
FIG. 21 is another visualization of tip morphology according to some embodiments of the present disclosure.

FIG. 21 is another visualization of tip morphology according to some embodiments of the present disclosure. FIG. 21 is a zoomed-in view of a contact line 2000*b* from FIG. 20 and illustrates the various forces at play affecting the consolidation of the tip 103 during the drying process. First, there is a colloidal diffusion force 2100 (i.e., fluid flow) in a downwards direction along the inner surface of the microneedle cavity. Second, there is surface tension (i.e., cohesion) force 2101 acting in the downwards direction. Third, there is a viscous force 2102 acting in the upwards direction. Fourth, there is an interfacial tension force (i.e., adhesion) 2103 in the upwards direction along the inner surface of the microneedle cavity. Fifth, there is the force of evaporation 2104 acting in an upwards direction (but not necessarily directly along the inner surface of the microneedle cavity). It is desirable for the contact line 2000*b* to recede downwards before the print solution is fully dried, so a slower drying process is desirable.

Detailed Examples of Exemplary Patches

As discussed above, the applicator can be used to apply numerous types of medicament patches but may be particularly desirable for application of microneedle devices. Accordingly, suitable patches including microneedles are described in more detail below. It is contemplated that the applicator and/or ring holder or sub-components may be provided as a kit or system including an applicator and patch, a patch and ring holder, or an applicator with one or multiple patches to be used with a reusable applicator. Some examples of suitable microneedles devices are further described in PCT Patent Application PCT/US2011/056856, titled "Silk fibroin-based microneedles and methods of making the same," which was filed Oct. 19, 2011; PCT Patent Application PCT/US2019/025467, titled "Microneedle comprising silk fibroin applied to a dissolvable base," which was filed Apr. 2, 2019; PCT Patent Application PCT/US2020/055139, titled "Silk Fibroin-Based Microneedles and Uses Thereof," which was filed Oct. 9, 2020; PCT application PCT/US2021/033776, titled, "Compositions and devices for vaccine release and uses thereof," which was filed May 21, 2021; PCT/US2022/030177, titled "Microneedle Vaccine Against Severe Acute Respiratory Syndrome Coronavirus 2 (SARS-COV-2)," which was filed May 20, 2022, each of which is herein incorporated by reference in their entirety. Some examples of suitable microneedle and microneedle devices can be characterized by tips comprising a polymer selected from the group consisting of silk fibroin, copovidone (e.g., copovidone K25-31 or Kollidon VA 64), polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, PLA-PGA, polyorthoester, polycaprolactone, polyfumarate, chitosan, alginate, hyaluronic acid and other biocompatible and/or biodegradable polymers.

Moreover, some examples of suitable patches may preferably include silk fibroin-based microneedles and microneedle devices (e.g., microneedle arrays and patches) for the administration, transport, and release, e.g., controlled- or sustained-release, of a therapeutic agent, such as a vaccine, an antigen, and/or an immunogen (e.g., an influenza vaccine and/or a coronavirus vaccine, e.g., an mRNA-based vaccine) across a biological barrier, such as the skin, a mucous membrane, a buccal cavity, a tissue, or a cell membrane.

The term "administration" or "administering" includes routes of introducing a therapeutic agent to a subject to perform their intended function. In certain embodiments, the administration of the therapeutic agent, such as by a microneedle or microneedle device as described herein, may be repeated and the administrations may be separated by at least about 1 day, 2 days, 3 days, 5 days, 10 days, 15 days, 30 days, 45 days, 3 weeks, 4 weeks, 5 weeks, 6 weeks, 12 weeks, 2 months, 75 days, 3 months, or at least 6 months. In other embodiments, the administration of the therapeutic agent, such as by a microneedle or microneedle device as described herein, may be repeated annually. In other embodiments, the administration of the therapeutic agent, such as by a microneedle or microneedle device as described herein, may be repeated as often as necessary to achieve a therapeutic or prophylactic effect. Administration "in combination with" one or more further therapeutic agents includes simultaneous (concurrent) and consecutive administration in any order.

As used herein, a "subject" refers to a human or animal. Usually the animal is a vertebrate such as a primate, rodent, domestic animal, or game animal. Primates include chimpanzees, cynomolgus monkeys, spider monkeys, and macaques (e.g., Rhesus). Rodents include mice, rats, woodchucks, ferrets, rabbits and hamsters. Domestic and game animals include cows, horses, pigs, deer, bison, buffalo, feline species (e.g., domestic cat), canine species (e.g., dog, fox, wolf), avian species (e.g., chicken, emu, ostrich), and fish (e.g., trout, catfish and salmon). In certain embodiments of the aspects described herein, the subject is a mammal (e.g., a primate, e.g., a human). A subject can be male or female. In certain embodiments, the subject is a mammal. The mammal can be a human, non-human primate, mouse, rat, dog, cat, horse, or cow, but are not limited to these examples. In addition, the methods and formulations described herein can be used to treat domesticated animals and/or pets. In some embodiments, the term "subject" is intended to include living organisms in which an immune response can be elicited (for example, mammals, for example, human).

In a particular embodiment, the subject is a human. A subject may be of any age. In an embodiment, the subject is an elderly human subject, e.g., 65 years of age or older. In an embodiment, a subject is a human subject who is not an elderly, e.g., less than 65 years of age. In an embodiment, a subject is a human pediatric subject, e.g., 18 years of age or less. In an embodiment, a subject is an adult subject, e.g., older than 18 years of age.

As used herein, the term "antigen" refers to refers to a molecule (e.g., a gene product (e.g., protein or peptide), pathogen fragment, whole pathogen, viral vector, or viral particle) capable of inducing a humoral immune response and/or cellular immune response, e.g., leading to the activation of B and/or T lymphocytes and/or innate immune cells and/or antigen presenting cells. Any macromolecule, including proteins or peptides, can be an antigen. Antigens can also be derived from genomic and/or recombinant DNA. For example, any DNA comprising a nucleotide sequence or a partial nucleotide sequence that encodes a protein capable of eliciting an immune response encodes an "antigen." In some embodiments, an antigen does not need to be encoded solely by a full length nucleotide sequence of a gene, nor does an antigen need to be encoded by a gene at all. In some embodiments, an antigen can be synthesized or can be derived from a biological sample, e.g., a tissue sample, a tumor sample, a cell, or a fluid with other biological components. In some embodiments, an antigen can be derived from a virus, e.g., an inactivated virus, a viral like particle, or a viral vector. Antigens as used herein may also be mixtures of several individual antigens.

As used herein, the term "immunogen" refers to any substance (e.g., an antigen, combination of antigens, pathogen fragment, whole pathogen) capable of eliciting an immune response in an organism. An "immunogen" is capable of inducing an immunological response against itself after administration to a mammalian subject. The term "immunological" as used herein with respect to an immunological response, refers to the development of a humoral (antibody mediated) and/or a cellular (mediated by antigen-specific T cells or their secretion products) response directed against an immunogen in a recipient subject. Such a response can be an active response induced by administration of an immunogen or immunogenic peptide to a subject or a passive response induced by administration of antibody or primed T cells that are directed towards the immunogen. In some embodiments, an immunogen is a coronavirus antigen. In some embodiments, an immunogen is a coronavirus. In some embodiments, an immunogen is an influenza virus. In some embodiments, an immunogen is a viral vaccine (e.g., a monovalent (also called univalent) or a multivalent (also called polyvalent) vaccine, such as for coronavirus and/or influenza). In some embodiments, the vaccine (e.g., coronavirus vaccine and/or influenza vaccine) may be monovalent, bivalent, trivalent, quadrivalent (also called tetravalent), or pentavalent. In some embodiments, the immunogen is a replicating or non-replicating vaccine vector (e.g., comprises an adenovirus vector, an adeno-associated virus vector, an alpha virus vector, a herpesvirus vector, a measles virus vector, a poxvirus vector, or a vesicular stomatitis virus vector).

As used herein, the term "therapeutic agent" and "active agent" are art-recognized terms and refers to any chemical moiety that is a biologically, physiologically, or pharmacologically active substance that acts locally or systemically in a subject. Various forms of a therapeutic agent may be used which are capable of being released from the microneedles described herein into adjacent tissues or fluids upon administration to a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness, such as a viral infection; substances which affect the structure or function of the body; or pro-drugs, which become biologically active or more active after they have been placed in a physiological environment.

In certain embodiments, a therapeutic agent comprises, without limitation, a vaccine, an antigen, and/or an immunogen. In certain embodiments, a therapeutic agent comprises a coronavirus vaccine, antigen, and/or immunogen. In certain embodiments, a therapeutic agent comprises an influenza vaccine, antigen, and/or immunogen.

In certain embodiments, a therapeutic agent comprises, without limitation, an amino acid molecule, such as a peptide and/or a protein. In certain embodiments, a therapeutic agent comprises a recombinant protein vaccine.

In certain embodiments, a therapeutic agent comprises, without limitation, a nucleic acid molecule, such as a deoxyribonucleic acid (DNA) molecule and/or a ribonucleic acid (RNA) molecule. In particular embodiments, a therapeutic agent comprises an mRNA. In some embodiments, a therapeutic agent comprises a nucleic acid based vaccine, such as a DNA-based vaccine and/or a RNA-based vaccine. In some embodiments, a therapeutic agent comprises an mRNA-based vaccine.

As used herein, the term "vaccine" refers to any composition that will elicit a protective immune response in a subject that has been exposed to the composition. An immune response may include induction of antibodies and/or induction of a T-cell response. Usually, an "immune response" includes but is not limited to one or more of the following effects: the production or activation of antibodies, B cells, helper T cells, suppressor T cells, and/or cytotoxic T cells, directed specifically to an antigen or antigens included in or derived from the composition or vaccine of interest. Preferably, the subject will display either a therapeutic or a protective immunological (memory) response such that resistance to new infection will be enhanced and/or the clinical severity of the disease reduced. Such protection will be demonstrated by either a reduction in number or severity of, or lack of one or more of the clinical signs associated with the infection of the pathogen, in the delay of onset of viremia, in a reduced viral persistence, in a reduction of the overall viral load and/or in a reduction of viral excretion. In some embodiments, a "vaccine" refers to any preparation of an antigen or an immunogen (including subunit antigens, toxoid antigens, conjugate antigens, or other types of antigenic molecules, or nucleic acid molecules encoding the same) or a killed or live attenuated microorganism that, when introduced into a subject's body, affects the immune response to the specific antigen or microorganism by causing activation of the immune system against the specific antigen or microorganism (e.g., inducing antibody formation, T-cell responses, and/or B-cell responses). Generally, vaccines against microorganisms are directed toward at least part of a virus, bacteria, parasite, mycoplasma, or other infectious agent.

The term "therapeutically effective amount" refers to an amount of the composition as defined herein that is effective for preventing, ameliorating and/or treating a condition resulting from a disease as described herein, such as a viral infection.

The term "treatment" refers to therapeutic treatment as well as prophylactic or preventative measures to cure or halt or at least retard disease progress. Those in need of treatment include those already inflicted with a condition resulting from infection with a virus as described herein as well as those in which infection with a virus is to be prevented. Subjects partially or totally recovered form infection with a virus as described herein might also be in need of treatment. Prevention encompasses inhibiting or reducing the spread of a virus or inhibiting or reducing the onset, development or progression of one or more of the symptoms associated with infection with a virus described herein.

As used herein, the term "viruses" refers to an infectious agent composed of a nucleic acid encapsulated in a protein. Such infectious agents are incapable of autonomous replication (i.e., replication requires the use of the host cell's machinery). Viral genomes can be single-stranded (ss) or double-stranded (ds), RNA or DNA, and can or cannot use reverse transcriptase (RT). Additionally, ssRNA viruses can be either sense (+) or antisense (−). Exemplary viruses include, but are not limited to, dsDNA viruses (e.g., Adenoviruses, Herpesviruses, Poxviruses), ssDNA viruses (e.g., Parvoviruses), dsRNA viruses (e.g., Reo viruses), (+) ssRNA viruses (e.g., Picornaviruses, Toga viruses, Coronaviruses), (−) ssRNA viruses (e.g., Orthomyxoviruses, Rhabdoviruses), ssRNA-RT viruses, i.e., (+) sense RNA with DNA intermediate in life-cycle (e.g., Retroviruses), and dsDNA-RT viruses (e.g., Hepadnaviruses). In some embodiments, viruses can also include wild-type (natural) viruses, killed viruses, live attenuated viruses, modified viruses, recombinant viruses or any combinations thereof Exemplary retroviruses include human immunodeficiency virus (HIV). Other examples of viruses include, but are not limited to, enveloped viruses, respiratory syncytial viruses, non-enveloped viruses (e.g., human papillomavirus (HPV)), bacteriophages, recombinant viruses, and viral vectors. The term "bacteriophages" as used herein refers to viruses that infect bacteria.

As used herein, the term "coronavirus" refers to a positive-sense ssRNA virus within the Coronaviridae family. A coronavirus may be an alphacoronavirus, a betacoronavirus, a gammacoronavirus, or a deltacoronavirus. A coronavirus can be a live wild-type virus, a live attenuated virus, an inactivated virus (e.g., a UV-inactivated virus), a chimeric virus, or a recombinant virus. Coronaviruses are known to infect humans and other animals (e.g., birds and mammals). Examples of coronaviruses include severe acute respiratory syndrome coronavirus (SARS-COV), severe acute respiratory syndrome virus 2 (SARS-COV-2), Middle East respiratory syndrome coronavirus (MERS-COV), human coronavirus 229E (HCoV-229E), human coronavirus NL63 (HCoV-NL63), human coronavirus OC43 (HCoV-OC43), and human coronavirus HKU1 (HCoV-HKU1).

As used herein, the term "influenza virus" refers to a negative-sense ssRNA virus within the Orthomyxoviridae family. An influenza virus can be a live wild-type virus, a live attenuated virus, an inactivated virus, a chimeric virus, or a recombinant virus. Examples of influenza viruses include influenza A, influenza B, influenza C, and influenza D.

The microneedles described herein can be in any shape and/or geometry suitable for use in piercing a biological barrier, e.g., a layer of the skin, to enable release, e.g., controlled or sustained-release, of a vaccine within a subject. Non-limiting examples of the shape and/or geometry of the microneedles include: a cylindrical shape, a wedge-shape, a cone-shape, a pyramid-shape, and/or an irregular-shape, or any combinations thereof.

As used herein, the term "release" and "controlled- or sustained-release" refers to the release of a vaccine, an antigen, and/or an immunogen (e.g., from a microneedle, microneedle device, formulation, composition, article, device, and preparation described herein), such as a coronavirus vaccine, an influenza vaccine, or a combination thereof, over a period of time, e.g., for at least about 1 to about 28 days (e.g., about 1, 2, 3, 4, 5, 6, 7, 8, 9, 10, 11, 12, 13, 14, 15, 16, 17, 18, 19, 20, 21, 22, 23, 24, 25, 26, 27, or 28 or more days, e.g., between about 4 days and about 25 days, between about 10 and about 20 days, between about 10 and about 15 days, between about 12 and about 16 days, e.g., between about 1-2 weeks, about 1-3 weeks, or about 1-4 weeks, e.g., between about 1 month to about 3 months). In some embodiments, the controlled- or sustained-release of a vaccine, such as a coronavirus vaccine and/or an influenza vaccine, over a time period of about 1 to about 14 days, e.g., about 1, 2, 3, 4, 5, 6, 7, 8, 9, 10, 11, 12, 13, or 14 days, by a microneedle, microneedle device, formulation, composition, article, device, or preparation as described herein can result, e.g., in broad spectrum immunity in a subject. In some embodiments, the vaccine formulations and preparations have controlled- or sustained-release properties (e.g., are formulated and/or configured to release a vaccine, e.g., into the skin of the subject, over a period of, or at least 1, 5, 10, 15, 30, 45 minutes; a period of, or at least, 1, 2, 3, 4, 5, 10, 24 hours; a period of, or at least, 1, 2, 3, 4, 5, 6, 7, 8, 9, 10, 11, 12, 13, 14 days; a period of, or at least, 1, 2, 3, 4, 5, 6, 7, 8 weeks; a period of, or at least 1, 2, 3, 4, 5, 6, 7, 8, 9, 10, 11 months; a period of, or at least, 1, 2, 3, 4, 5 years, or longer.

In some embodiments, a microneedle of the invention can comprise the following layers: (1) a backing material; (2) a dissolvable base; and (3) an implantable controlled- or sustained-release tip. For example, the microneedles described herein may include a backing material applied to a dissolvable base layer that supports a distal controlled- or sustained-release implantable tip. In some embodiments, although this is not limiting and is merely exemplary in nature, the tip can include a silk fibroin and vaccine (e.g., an influenza vaccine and/or a coronavirus vaccine, e.g., an mRNA-based vaccine, antigen, and/or immunogen).

As used herein, the term "backing" refers to a material that is suitable for bonding to and/or adhering to a component of a microneedle. In some embodiments, a backing material is suitable for bonding to and/or adhering to the base (e.g., dissolvable base) of a microneedle described herein.

As used herein, the term "base" or "dissolvable base" refers to the layer that forms the base of the microneedles (e.g., functions as the support for the distal microneedle tips that are loaded with a vaccine, antigen, and/or immunogen (e.g., a coronavirus vaccine, an influenza vaccine, or a combination thereof)), and/or can also serve as a layer connecting adjacent microneedles to form a continuous microneedle array or microneedle patch. In some embodiments, at least 10%, 20%, 30%, 40%, 50%, 60%, 70%, 80%, 90% or more of the base is dissolved after application to a biological barrier, e.g., skin, mucous surface, or buccal cavity.

As used interchangeably herein, the terms "sustained-release tip," "implantable sustained-release tip," "implantable microneedle tip," or "releasable tip" refers to the distal end, e.g., tip, of a microneedle capable of piercing a biological barrier, e.g., the skin, mucous surface, or buccal cavity, of a subject and being deposited within the biological barrier, a skin layer (e.g., the dermis). In embodiments, the tip can include a silk fibroin protein or other suitable material in an amount sufficient to sustain the release of a vaccine, e.g., a coronavirus vaccine (e.g., a SARS-CoV-2 vaccine) and/or an influenza vaccine for a prolonged period of time, e.g., for at least about 1 day (e.g., about 1, 2, 3, 4, 5, 6, 7, 8, 9, 10, 11, 12, 13, or 14 or more days, e.g., between about 4 days and about 30 days, 5 days about 25 days, between about 10 days and about 20 days, between about 10 days and about 15 days, between about 4 days and about 14 days, between about 14 days and about 15 days, e.g., between about 1-2 weeks, about 1-3 weeks, or about 1-4 weeks, e.g., about 2-12 months). In some embodiments, the implantable sustained-release tip comprises a coronavirus vaccine, antigen, and/or immunogen. In some embodiments, the implantable sustained-release tip comprises an influenza vaccine, antigen, and/or immunogen.

As used herein, the term "microneedle" refers to a structure having at least two, more typically, three components, e.g., layers, for transport or delivery of a vaccine, an antigen, and/or an immunogen, across a biological barrier, such as the skin, tissue, or cell membrane. In some embodiments, a microneedle comprises a base (e.g., a dissolvable base as described herein), a tip (e.g., an implantable tip as described herein), and optionally, a backing material. In embodiments, a microneedle has dimension of between about 350 μm to about 1500 μm in height (e.g., between about 350 μm to about 1500 μm, e.g., about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1000 μm, about 1050 μm, about 1100 μm, about 1150 μm, about 1200 μm, about 1250 μm, about 1300 μm, about 1350 μm, about 1400 μm, about 1450 μm, about 1500 μm)). In some embodiments, the microneedle is fabricated to have any dimension and/or geometry to enable the deployment of a microneedle tip, e.g., an implantable sustained-release tip, at a depth between about 100 μm and about 900 μm (e.g., at a depth of about 800 μm) into the dermis layer of the skin for release, e.g., controlled- or sustained-release of a vaccine (e.g., a coronavirus vaccine and/or an influenza vaccine).

As used herein, the term "microneedle patch" and "microneedle array" refers to a device comprising a plurality of microneedles, e.g., arranged in a random or predefined pattern, such as an array.

In some embodiments, the length of the microneedle can be between about 350 μm to about 1500 μm (e.g., about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1000 μm, about 0 μm, about 1100 μm, about 1150 μm, about 1200 μm, about 1250 μm, about 1300 μm, about 1350 μm, about 1400 μm, about 1450 μm, about 1500 μm). In embodiments, the length of microneedles can be fabricated sufficiently long enough to enable delivery of an implantable tip comprising a vaccine, an antigen, and/or an immunogen for controlled- or sustained-release, as described herein, to the epidermis (e.g., about 10 μm to 120 μm below the skin surface), e.g., to induce an immune response. In some embodiments, the length of microneedles can be fabricated sufficiently long enough to enable delivery of an implantable tip comprising a vaccine, an antigen, and/or an immunogen for controlled- or sustained-release, as described herein, to the dermis (e.g., about 60 μm to about 2.1 mm below the skin surface). An skilled artisan can adjust the microneedle length for a number of factors, including, without limitations, tissue thickness, e.g., skin thickness, (e.g., as a function of age, gender, location on body, species (e.g., animal), drug delivery profile, diffusion properties of the vaccine, antigen, and/or immunogen for controlled- or sustained-release (e.g., the ionic charge and/or molecule weight, and/or shape of the vaccine, antigen, and/or immunogen for controlled- or sustained-release), or any combinations thereof. However, without wishing to be bound by theory, with an approximately 650 μm tall microneedle an implantable sustained-release tip may be deployed at a depth of between about 100 μm and about 600 μm within the dermis layer of the skin to a subject to achieve controlled- or sustained-release of vaccine from the tip. In some embodiments, the microneedle may be about 800 pm tall (e.g., between about 500 lam and 1200 μm tall).

In some embodiments, a plurality of microneedles can be arranged in a random or predefined pattern to form a microneedle array and/or patch, as described herein. The patch may comprise a carrier, backing, or "handle" layer adhered to the back of the base. This layer can provide structural support and an area by which the patch can be handled and manipulated without disturbing the needle array.

Microneedle Array

The microneedle array may comprise about 121 needles in an 11×11 square grid with approximately 0.75 mm pitch. Individual needles are cones approximately 1.0 mm long with base diameter approximately 0.5 mm and included angle of approximately 30°. The tip of the needle must be sharp in order to penetrate the skin. The radius of curvature of the tip should ideally be no more than 0.01 mm. In some embodiments, microneedle arrays can range from 41 to over 500 needles and can be arranged in either, for example, Backing Exemplary backing materials that can be used in the fabrication of a microneedle of the invention include, but are not limited a solid support, e.g., a paper-based material, a plastic material, a polymeric material, or a polyester-based material (e.g., a Whatman 903 paper, a polymeric tape, a plastic tape, an adhesive-backed polyester tape, or other medical tape). In some embodiments, the backing comprises a Whatman 903 paper. In some embodiments, the backing comprises a polyester tape. In some embodiments, the polyester tape comprises an adhesive-backed polyester tape. In some embodiments, the backing material may be coated (e.g., at least on one side) with an adhesive suitable for bonding to and/or adhering to the dissolvable base of a microneedle described herein.

The backing materials used in the microneedles of the invention may have various properties, including, but not limited to, the ability to bond and/or adhere to the dissolving base layer to permit demolding. A backing material must be strong enough for the backing to maintain patch integrity, e.g., if the dissolving base layer has cracks or discontinuities. The backing material may be sufficiently flexible so as to conform, for example, to a non-flat surface, such as a skin surface. In particular, the backing must be flexible enough during wear time, such as after the patch is applied (e.g., pressed into) the skin. The backing may comprise and/or consist of a non-dissolving material, such that the backing maintains its integrity after patch application to a skin surface and during patch removal from a skin surface.

The backing may have any dimension suitable for application to a target skin surface. In some embodiments, the dimensions of the backing can be a 12 mm diameter circle. In some embodiments, the dimensions of the backing can be a 12 mm wide strip with a "handle" section of up to 12 mm length beyond the edge of the 12 mm×12 mm patch.

Dissolvable Base

In some embodiments, the dissolvable base layer does not comprise, e.g., a detectable amount of, a vaccine, an antigen, and/or an immunogen. In some embodiments, dissolvable base layer is formulated to limit and/or reduce the amount of pharmaceutical, vaccine, antigen, and/or immunogen leakage (e.g., diffusion) from the tips into the dissolvable base layer, e.g., as compared to art known base layer formulations, e.g., base layer formulations comprising PAA. In some embodiments, a limited and/or reduced amount of pharmaceutical, vaccine, antigen, and/or immunogen leakage (e.g., diffusion) from the tips can be determined about 1 day, about 2 days, about 3 days, about 4 days, about 5 days, or about 6 days; about 1 week, about 2 weeks, or about 3 weeks; about 1 month, about 2 months, about 3 months, about 4 months, about 5 months, about 6 months, about 7 months, about 8 months, about 9 months, about 10 months, or about 11 months; or about 1 year or more after fabrication and storage (e.g., storage at about 4° C. (e.g., refrigeration), at about 25° C. (e.g., room temperature), at about 37° C. (e.g., body temperature), at about 45° C. and/or at about 50° C.), e.g., as compared to a base layer formulation comprising PAA.

The dissolvable base layer comprises a material that can dissolve into the skin, e.g., within the intended wear time (e.g., about five minutes). In some embodiments, the at least about 10%, 20%, 30%, 40%, 50%, 60%, 70%, 80%, 90%, or 100% of the dissolvable base layer is dissolved after application, e.g., to the skin, within the intended wear time (e.g., about 1 minute, about 2 minutes, about 3 minutes, about 4 minutes, about 5 minutes, about 6 minutes, about 7 minutes, about 8 minutes, about 9 minutes, or about 10 minutes or more).

The material used in the fabrication of the dissolvable base must be sufficiently strong enough to enable the microneedle to penetrate the skin, and be tough enough (e.g., not brittle) to also enable demolding. The dissolvable base material must be amenable to routine handling without catastrophic failure, and must retain its mechanical properties between demolding and application (e.g., not so hygroscopic that it melts due to ambient humidity). The dissolvable base layer material must be non-toxic and non-reactogenic at the doses used in a patch. In some embodiments, the dissolvable base layer comprises a water soluble component. In some embodiments, a dissolvable base layer, as described herein, has improved biocompatibility, e.g., as compared to a dissolvable base layer comprising poly(acrylic acid) (PAA). In some embodiments, the dissolvable base layer material causes a reduced inflammatory response and/or reduced tissue necrosis. In some embodiments, the dissolvable base layer material is not PAA, and induces a reduced inflammatory response and/or reduced tissue necrosis compared to PAA. In some embodiments, the dissolvable base layer material has a pH similar to that of the biological barrier into which it will be dissolved, e.g., a pH of about 4.0 to about 8.0.

Non-limiting examples of materials that may be used to fabricate the dissolvable base layer include gelatin (e.g., hydrolyzed gelatin), polyethylene glycol (PEG), sucrose, low viscosity carboxymethylcellulose (CMC), polyvinylpyrrolidone (PVP), polyvinyl alcohol (PVA), hyaluronate, maltose, and/or methyl cellulose. In some embodiments, the dissolvable base comprises one, two, three, four, five, six, seven, eight, or more (e.g., all) of gelatin, polyethylene glycol (PEG), sucrose, carboxymethylcellulose (CMC), polyvinylpyrrolidone (PVP), polyvinyl alcohol (PVA), hyaluronate, maltose, and methyl cellulose, e.g., at a concentration between about 1% and about 75% (e.g., about 1%, about 2%, about 3%, about 4%, about 5%, about 6%, about 7%, about 8%, about 9%, about 10%, about 15%, about 20%, about 25%, about 30%, or about 35%, about 40%, about 45%, about 50%, about 55%, about 60%, about 65%, about 70%, or about 75%). In some embodiments, the dissolvable base does not comprise a therapeutic agent, as described herein.

In some embodiments, the dissolvable base comprises between about 10% and about 70% gelatin (e.g., hydrolyzed gelatin) (e.g., about 10%, about 20%, about 30%, about 40%, about 50%, about 60%, or about 70% gelatin).

In some embodiments, the dissolvable base comprises between about 1% and about 70% polyethylene glycol (PEG) (e.g., about 1%, about 2%, about 3%, about 4%, about 5%, about 6%, about 7%, about 8%, about 9%, about 10%, about 20%, about 30%, about 40%, about 50%, about 60%, or about 70% PEG).

In some embodiments, the dissolvable base comprises between about 1% and about 35% sucrose (e.g., about 1%, about 2%, about 3%, about 4%, about 5%, about 6%, about 7%, about 8%, about 9%, about 10%, about 15%, about 20%, about 25%, about 30%, or about 35% sucrose).

In some embodiments, the dissolvable base comprises between about 1% and about 35% CMC (e.g., about 1%, about 2%, about 3%, about 4%, about 5%, about 6%, about 7%, about 8%, about 9%, about 10%, about 15%, about 20%, about 25%, about 30%, or about 35% CMC).

In some embodiments, the dissolvable base comprises between about 10% and about 70% PVP (e.g., about 10%, about 20%, about 30%, about 40%, about 50%, about 60%, or about 70% PVP).

In some embodiments, the dissolvable base comprises between about 1% and about 35% PVA (e.g., e.g., about 1%, about 2%, about 3%, about 4%, about 5%, about 6%, about 7%, about 8%, about 9%, about 10%, about 15%, about 20%, about 25%, about 30%, or about 35% PVA).

In some embodiments, the dissolvable base comprises between about 1% and about 75% (e.g., about 1%, about 2%, about 3%, about 4%, about 5%, about 6%, about 7%, about 8%, about 9%, about 10%, about 15%, about 20%, about 25%, about 30%, or about 35%, about 40%, about 45%, about 50%, about 55%, about 60%, about 65%, about 70%, or about 75% hyaluronate).

In some embodiments, the dissolvable base comprises between about 1% and about 75% (e.g., about 1%, about 2%, about 3%, about 4%, about 5%, about 6%, about 7%, about 8%, about 9%, about 10%, about 15%, about 20%, about 25%, about 30%, or about 35%, about 40%, about 45%, about 50%, about 55%, about 60%, about 65%, about 70%, or about 75% maltose).

In some embodiments, the dissolvable base comprises between about 1% and about 75% (e.g., about 1%, about 2%, about 3%, about 4%, about 5%, about 6%, about 7%, about 8%, about 9%, about 10%, about 15%, about 20%, about 25%, about 30%, or about 35%, about 40%, about 45%, about 50%, about 55%, about 60%, about 65%, about 70%, or about 75% methyl cellulose).

In some embodiments, the dissolvable base layer may comprise 40% hydrolyzed gelatin, 10% Sucrose w/v in DI water. Optionally, the base layer may include 1% low viscosity carboxymethylcellulose (CMC), which may reduce brittleness. In some embodiments, the dissolvable base layer may comprise polyvinylpyrrolidone (PVP) of 101 (13 MW at up to 50% w/v in DI water; polyvinyl alcohol (PVA) 87% hydrolyzed at 13 1 (13 MW at up to 20% in DI water; or CMC at up to 10% in DI water. The following combinations may also be suitable for use in the fabrication of a dissolvable base layer: 30% PVP and 10% PVA; 37% PVP, 5% PVA, and 15% sucrose; or various other proportions of PVP, PVA, and sucrose.

In some embodiments, the dissolvable base layer is approximately 12 mm square and 0.75 mm thick. In some embodiments, the dissolvable base layer can cover the entire patch. In some embodiments, the dimension of the base layer can be a 12 mm diameter circle, or a 12×12 mm square.

Implantable Sustained-Release Tip

In embodiments, the implantable sustained-release tip can be fabricated from silk fibroin and may comprise a pharmaceutical, vaccine, an antigen, and/or an immunogen as described herein (e.g., an influenza vaccine and/or a coronavirus vaccine, e.g., an mRNA-based vaccine). In some embodiments, the implantable sustained-release tip can be designed to be deployed into the dermis layer of the skin (e.g., not into the subcutaneous space), as the population of professional antigen presenting cells in the dermis is much higher than in the subcutaneous space. In humans, the dermis ranges from about 1000-2000 µm (e.g., about 1-2 mm) thick based on location and patient age and health. In rodents, the dermis is much thinner (e.g., mice-100-300 µm, and rats-800-1200 µm). Without wishing to be bound by theory, with a 650 µm tall microneedle an implantable sustained-release tip may be deployed at a depth of between about 100 µm and about 600 µm to achieve the controlled- or sustained-release of a vaccine, an antigen, and/or an immunogen as described herein (e.g., an influenza vaccine and/or a coronavirus vaccine, e.g., an mRNA-based vaccine).

Without being bound by theory, the molecular weight of the silk fibroin solution used in the fabrication of a microneedle described herein can function as a control factor to modulate the controlled- or sustained-release of a vaccine, an antigen, and/or an immunogen (e.g., an influenza vaccine and/or a coronavirus vaccine, e.g., an mRNA-based vaccine) from the tip. In some embodiments, a higher molecular weight silk fibroin solutions can favor a slower controlled- or sustained-release (e.g., reducing the amount of an initial burst (e.g., the amount released on Day 0) by at least about 10% and then releasing additional antigen over at least about the next 4 days). In some embodiments, the controlled- or sustained-release of a vaccine, an antigen, and/or an immunogen (e.g., an influenza vaccine and/or a coronavirus vaccine, e.g., an mRNA-based vaccine) from the tip may be over at least about 4 days (e.g., about 4, 5, 6, 7, 8, 9, 10, 11, 12, 13, or 14 or more days, e.g., between about 4 days and about 14 days, e.g., between about 1-2 weeks, about 1-3 weeks, or about 1-4 weeks). In some embodiments, controlled- or sustained-release occurs over about 1 week to about 2 weeks.

Without being bound by theory, the primary tunability of the implantable sustained-release tip is its crystallinity, measured via beta-sheet content (intermolecular and intramolecular 3-sheet). This impacts the solubility of the tip matrix and the ability of antigen to be retained. With the increased (3-sheet content, the tip also becomes more mechanically strong. Specific vaccine release profiles are achieved through modulation of the crystallinity and the diffusivity of the matrix. This is accomplished through the input material and formulation as well as post-treatment to increase crystallinity (e.g. water annealing, methanol/solvent annealing). In some embodiments, the implantable controlled- or sustained-release microneedle tip comprises a beta-sheet content of between about 10% and about 60% (e.g., about 10%, about 20%, about 30%, about 40%, about 50%, about 60%), e.g., as based on a "crystallinity index," e.g., a "crystallinity index" known in the art. In some embodiments, the implantable controlled- or sustained-release microneedle tip can be formulated as a particle (e.g., a microparticle and/or a nanoparticle).

Dimensions of the Implantable Sustained-Release Tip

The methods provided herein can be used to fabricate implantable sustained-release tips of any dimensions, e.g., ranging from about 75 µm to about 800 µm in height/length (e.g., about 75, about 100 µm, about 125 µm, about 150 µm, about 250 µm to about 300 µm, about 300 µm to about 350 µm, about 350 µm to about 400 µm, about 400 µm to about 450 µm, about 450 µm to about 500 µm, about 500 µm to about 550 µm, about 550 µm to about 600 µm, about 600 µm to about 650 µm, about 650 µm to about 700 µm, about 700 µm to about 750 µm, about 750 µm, to about 800 µm), and/or having a tip radius of about 10 µm or less (e.g., between about 1 µm and about 10 µm, e.g., about 1 µm or less, about 2 µm or less, about 3 µm or less, about 4 µm or less, about 5 µm or less, about 6 µm or less, about 7 µm or less, about 8 µm or less, about 9 µm or less, or about 10 µm or less). In some embodiments, the implantable tip can have a diameter of any size, e.g., based upon the type of biological barrier (e.g., skin layer) intended to be pierced by the tip. In embodiments, the tip can have a dimension (e.g., a diameter) ranging from about 50 nm to about 50 µm (e.g., about 50 nm to about 250 nm, about 250 nm to about 500 nm, about 500 to about 750 nm, about 750 nm to about 1 µm, about 1 µm to about 5 µm, about 5 µm to about 10 µm, about 10 µm to about 15 µm, about 15 µm to about 20 µm, about 20 µm to about 25 µm, about 25 µm to about 30 µm, about 30 µm to about 35 µm, about 35 µm to about 40 µm, about 40 µm to about 45 µm, or about 45 µm to about 50 µm). It can be understood that there is no fundamental limitation preventing the sustained-release tips from having even smaller diameters.

In some embodiments, the sharpness of the implantable sustained-release tip point is described herein in terms of tip radius. The molds used in the fabrication of the microneedles described herein are designed to have a tip radius between about 0.5 µm to about 10 µm (e.g., about 0.5 µm, 0.6 µm, 0.7 µm, 0.8 µm, 0.9 µm, lum, 2 µm, 3 µm, 4 µm, 5 µm, 6 µm, 7 µm, 8 µm, 9 µm, or 10 µm). In some embodiments, the tip radius is between about 20 µm to about 25 µm (e.g., about 20 µm, 21 µm, 22 µm, 23 µm, 24 µm, or 25 µm). Without being bound by theory, it can be understood that blunter needles may require more force to penetrate the epidermis. In embodiments, other dimensions of the implantable sustained-release tip may be controlled by the shape of the mold and fill volume. In some embodiments, the implantable sustained-release tip have an included angle between about 5 degrees and about 45 degrees (e.g., about 5, 6, 7, 8, 9, 10, 15, 20, 25, 30, 35, 40, or 45 degrees). In some embodiments, the implantable sustained-release tip can have an included angle between about 15 degrees and 45 degrees (e.g., about 15 degrees, about 16 degrees, about 17 degrees, about 18 degrees, about 19 degrees, about 20 degrees, about 21 degrees, about 22 degrees, about 23 degrees, about 24 degrees, about 25 degrees, about 26 degrees, about 27 degrees, about 28 degrees, about 29 degrees, about 30 degrees, about 31 degrees, about 32 degrees, about 33 degrees, about 34 degrees, about 35 degrees, about 36 degrees, about 37 degrees, about 38 degrees, about 39 degrees, about 40 degrees, about 41 degrees, about 42 degrees, about 43 degrees, about 44 degrees, or about 45 degrees.

In embodiments, the height of the implantable sustained-release tip may depend on the formulation and print volume, which can influence the surface tension and drying kinetics. In some embodiments, the height of the implantable sustained-release tip may extend to half of the full height of the microneedle. In some embodiments, the height of the implantable sustained-release tip is between about 75 μm to about 475 μm (e.g., about 75, about 100 μm, about 125 μm, about 150 μm, about 175 μm, about 200 μm, about 225 μm, about 250 μm, about 275 μm, about 300 μm, about 325 μm, about 375 μm, about 400 μm, about 425 μm, or about 475 μm). In some embodiments, the base of the tip comprises a thin "shell"-like layer roughly between about 5-10 μm thick (e.g., about 5, 6, 7, 8, 9, or 10 μm thick). In some embodiments, the implantable sustained-release tip may dry to a more solid construct with minimal "shell" wherein the height may be closer to 150 μm (e.g., between about 50 μm and about 200 μm) and the thickness >50 μm (e.g., between about 25 μm and about 75 lam).

In various embodiments, the disclosed microneedle tips can further comprise at least one additional therapeutic agent, wherein the additional therapeutic can be dispersed throughout the microneedle or form at least a portion of the microneedle tip. In some embodiments, the additional therapeutic agent is useful in the treatment of a viral infection described herein. Optionally the microneedle tips can further comprise an excipient and/or adjuvant, as described herein.

Viruses, Antigens, and Immunogens

The present invention provides, in some embodiments, the delivery, e.g., the controlled- or sustained-delivery, of various therapeutic agents, such as vaccines, antigens, and/or immunogens derived from a virus that is a member of the family Orthomyxovirus, e.g., by a formulation, composition, articles, device, preparations, microneedle and/or microneedle device (e.g., a microneedle patch) described herein and/or according to a method described herein. In some embodiments, a vaccine, a microneedle, and/or a microneedle device (e.g., a microneedle patch) described herein may comprise a negative-sense ssRNA virus and/or an RNA virus, such as an influenza virus. In some embodiments, the vaccine, antigen, and/or immunogen comprises a nucleic acid (e.g., a DNA and/or RNA) derived from an influenza virus. In some embodiments, the vaccine, antigen, and/or immunogen comprises an amino acid (e.g., a peptide and/or protein) derived from an influenza virus. In some embodiments, the influenza vaccine, antigen, and/or immunogen comprise an inactivated and/or a live attenuated virion, or split virion, of an influenza virus. In some embodiments, the vaccine and/or the microneedle comprises a non-replicating viral antigen.

In particular, the invention contemplates a vaccine, a microneedle, and/or a microneedle device (e.g., a microneedle patch) comprising an influenza virus vaccine, antigen, and/or immunogen. The influenza virus is a RNA virus (e.g., a linear negative-sense single stranded RNA virus). There are four known genera of influenza virus, each containing a single type (e.g., Influenza A, B, C, and D). Influenza viruses can continuously change and are subject to both antigenic drift and antigenic shift. Exemplary influenza strains are further described in the Examples (see, e.g., Tables 1 and 2).

Influenza A can be divided into subtypes on the basis of two proteins on the surface of the virus: hemagglutinin (HA) and neuraminidase (NA). Influenza A comprises 18 known HA subtypes, referred to herein as H1-H18, and 11 known NA subtypes, referred to herein as N1-N11. Many different combinations of HA and NA proteins may be found on the surface of the influenza A virus. For example, an "H1N1 virus" designates an influenza A virus subtype comprising an H1 protein and an N1 protein. Exemplary influenza A virus subtypes confirmed to infect humans include, but are not limited to, H1N1, H3N2, H2N2, H5N1, H7N7, H1N2, H9N2, H7N2, H7N3, H1ON7, and H7N9. The H1N1 virus and H3N2 virus are currently in general circulation among humans.

Exemplary Influenza B viruses may belong to, e.g., the B/Yamagata lineage and/or the B/Victoria lineage.

Vaccines

Non-limiting examples of influenza vaccines for use in the microneedles and microneedle devices (e.g., microneedle patches) described herein can include a commercial vaccine, such as a seasonal vaccine, a pandemic vaccine, and/or a universal vaccine; eggbased vaccines, cell-culture based vaccines; recombinant vaccines; live attenuated, inactivated whole virus, split virion, and/or protein subunit vaccines; and adjuvanted vaccines. Various commercial influenza vaccines are listed below. Additionally, influenza vaccines comprising an mRNA, a DNA, a viral vector, and/or a virus-like particle (VLP) are suitable for use in the microneedles and microneedle devices (e.g., microneedle patches) described herein. In some embodiments, the influenza vaccine may target matrix protein 1, matrix protein 2 (M2e), and/or nucleoprotein (NP) of an influenza virus.

TABLE 1

Exemplary Vaccines

| Vaccine | Manufacturer |
|---|---|
| Seasonal Influenza Vaccines | |
| Fluzone High Dose | Sanofi Pasteur |
| Fluzone Quadrivalent | Sanofi Pasteur |
| Fluzone Intradermal Quadrivalent | Sanofi Pasteur |
| Afluria/Fluvax | Seqirus |
| Agriflu | Seqirus |
| Fluad | Seqirus |
| Flucelvax | Seqirus |
| Fluvirin | Seqirus |
| Aggripal | Seqirus |
| FluMist Quadrivalent | Medimmune |
| Flublok | Protein Sciences (Sanofi Pasteur) |
| FluLaval | GlaxoSmithKline |
| Fluarix | GlaxoSmithKline |
| Influvac | Influvac |
| Preflucel | Nanotherapeutics |
| Anflu | Sinovac Biotech |
| Pandemic Influenza Vaccines | |
| Influenza Virus Vaccine, H5N1 | Sanofi Pasteur |
| Pandemrix | Pandemrix |
| Panflu | Sinovac Biotech |
| Panflu 1 | Sinovac Biotech |

Vaccine Formulations and Composition for Controlled- or Sustained-Release

At least one vaccine, antigen, and/or immunogen described herein (e.g., at least one vaccine, antigen, and/or immunogen derived from an influenza virus described herein) can be incorporated into a variety of formulations, compositions, articles, devices, and/or preparations for administration, e.g., to achieve controlled- and/or sustained release. More particularly, at least one vaccine, antigen, and/or immunogen described herein (e.g., at least one vaccine, antigen, and/or immunogen derived from an influenza virus described herein) can be formulated into formulations, compositions, articles, devices, and/or preparations by combination with appropriate, pharmaceutically acceptable carriers or diluents, and can be formulated into preparations in semi-solid, solid, or liquid formats. In some embodiments, the formulations, compositions, articles, devices, and/or preparations described herein comprise silk fibroin, although this is merely exemplary and is not a required material. Exemplary formulations, compositions, articles, devices, and/or preparations comprise: a microneedle (e.g., a microneedle device, e.g., a microneedle patch, e.g., as described herein), an implantable device (e.g., a pump, e.g., a subcutaneous pump), an injectable formulation, a depot, a gel (e.g., a hydrogel), an implant, and a particle (e.g., a microparticle and/or a nanoparticle). As such, administration of the compositions can be achieved in various ways, including intradermal, intramuscular, transdermal, subcutaneous, or intravenous administration. Moreover, the formulations, compositions, articles, devices, and/or preparations can be formulated and/or administered to achieve controlled- and/or sustained release of the at least one vaccine, antigen, and/or immunogen described herein (e.g., at least one vaccine, antigen, and/or immunogen derived from an influenza virus described herein).

In some embodiments, the vaccine (e.g., the influenza vaccine) is administered, e.g., substantially sustained, over a period of, or at least 1, 5, 10, 15, 30, 45 minutes; a period of, or at least, 1, 2, 3, 4, 5, 10, 24 hours; a period of, or at least, 1, 2, 3, 4, 5, 6, 7, 8, 9, 10, 11, 12, 13, 14 days; a period of, or at least, 1, 2, 3, 4, 5, 6, 7, 8 weeks; a period of, or at least 1, 2, 3, 4, 5, 6, 7, 8, 9, 10, 11 months; a period of, or at least, 1, 2, 3, 4, 5 years, or longer. In one embodiment, the vaccine (e.g., the influenza vaccine) is administered as a controlled- or sustained release formulation, dosage form, or device. In certain embodiments, the vaccine (e.g., the influenza vaccine) is formulated for continuous delivery, e.g., intradermal, intramuscular, and/or intravenous continuous delivery. In some embodiments, the composition or device for the controlled- or sustained-release of the vaccine is chosen from: a microneedle (e.g., a microneedle device, e.g., a microneedle patch), an implantable device (e.g., a pump, e.g., a subcutaneous pump), an injectable formulation, a depot, a gel (e.g., a hydrogel), an implant, or a particle (e.g., a microparticle and/or a nanoparticle). In one embodiment, the vaccine (e.g., the influenza vaccine) is in a controlled- or extended release dosage form or formulation (e.g., a microneedle described herein). In one embodiment, the vaccine (e.g., the influenza vaccine) is administered via an implantable device, e.g., a pump (e.g., a subcutaneous pump), an implant, an implantable tip of a microneedle, or a depot. The delivery method can be optimized such that a vaccine (e.g., an influenza vaccine and/or a coronavirus vaccine, e.g., an mRNA-based vaccine) dose as described herein (e.g., a standard dose) is administered and/or maintained in the subject for a predetermined period (e.g., a period of, or at least: 1, 5, 10, 15, 30, 45 minutes; 1, 2, 3, 4, 5, 10, 24 hours 1, 2, 3, 4, 5, 6, 7, 8, 9, 10, 11, 12, 13, 14 days; 1, 2, 3, 4, 5, 6, 7, 8 weeks; 1, 2, 3, 4, 5, 6, 7, 8, 9, 10, 11 months; 1, 2, 3, 4, 5 years, or longer). The substantially sustained or extended release of the vaccine (e.g., the influenza vaccine) can be used for prevention or treatment of a viral infection (e.g., an influenza viral infection) for a period of hours, days, weeks, months, or years.

The present invention provides, in some embodiments, formulations, compositions, articles, devices, and/or prepa-rations of the invention can be formulated and/or configured for controlled- or sustained-release of a at least one vaccine, antigen, and/or immunogen (e.g., at least one vaccine, antigen, and/or immunogen derived from an influenza virus described herein) in an amount (e.g., a dosage) and/or over a time period sufficient to result in an immune response (e.g., a cellular immune response and/or a humoral immune response) to the virus, e.g., the influenza virus, in the subject.

In some embodiments, the formulations, compositions, articles, devices, and/or preparations of the invention can be formulated and/or configured for controlled- or sustained-release of a at least one vaccine, antigen, and/or immunogen (e.g., at least one vaccine, antigen, and/or immunogen derived from an influenza virus described herein) in an amount (e.g., a dosage) and/or over a time period sufficient to result in broad spectrum immunity in the subject.

The substantially continuously or extended-release delivery or formulation of the vaccine (e.g., the influenza vaccine) can be used for prevention or treatment of a viral infection (e.g., an influenza viral infection) for a period of hours, days, weeks, months, or years.

Exemplary Excipients

In addition, the formulations, compositions, articles, devices, and/or preparations can be formulated with common excipients, diluents or carriers for administered by the intradermal, intramuscular, transdermal, subcutaneous, or intravenous routes. In some embodiments, the formulations, compositions, articles, devices, and/or preparations can be administered, e.g., transdermally, and can be formulated as controlled- or sustained-release dosage forms and the like. The formulations, compositions, articles, devices, and/or preparations described herein can be administered alone, in combination with each other, or they can be used in combination with other known therapeutic agents.

Suitable formulations for use in the present invention are found in Remington's Pharmaceutical Sciences (1985). Moreover, for a review of methods for drug delivery, see, Langer (1990) Science 249:1527-1533. The formulations, compositions, articles, devices, and/or preparations described herein can be manufactured in a manner that is known to those of skill in the art, e.g., by mixing, dissolving, granulating, dragee-making, levigating, emulsifying, encapsulating, entrapping or lyophilizing processes. The following methods and excipients are merely exemplary and are in no way limiting.

The formulations used in the fabrication of the microneedles described herein may include excipients. In embodiments, inclusion of an excipient may be for the purposes of improving the stability of an incorporated vaccine, antigen, and/or immunogen; to increase matrix porosity and diffusivity of the vaccine, antigen, and/or immunogen from the formulation, composition, article, device, preparation, and/or microneedle, e.g., microneedle tip; and/or to increase crystallinity/beta-sheet content of matrix to render the material insoluble.

Exemplary excipients include, but are not limited to, a sugar or a sugar alcohol (e.g., sucrose, trehalose, sorbitol, mannitol, or a combination thereof), a divalent cation (e.g., $Ca2+$, $Mg2+$, $Mn2+$, and $Cu2+$), and/or buffers. In some embodiments, the concentration of an excipient can be used to modify the porosity of the matrix, e.g., with sucrose being used as the most common excipient for this purpose. Excipients may also be added to favor silk self assembly into order beta-sheet secondary structure, and such excipients generally can participate in hydrogen bonding or charge interactions with silk to achieve this effect. Nonlimiting examples of excipients that can be used to favor silk self-assembly into order betasheet secondary structure include monosodium glutamate (e.g., L-glutamic acid), lysine, sugar alcohols (e.g., sorbitol and/or glycerol), and solvents (e.g., DMSO, methanol, and/or ethanol).

In some embodiments, the sugar or the sugar alcohol is sucrose present in an amount less than 70% (w/v), less than 60% (w/v), less than 50% (w/v), less than 40% (w/v), less than 30% (w/v), less than 20% (w/v), less than 10% (w/v), less than 9% (w/v), less than 8% (w/v), less than 7% (w/v), less than 6% (w/v), or 5% (w/v) or less, e.g., immediately before drying.

In some embodiments, the sugar or the sugar alcohol is sucrose present in an amount between about 1% (w/v) to about 10% (w/v), about 2% (w/v) to about 8% (w/v), about 2.2% (w/v) to about 6% (w/v), about 2.4% (w/v) to about 5.5% (w/v), about 2.5 to about 5%, or about 2.4% (w/v), about 2.5%, or about 5% (w/v), e.g., immediately before drying.

In some embodiments, the sugar or the sugar alcohol is trehalose present in an amount between about 1% (w/v) to about 10% (w/v), about 2% (w/v) to about 8% (w/v), about 2.2% (w/v) to about 6% (w/v), about 2.4% (w/v) to about 5.5% (w/v), about 2.5 to about 5%, or about 2.4% A (w/v), about 2.5%, or about 5% (w/v), e.g., immediately before drying.

In some embodiments, the sugar or the sugar alcohol is sorbitol present in an amount between about 1% (w/v) to about 10% (w/v), about 2% (w/v) to about 8% (w/v), about 2.2% (w/v) to about 6% (w/v), about 2.4% (w/v) to about 5.5% (w/v), about 2.5 to about 5%, or about 2.4% (w/v), about 2.5%, or about 5% (w/v), e.g., immediately before drying.

In some embodiments, the sugar or the sugar alcohol is glycerol present in an amount between about 1% (w/v) to about 10% (w/v), about 2% (w/v) to about 8% (w/v), about 2.2% (w/v) to about 6% (w/v), about 2.4% (w/v) to about 5.5% (w/v), about 2.5 to about 5%, or about 2.4% (w/v), about 2.5%, or about 5% (w/v), e.g., immediately before drying.

In some embodiments, the vaccine preparation further comprising a divalent cation. In some embodiments, the divalent cation is selected from the group consisting of $Ca2+$, $Mg2+$, $Mn2+$, and $Cu2+$. In some embodiments, the divalent cation is present in the preparation, e.g., immediately before drying, in an amount between 0.1 mM and 100 mM. In some embodiments, the divalent cation is present in the preparation, e.g., immediately before drying, in an amount between $10-7$ and $10-4$ moles per standard dose of viral immunogen. In some embodiments, the divalent cation is present in the preparation immediately before drying in an amount between $10-10$ to $2\times10-3$ moles.

In some embodiments, the vaccine preparation further comprises poly(lactic-coglycolic acid) (PGLA).

In some embodiments, the viral vaccine preparation further comprising a buffer, e.g., immediately before drying. In some embodiments, the buffer has buffering capacity between pH 3 and pH 8, between pH 4 and pH 7.5, or between pH 5 and pH 7. In some embodiments, the buffer is selected from the group consisting of HEPES and a CP buffer. In some embodiments, the buffer is present in the preparation, e.g., immediately before drying, in an amount between 0.1 mM and 100 mM. In some embodiments, the buffer is present in an amount between $10-7$ and $10-4$ moles per standard dose of viral immunogen. In some embodiments, the buffer is present in an amount between $10-10$ to $2\times10-3$ moles.

In addition, the vaccine can also be formulated as a depot, gel, or hydrogel preparation. Such long acting formulations can be administered by implantation (for example subcutaneously or intramuscularly) or by intramuscular injection. Thus, for example, the vaccine can be formulated with suitable polymeric or hydrophobic materials (for example as an emulsion in an acceptable oil) or ion exchange resins, or as sparingly soluble derivatives, for example, as a sparingly soluble salt.

In some embodiments, the vaccine can be packaged and/or formulated as a particle, e.g., a microparticle and/or a nanoparticle. Typically nanoparticles are from 10, 15, 20, 25, 30, 35, 45, 50, 75, 100, 150 or 200 nm or 200-1,000, e.g., 10, 15, 20, 25, 30, 35, 45, 50, 75, 100, 150, or 200, or 20 or 30 or 50-400 nm in diameter. Smaller particles tend to be cleared more rapidly form the system. Therapeutic agents, including vaccines, can be entrapped within or coupled, e.g., covalent coupled, or otherwise adhered, to nanoparticles.

Lipid- or oil-based nanoparticles, such as liposomes and solid lipid nanoparticles can be used to deliver therapeutic agents, e.g., vaccines, described herein. Solid lipid nanoparticles for the delivery of therapeutic agents are described in Serpe et al. (2004) Eur. J. Pharm. Bioparm. 58:673-680 and Lu et al. (20060 Eur. J. Pharm. Sci. 28:86-95. Polymer-based nanoparticles, e.g., PLGA-based nanoparticles can be used to deliver agents described herein. These tend to rely on a biodegradable backbone with the therapeutic agent intercalated (with or without covalent linkage to the polymer) in a matrix of polymer. PLGA is a widely used in polymeric nanoparticles, see Hu et al. (2009) J. Control. Release 134:55-61; Cheng et al. (2007) Biomaterials 28:869-876, and Chan et al. (2009) Biomaterials 30:1627-1634. PEGylated PLGA-based nanoparticles can also be used to deliver therapeutic agents, see, e.g., Danhhier et al., (2009) J. Control. Release 133:11-17, Gryparis et al (2007) Eur. J. Pharm. Biopharm. 67:1-8. Metal-based, e.g., gold-based nanoparticles can also be used to deliver therapeutic agents. Protein-based, e.g., albumin-based nanoparticles can be used to deliver agents described herein. In some embodiments, a therapeutic agent can be bound to nanoparticles of human albumin.

A broad range of nanoparticles are known in the art. Exemplary approaches include those described in WO2010/005726, WO2010/005723 WO2010/005721, WO2010/121949, WO2010/0075072, WO2010/068866, WO2010/005740, WO2006/014626, 7,820,788, 7,780,984, the contents of which are incorporated herein in reference by their entirety.

Dosages

Any dosage amount (e.g., a standard dose and/or a fractional dose) of a vaccine, antigen, and/or immunogen that is capable of eliciting an immune response (e.g., immunogenicity and/or broad-spectrum immunity) in a subject, e.g., when administered by a microneedle of the invention, may be used according to the methods described herein. In some embodiments, dose, e.g., the standard dose (e.g., human dose) for a vaccine, an antigen, and/or an immunogen (e.g., an influenza vaccine and/or a coronavirus vaccine, e.g., an mRNA-based vaccine) is between about 0.1 µg and about 65 µg (e.g., between about 0.1 µg and about 10 µg, between about 0.1 µg and about 1 µg, between about 0.5 µg and about 5 µg, between about 5 µg and about 10 µg, between about 10 µg and about 20 µg, between about 20 µg and about 30 µg, between about 30 µg and about 40 µg, about 40 µg and about 50 µg, about 50 µg and about 65 µg, e.g., about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 μg). In some embodiments, the dose, e.g., standard human dose, for a vaccine described herein (e.g., an influenza vaccine and/or a coronavirus vaccine, e.g., an mRNA-based vaccine) is approximately between about 1 μg and about 30 μg per strain, e.g., between about 5 μg and about 30 μg per strain (e.g., about 5, 6, 7, 8, 9, 10, 11, 12, 13, 14, 15, 16, 17, 18, 19, 20, 21, 22, 23, 24, 25, 26, 27, 28, 29, or 30 μg per strain). In some embodiments, the dose, e.g., fractional dose, for a vaccine described herein (e.g., an influenza vaccine and/or a coronavirus vaccine, e.g., an mRNA-based vaccine) is no more than 1/X, wherein X is any number, e.g., wherein X is 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, or 100 or more, of the total dose (e.g., a standard dose). It is known in the art, that there is clinical precedent for dose-sparing when delivering influenza vaccine to the intradermal space (e.g., Fluzone ID), and this dose is about 9 μg per strain. Accordingly, in some embodiments the total dosage amount of an influenza vaccine (e.g., Fluzone ID) that can be delivered by a microneedle of the invention can be between about 5 μg and 13 μg (e.g., about 5 μg, about 6 μg, about 7 μg, about 8 μg, about 9 μg, about 10 μg, about 11 μg, about 12 μg, or about 13 μg).

Without wishing to be bound by theory, the total dosage amount (e.g., a standard dose) of a vaccine, antigen, and/or immunogen to be administered by a microneedle described herein can be divided between a plurality of microneedles (e.g., within a patch), such that a microneedle tip can comprises less than about 1% of the total dosage amount (e.g., in an array comprising about 121 microneedles), or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% or more of the total dosage amount. In some embodiments, an implantable microneedle tip, as described herein, can comprise about 0.1μ g to about 65μ g (e.g., about 0.1μ, about 0.2μ, about 0.3μ, about 0.4 μg, about 0.5 μg, about 0.6 μg, about 0.7 μg, about 0.8 μg, about 0.9 μg, about 1 μg, about 1 μg to about 10 μg, about 10 μg to about 20 μg, about 20 μg to about 30 μg, about 30 μg to about 40 μg, about 40 μg to about 50 μg, about 50 μg to about 65 μg) of a vaccine, antigen, and/or immunogen, as described herein.

In some embodiments, the vaccine dosage amount loaded into a microneedle patch can be manipulated via the concentration of antigen in the formulated solution that forms the needle tips, the volume of solution dispensed into each needle tip, and the total number of needles (the former two are more convenient means of varying dose). The dosage released into the skin is related to deployment efficiency (the portion of needle tips that are left behind in the skin after the patch is removed), and also the release profile over time and the residence time of the tips within the skin. Because of the continuous sloughing of skin from the epidermis, deeper deployment within the skin is related to longer residence time. Therefore, it is desirable to maximize the penetration depth of the needle tip (up to a limit defined by the depth of pain receptors within the skin, e.g., at a depth of between about 100 μm and about 600 μm), and also to have the antigen spatially concentrated toward the tip of the needle.

The formulations, compositions, articles, devices, and/or preparations described herein, including the implantable sustained-release tip formulation, are designed to not only sustain release of vaccine antigen over the duration, e.g., of tip retention in the dermis, but to also maintain stability of antigen during this period of time (e.g., at least about 1-2 weeks). In some embodiments, approximately 95-100% of the total dosage amount incorporated, e.g., in a formulation, composition, article, device, preparation, and/or microneedle described herein, can be expected to be available for delivery, e.g., into a subject, e.g., into a tissue of a subject, such as the skin, a mucous membrane, an organ tissue, a buccal cavity, a tissue, or a cell membrane. Without being bound by theory, successful deployment of a microneedle into the skin is at least about 50% and can be as high as 100% of an array (e.g., upon application at least about 50%, 60%, 70%, 80%, 90% or more (e.g., 100%) of the total number of microneedle comprising an array are successfully deployed within, e.g., the skin, for controlled- or sustained-release of a vaccine antigen). In some embodiments, a portion of antigen may not be released from the tips during the duration of deployment.

Uses

The invention also provides methods for delivering a vaccine, an antigen, and/or an immunogen (e.g., an influenza vaccine and/or a coronavirus vaccine, e.g., an mRNA-based vaccine) across a biological barrier (e.g., the skin). Such methods can include providing a formulation, composition, article, device, preparation, and/or microneedle described herein. For example, such methods can include providing at least one microneedle or at least one microneedle device described herein, wherein the microneedle or the microneedle device comprises an implantable tip having at least one vaccine, antigen, and/or an immunogen (e.g., an influenza vaccine and/or a coronavirus vaccine, e.g., an mRNA-based vaccine); causing the microneedle or microneedle device to penetrate into the biological barrier (e.g., the skin); and allowing the vaccine, antigen, and/or an immunogen to be released from the implantable tips over a period of at least about 4 days (e.g., about 1, 2, 3, 4, 5, 6, 7, 8, 9, 10, 11, 12, 13, or 14 or more days, e.g., between about 4 days and about 14 days, e.g., between about 1-2 weeks, about 1-3 weeks, or about 1-4 weeks). In some embodiments, the vaccine, antigen, and/or an immunogen is released into the biological barrier through the degradation and/or dissolution of the implantable microneedle tips. In some embodiments, the microneedle or microneedle device is configured to administer the vaccine, antigen, and/or an immunogen in an amount and/or a duration that results in broad-spectrum immunity in the subject, e.g., an immunity against one or more viral antigens not present in the implantable sustained-release tip, e.g., an immunity against a drifted strain not present in the implantable sustained-release tip.

The invention also provides a method for providing broad-spectrum immunity to a virus, e.g., an influenza virus, in a subject, said method comprising administering a vaccine (e.g., an influenza vaccine and/or a coronavirus vaccine, e.g., an mRNA-based vaccine) in an amount (e.g., a dosage) and/or over a time period sufficient to result in broad-spectrum immunity to a virus, e.g., results in an immune response (e.g., a cellular immune response and/or a humoral immune response) to a drifted strain of the virus, in the subject. In some embodiments, the vaccine is administered in a composition for the controlled- or sustained release of the vaccine (e.g., for the controlled- or sustained-release of one or more viral antigens as described herein). In some embodiments, the vaccine is administered by a device for the controlled- or sustained-release of the vaccine (e.g., for the controlled- or sustained release of one or more viral antigens as described herein). The vaccine can be administered into a subject, e.g., into a tissue or cavity of the subject chosen from skin, mucosa, organ tissue, muscle tissue or buccal cavity.

In some embodiments, the methods described herein comprise administering a in an amount (e.g., a dosage) and/or over a time period sufficient to result in one or more of: (i) exposure in the subject to one or more antigens in the vaccine in an amount and/or period of time to result in broad spectrum immunity, e.g., to result in an immune response (e.g., a cellular immune response and/or a humoral immune response) to a drifted strain of the virus, in the subject; or (ii) a level of one or more antigens in the subject that is substantially steady, e.g., about 20%, 15%, 10%, 5%, or 1% to an amount, e.g., minimum amount, needed to result in an immune response (e.g., a cellular immune response and/or a humoral immune response) to the one or more antigens. In some embodiments, the composition or device for the controlled- or sustained-release of the vaccine is chosen from: a microneedle (e.g., a microneedle device, e.g., a microneedle patch, e.g., as described herein), an implantable device (e.g., a pump, e.g., a subcutaneous pump), an injectable formulation, a depot, a gel (e.g., a hydrogel), an implant, or a particle (e.g., a microparticle and/or a nanoparticle).

In some embodiments, the vaccine is administered, e.g., released by the composition or device for the controlled- or sustained-release of the vaccine, e.g., into the subject, in order to maintain a vaccine dosage (e.g., an antigen concentration) for a period of time sufficient to result in broad spectrum immunity, e.g., to result in an immune response (e.g., a cellular immune response and/or a humoral immune response) to a drifted strain of the virus, in the subject (e.g., wherein the period of time is about 1 to 21 days, e.g., about 5 to 10 days or about 5 to 7 days, e.g., about 1, 2, 3, 4, 5, 6, 7, 8, 9, 10, 11, 12, 13, 14, 15, 16, 17, 18, 19, 20, or 21 days). The composition or device for the controlled- or sustained-release of the vaccine can maintain antigen release and/or level in the subject over a sustained period of time. In some embodiments the composition or device for the controlled- or sustained-release of the vaccine maintains a continuous or non-continuous antigen release into the subject over a sustained period of time. The vaccine can administered, e.g., released by the composition or device for the controlled- or sustained-release, over a period of time comprising at least about one week, e.g., about 1-2 weeks, about 1-3 weeks, or about 1-4 weeks. In some embodiments, the vaccine is administered, e.g., released by the composition or device for the controlled- or sustained-release, over a period of time comprising at least about 4 days (e.g., about 4, 5, 6, 7, 8, 9, 10, 11, 12, 13, 14, 15, 16, 17, 18, 19, or 20 days, or more, e.g., between about 4 days and about 2 weeks, between about 4 days and about 1 week).

The vaccine can be administered in a dosage comprising between about 0.1 µg and about 6.5 µg per strain, e.g., 0.2 µg and about 50 µg per strain (e.g., about each of 0.1, 0.2, 0.3, 0.4, 0.5, 0.6, 0.7, 0 8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 µg per strain). In some embodiments, at least about 1% of the dosage of the vaccine (e.g., at least about 0.5% to about 10%, at least about 5% to about 15% at least about 10% to about 20% of the dosage), e.g., released by the composition or device for the controlled- or sustained-release of the vaccine, e.g., into the subject, is maintained over a period of time comprising at least about 4 days (e.g., about 4, 5, 6, 7, 8, 9, 10, 11, 12, 13, or 14 days, or more, e.g., between about 4 days and about 2 weeks, between about 4 days and about 1 week).

In some embodiments, the vaccine is administered, e.g., released by the composition or device for the controlled- or sustained-release, in a plurality of fractional doses of a total dose (e.g., a standard dose) over a time period, e.g., such that an immune response and/or broad-spectrum immunity is achieved, wherein the amount of the vaccine administered in each of the fractional doses is no more than 1/X, wherein X is any number, e.g., wherein X is 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, or 100 or more, of the total dose (e.g., a standard dose) of the vaccine.

In some embodiments, the vaccine is administered, e.g., released by the composition or device for the controlled- or sustained-release of the vaccine, e.g., into the skin of the subject, in a plurality of doses equivalent to a percentage of a total dose (e.g., a percentage of a standard dose) over a time period, e.g., such that broad-spectrum immunity is achieved, wherein the amount of the vaccine administered in each of the plurality of doses is about X %, wherein X is any number, e.g., wherein X is 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, 100, 125, 150, 175, 200, 300, 400, or 500 or more, of the total dose (e.g., a standard dose) of the vaccine.

The vaccine can be administered according to any of the methods described herein such that broad-spectrum immunity is achieved, e.g., such that an immune response, e.g., a cellular immune and/or humoral immune response to a drifted strain is achieved.

Without wishing to be bound by theory, a subject exposed to and/or infected with a first influenza virus can develop an immune response (e.g., a cellular immune and/or humoral immune response) resulting in the creation of an antibody against that first influenza virus. As antigenic changes (e.g., mutations) accumulate in the first influenza virus over time, the subject's antibodies created against the first influenza virus may no longer recognize the drifted virus (e.g., the antigenically different strain). Using the methods, dosage regimens, microneedles, and microneedle devices described herein, broad-spectrum immunity can be conferred to a subject exposed to, infected with, and/or at risk of infection with an influenza virus. Further, using the methods, dosage regimens, microneedles, and microneedle devices described herein, improved immunogenicity and/or broad-spectrum immunity can be conferred to a subject, e.g., as compared to traditional burst release administration of vaccine. For example, improved immunogenicity and/or broad-spectrum immunity detectable in a subject can be greater (e.g., 1-fold, 2-fold, 3-fold, 4-fold, 5-fold, 6-fold, 7-fold, 8-fold, 9-fold, 10-fold, 11-fold, 12-fold, 13-fold, 14-fold, or 15-fold or more greater) as compared to traditional burst release administration of vaccine, e.g., the administration of a single-dose or a bolus administration of the vaccine.

In some embodiments, the implantable sustained-release tip or the vaccine comprises a first influenza strain and administration of a dose of the first influenza strain (e.g., a first influenza A, B, C, and/or D strain as described herein) to the subject results in the development of broad-spectrum immunity to a second influenza strain (e.g., a drifted influenza A, B, C, and/or D strain as described herein) not present in the implantable sustained-release tip or the vaccine.

In some embodiments, the subject (e.g., the human subject) is a pediatric subject, an adult subject, or an elderly subject. The subject may have been exposed to, infected with, and/or at risk of infection with an influenza virus (e.g., a particular strain of an influenza virus). Such a risk may be due to the health status or age of the subject and/or travel to a region where a particular strain of influenza virus is prevalent.

In some embodiments, the invention provides methods of providing a controlled or sustained-release of a vaccine in a subject. The controlled- or sustained-release of the vaccine can achieve an improved immunogenicity and/or broad-spectrum immunity, as compared to traditional burst release administration of vaccine. Without wishing to be bound by theory, an method of administering a vaccine described herein and/or a controlled- or sustained-release rate, e.g., by a composition and/or a microneedle described herein, that mimics the natural exposure pattern of a subject (e.g., a human subject) to a virus can provide enhanced immunity and/or broad-spectrum immunity to a subject, as compared to traditional single-dose vaccine administration modalities.

In some embodiments, a desired amount of at least one vaccine, antigen, and/or immunogen (e.g., an influenza vaccine and/or a coronavirus vaccine, e.g., an mRNA-based vaccine) can be released from the microneedle (e.g., implantable microneedle tip) described herein in a sustained manner over a pre-defined period of time. In some embodiments, at least about 5% of a vaccine, an antigen, and/or an immunogen (e.g., an influenza vaccine and/or a coronavirus vaccine, e.g., an mRNA-based vaccine), e.g., at least about 10%, at least about 15%, at least about 20%, at least about 30%, at least about 40%, at least about 50%, at least about 60%, at least about 70%, at least about 80%, at least about 90%, at least about 95%, or at least about 97%, about 98%, or about 99%, or 100% of the vaccine, antigen, and/or an immunogen (e.g., an influenza vaccine and/or a coronavirus vaccine, e.g., an mRNA-based vaccine), can be released from the microneedle (e.g., implantable microneedle tips) over a pre-defined period of time. In such embodiments, the desired amount (e.g., a dose, such as a standard dose of a vaccine) of the vaccine, antigen, and/or immunogen (e.g., an influenza vaccine and/or a coronavirus vaccine, e.g., an mRNA-based vaccine) can be released from the microneedle over seconds, minutes, hours, months and/or years. In some embodiments, the desired amount (e.g., a dose, such as a standard dose of a vaccine) of the vaccine, antigen, and/or immunogen (e.g., an influenza vaccine and/or a coronavirus vaccine, e.g., an mRNA-based vaccine) can be released from the microneedle upon insertion into a biological barrier, e.g., within 5 seconds, within 10 seconds, within 30 seconds, within 1 minute, within 2 minutes, within 3 minutes, within 4 minutes, within 5 minutes or longer. In some embodiments, the desired amount (e.g., a dose, such as a standard dose of a vaccine) of the vaccine, antigen, and/or immunogen (e.g., an influenza vaccine and/or a coronavirus vaccine, e.g., an mRNA-based vaccine) can be released from the microneedle over a period of at least about 1 hour, at least about 2 hours, at least about 3 hours, at least about 6 hours, at least about 12 hours, at least about 1 day, at least about 2 days, at least about 3 days, at least about 4 days, at least about 5 days, at least about 6 days, at least about 1 week, at least about 2 weeks, at least about 1 month, at least about 2 months, at least about 3 months, at least about 6 months or longer. In some embodiments, the desired amount (e.g., a dose, such as a standard dose of a vaccine) of the vaccine, antigen, and/or immunogen (e.g., an influenza vaccine and/or a coronavirus vaccine, e.g., an mRNA-based vaccine) can be released from the microneedle over about 1 year or longer.

In some embodiments, the invention provides methods for enhancing an immune response to a virus in a subject. In some embodiments, the presence of a cell-mediated immunological response can be determined by any art-recognized methods, e.g., proliferation assays (CD4+ T cells), CTL (cytotoxic T lymphocyte) assays (see Burke, supra; Tigges, supra), or immunohistochemistry with tissue section of a subject to determine the presence of activated cells such as monocytes and macrophages after the administration of an immunogen. One of skill in the art can readily determine the presence of humoral-mediated immunological response in a subject by any well-established methods. For example, the level of antibodies produced in a biological sample such as blood can be measured by western blot, ELISA or other methods known for antibody detection. In some embodiments, an elevated hemagglutination inhibition (HAI) antibody titer is detectable in the blood of the subject for the duration of a complete flu season post immunization.

In some embodiments, the immune response and/or the broad-spectrum immunity is a cellular immune and/or humoral immune response comprising: (i) an elevated hemagglutination inhibition (HAI) antibody titer detectable in the blood of the subject, e.g., detectable at least 3, 4, 5, 6, 7, 8, 9, 10, 11, 12, 13, 14, 15, 16, 17, 18, 19, 20, 21, 22, 23, 24, 25, 26, 27, 28, 29, and/or 30-weeks or more post immunization; (ii) an elevated anti-influenza IgG titer detectable in the blood of the subject, e.g., detectable at least 1, 2, 3, 4, 5, 6, 7, 8, 9, 10, 11 and/or 12-months or more post immunization; and/or (iii) a level of antibody secreting plasma cells (ASC) against the virus, e.g., the influenza virus, detectable in the bone marrow of the subject, e.g., detectable at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, and/or 34-weeks or more post immunization. In some embodiments, the elevated HAI antibody titer is to a drifted influenza A, B, C, and/or D strain. In some embodiments, the elevated anti-influenza IgG titer is to a drifted influenza A, B, C, and/or D strain. In some embodiments, the immune response is a cellular immune response comprising an increase in the level of IFN\17 secreting cell in the blood of the subject, e.g., at least 2, 3, 4, 5, 6, 7, 8, 9, 10, 11, and/or 12-weeks or more post immunization, e.g., by a microneedle described herein.

In some embodiments, the elevated HAI antibody titer, the elevated anti-influenza IgG titer, the level of antibody secreting plasma cells (ASC) against the virus, and/or the level of IFN-γ secreting cells detectable in the subject is greater (e.g., 1-fold, 2-fold, 3-fold, 4-fold, 5-fold, 6-fold, 7-fold, 8-fold, 9-fold, 10-fold, 11-fold, 12-fold, 13-fold, 14-fold, or 15-fold or more greater) as compared to the administration of a single-dose or a bolus administration of the vaccine.

In some embodiments, broad-spectrum immunity can be characterized by measuring the percent seroconversion in a subject. For example, broad-spectrum immunity can comprise a percent seroconversion, e.g., based on the elevated HAI antibody titer detectable in the blood of the subject, e.g., at 6-month post immunization greater than about 20% (e.g., 20%, 25%, 30%, 35%, 40%, 45%, 50%, 55%, 60%, 65%, 70%, 75%, 80%, 85%, 90%, or 95% or more, e.g., 100%). Such a level of seroconversion associated with broadspectrum immunity conferred by using the methods, dosage regimens, microneedles, and microneedle devices described herein can be greater (e.g., 1-fold, 2-fold, 3-fold, 4-fold, 5-fold, 6-fold, 7-fold, 8-fold, 9-fold, 10-fold, 11-fold, 12-fold, 13-fold, 14-fold, or 15-fold or more greater) as compared to a level of seroconversion obtained by traditional burst release administration of vaccine, e.g., the administration of a single-dose or a bolus administration of the vaccine.

Combination Therapies

The microneedles and microneedle devices (e.g., microneedle patches) described herein may be manufactured by precision filling of each individual microneedle tip to enable different patterns of vaccine delivery, dosing schemes, and combination administration of a vaccine with an additional therapeutic agent. The methods of immunization, vaccine delivery, and dosing described herein may comprise combination administration of a vaccine with an additional therapeutic agent. In some embodiments, an additional therapeutic agent may be formulated in the same tip as a vaccine. In some embodiments, an additional therapeutic agent may be formulated with the vaccine. For example, adjuvants to boost immune response to co-delivered antigen could be delivered in the same microneedle tip and/or vaccine. Without wishing to be bound by theory, such a combination therapy could include adjuvants to drive stronger cellular immune responses and/or mucosal responses. Moreover, additional influenza antigens could be delivered for heterologous "prime/boost-like" immunization, e.g., primary immunization with an HA antigen from various influenza strains and a boost (e.g., provided via controlled- or sustained-release or distinct kinetic pattern from "prime") with a different antigen (e.g., a drifted strain, a hemagglutinin stem, m2e protein, or NA).

Formulation compatibility may limit whether two given therapeutic agents can be co-formulated to be dispensed into the same needle tip. In case co-formulation is not possible, the manufacturing process can be adapted in order to dispense a first formulation into a portion of the needle array and then dispense a second formulation into a different portion of the needle array. Different formulations can also receive different process treatments after filling. For instance, if the first formulation will be for controlled- or sustained-release and the silk will be rendered less soluble via water annealing, while the second formulation will be for burst release with no annealing, the second formulation can be dispensed after the annealing step. The manufacturing approach is flexible so other process sequences are possible.

In some embodiments, the invention also provides methods for combination therapies, wherein a microneedle or microneedle device of the invention can be fabricated to administer at least one additional therapeutic agent. Various forms of a therapeutic agent can be used which are capable of being released from the microneedles described herein into adjacent tissues or fluids upon administration to a subject. In some embodiments, an additional therapeutic agent can be included within the base layer and/or within the implantable tip.

Examples of additional therapeutic agents that can be used according to the methods of the invention, e.g., incorporated into a microneedle of the invention, e.g., during fabrication, include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antiviral s, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., mRNA sequences or antisense oligonucleotides that bind to a target nucleic acid sequence), peptides, proteins, antibodies, photodynamic agents (e.g., rhodamine 123), radionuclides (e.g., 1-131, Re-186, Re-188, Y-90, Bi-212, At-211, Sr-89, Ho-166, Sm-153, Cu-67 and Cu-64), toxins (e.g., ricin), and transcription-based pharmaceuticals.

Exemplary Kits

In certain embodiments, the invention relates to a package or kit comprising a microneedle described herein (e.g., a microneedle including a vaccine, antigen, and/or an immunogen as described herein, such as an influenza virus). In some embodiments, the invention relates to a package or kit comprising a vaccine described herein (e.g., a vaccine, antigen, and/or an immunogen as described herein, such as an influenza virus). In some embodiments, the kit can further comprise an additional therapeutic for combination therapy with the microneedle. In some embodiments, the kits can further comprise a disinfectant (e.g., an alcohol swab). In some embodiments, such packages, and kits described herein can be used for vaccination purposes, e.g., to achieve broad-spectrum immunity in a subject as described herein.

While various embodiments have been described above, it should be understood that they have been presented by way of example and not limitation. It will be apparent to persons skilled in the relevant art(s) that various changes in form and detail may be made therein without departing from the spirit and scope. In fact, after reading the above description, it will be apparent to one skilled in the relevant art(s) how to implement alternative embodiments. For example, other steps may be provided, or steps may be eliminated, from the described flows, and other components may be added to, or removed from, the described systems. Accordingly, other implementations are within the scope of the following claims.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112 (f). Claims that do not expressly include the phrase "means for" or "step for" are not to be interpreted under 35 U.S.C. 112 (f).

Additional Empirical Data Comparing the Clinical Applicator, Standard Applicator, and Modified Applicator Described Herein

TABLE 8

| Applicator | Energy/ Needle [mJ] | Piston Velocity [m/s] | Tip Length [um] | Pre-deployment needle height [um] | Air Gap [um] | Penetration Depth (Primary- Air Gap) [um] |
|---|---|---|---|---|---|---|
| Clinical | 1.92 | 7 | 385 | 910 | 516 | 297 |
| Clinical | 1.92 | 7 | 442 | 903 | 485 | 348 |

TABLE 8-continued

| Applicator | Energy/ Needle [mJ] | Piston Velocity [m/s] | Tip Length [um] | Pre-deployment needle height [um] | Air Gap [um] | Penetration Depth (Primary- Air Gap) [um] |
|---|---|---|---|---|---|---|
| Clinical | 1.92 | 7 | 598 | 902 | 482 | 313 |
| Clinical | 1.92 | 7 | 444 | 907 | 407 | 500 |
| Clinical | 1.92 | 7 | 485 | 905 | 425 | 479 |
| Clinical | 1.59 | 12.5 | 407 | 919 | 479 | 440 |
| Clinical | 1.92 | 7 | 423 | 932 | 262 | 671 |
| Clinical | 1.92 | 7 | 438 | 943 | 263 | 680 |
| Clinical | 1.92 | 7 | 412 | 902 | 379 | 524 |
| Clinical | 1.92 | 7 | 486 | 922 | 284 | 638 |
| Clinical | 1.92 | 7 | 395 | 894 | 326 | 568 |
| Clinical | 1.92 | 7 | 448 | 894 | 374 | 521 |
| Clinical | 1.92 | 7 | 456 | 912 | 271 | 642 |
| Clinical | 1.92 | 7 | 415 | 915 | 364 | 551 |
| Clinical | 1.92 | 7 | 398 | 920 | 339 | 581 |
| Clinical | 1.92 | 7 | 491 | 900 | 334 | 566 |
| Clinical | 1.92 | 7 | 429 | 891 | 383 | 509 |
| Clinical | 1.92 | 7 | 480 | 896 | 340 | 556 |
| Clinical | 1.92 | 7 | 407 | 894 | 382 | 512 |
| Clinical | 1.92 | 7 | 459 | 896 | 428 | 468 |
| Clinical | 1.92 | 7 | 419 | 910 | 414 | 496 |
| Clinical | 1.92 | 7 | 502 | 886 | 426 | 460 |
| Clinical | 1.92 | 7 | 532 | 874 | 481 | 393 |
| Clinical | 1.92 | 7 | 405 | 894 | 374 | 520 |
| Clinical | 1.92 | 7 | 403 | 901 | 379 | 523 |
| Clinical | 1.92 | 7 | 424 | 885 | 455 | 430 |
| Clinical | 1.92 | 7 | 381 | 879 | 444 | 436 |
| Clinical | 1.92 | 7 | 390 | 888 | 458 | 430 |
| Clinical | 1.92 | 7 | 404 | 871 | 434 | 438 |
| Clinical | 1.92 | 7 | 381 | 929 | 305 | 624 |
| Clinical | 1.92 | 7 | 386 | 907 | 361 | 545 |
| Clinical | 1.92 | 7 | 386 | 924 | 360 | 564 |
| Clinical | 3.83 | 7 | 403 | 898 | 382 | 516 |
| Clinical | 1.90 | 7 | 401 | 858 | 476 | 382 |
| Clinical | 2.56 | 7 | 349 | 909 | 440 | 469 |
| Clinical | 1.90 | 7 | 380 | 868 | 451 | 417 |
| Clinical | 3.83 | 7 | 466 | 924 | 370 | 554 |
| Clinical | 2.56 | 7 | 377 | 932 | 457 | 475 |
| Clinical | 3.83 | 7 | 440 | 914 | 319 | 595 |
| Clinical | 2.56 | 7 | 383 | 919 | 445 | 474 |
| Clinical | 3.83 | 7 | 411 | 892 | 352 | 540 |
| Clinical | 2.56 | 7 | 359 | 918 | 370 | 548 |
| Clinical | 3.83 | 7 | 433 | 904 | 317 | 587 |
| Clinical | 2.56 | 7 | 375 | 917 | 500 | 417 |
| Clinical | 3.77 | 7 | 411 | 898 | 375 | 523 |
| Clinical | 3.77 | 7 | 433 | 901 | 411 | 490 |
| Clinical | 3.77 | 7 | 358 | 890 | 356 | 534 |
| Clinical | 3.77 | 7 | 392 | 907 | 399 | 508 |
| Clinical | 3.77 | 7 | 358 | 888 | 339 | 549 |
| Clinical | 3.77 | 7 | 392 | 911 | 373 | 538 |
| Clinical | 3.77 | 7 | 358 | 891 | 279 | 612 |
| Clinical | 3.77 | 7 | 392 | 896 | 280 | 616 |
| Clinical | 3.83 | 7 | 360 | 902 | 408 | 494 |
| Clinical | 3.77 | 7 | 352 | 897 | 377 | 520 |
| Clinical | 3.77 | 7 | 438 | 909 | 398 | 511 |
| Clinical | 3.77 | 7 | 366 | 894 | 345 | 549 |
| Clinical | 3.77 | 7 | 389 | 890 | 334 | 556 |
| Clinical | 3.77 | 7 | 366 | 895 | 349 | 546 |
| Clinical | 3.77 | 7 | 389 | 891 | 396 | 495 |
| Clinical | 3.77 | 7 | 366 | 900 | 361 | 539 |
| Clinical | 3.77 | 7 | 389 | 902 | 382 | 520 |
| Clinical | 3.77 | 7 | 478 | 832 | 305 | 527 |
| Clinical | 1.92 | 7 | 386 | 929 | 462 | 467 |
| Combined mods. | 2.10 | 12.5 | 417 | 913 | 375 | 538 |
| Combined mods. | 1.40 | 10.4 | 417 | 902 | 395 | 507 |
| Combined mods. | 2.10 | 12.5 | 429 | 914 | 332 | 582 |
| Combined mods. | 3.90 | 12.7 | 421 | 920 | 446 | 474 |
| Combined mods. | 3.13 | 13.8 | 483 | 883 | 346 | 537 |

TABLE 8-continued

| Applicator | Energy/ Needle [mJ] | Piston Velocity [m/s] | Tip Length [um] | Pre-deployment needle height [um] | Air Gap [um] | Penetration Depth (Primary- Air Gap) [um] |
|---|---|---|---|---|---|---|
| Combined mods. | 3.13 | 13.8 | 486 | 888 | 339 | 549 |
| Combined mods. | 2.10 | 12.5 | 391 | 895 | 389 | 506 |
| Combined mods. | 2.10 | 12.5 | 386 | 881 | 400 | 481 |
| Combined mods. | 2.10 | 12.5 | 452 | 896 | 375 | 521 |
| Combined mods. | 2.10 | 12.5 | 479 | 878 | 363 | 515 |
| Combined mods. | 2.10 | 12.5 | 550 | 889 | 413 | 476 |
| Combined mods. | 2.10 | 12.5 | 468 | 903 | 403 | 500 |
| Combined mods. | 2.10 | 12.5 | 550 | 919 | 427 | 492 |
| Combined mods. | 2.10 | 12.5 | 435 | 906 | 384 | 522 |
| Unmodified | 1.59 | 12.5 | 490 | 926 | 531 | 288 |
| Unmodified | 1.95 | 14 | 406 | 890 | 372 | 518 |
| Unmodified | 1.95 | 14 | 430 | 897 | 387 | 510 |
| Unmodified | 1.83 | 12.5 | 450 | 892 | 442 | 450 |
| Unmodified | 1.83 | 12.5 | 434 | 897 | 437 | 460 |
| Unmodified | 1.83 | 12.5 | 405 | 893 | 457 | 436 |
| Unmodified | 1.83 | 12.5 | 465 | 872 | 445 | 428 |
| Unmodified | 1.83 | 12.5 | 405 | 898 | 479 | 419 |
| Unmodified | 1.83 | 12.5 | 449 | 908 | 478 | 430 |
| Unmodified | 1.83 | 12.5 | 401 | 899 | 497 | 402 |
| Unmodified | 1.83 | 12.5 | 483 | 893 | 530 | 363 |
| Unmodified | 1.83 | 12.5 | 382 | 916 | 516 | 400 |
| Unmodified | 1.83 | 12.5 | 412 | 921 | 551 | 374 |
| Unmodified | 1.83 | 12.5 | 415 | 931 | 532 | 400 |
| Unmodified | 2.50 | 16 | 426 | 885 | 340 | 544 |
| Unmodified | 2.50 | 16 | 426 | 895 | 353 | 542 |
| Unmodified | 2.50 | 16 | 427 | 891 | 373 | 518 |
| Unmodified | 2.49 | 16 | 394 | 906 | 374 | 531 |
| Unmodified | 2.49 | 16 | 389 | 898 | 394 | 505 |
| Unmodified | 2.49 | 16 | 413 | 884 | 373 | 511 |
| Unmodified | 2.50 | 16 | 381 | 902 | 400 | 502 |
| Unmodified | 2.50 | 16 | 415 | 912 | 411 | 501 |
| Unmodified | 2.50 | 16 | 368 | 895 | 418 | 477 |
| Unmodified | 2.50 | 16 | 366 | 895 | 502 | 393 |
| Unmodified | 2.50 | 16 | 368 | 902 | 477 | 425 |
| Unmodified | 2.50 | 16 | 358 | 892 | 411 | 481 |
| Unmodified | 2.50 | 16 | 450 | 906 | 374 | 532 |
| Unmodified | 2.50 | 16 | 379 | 904 | 393 | 511 |
| Unmodified | 2.50 | 16 | 381 | 880 | 436 | 444 |
| Unmodified | 2.50 | 16 | 390 | 881 | 398 | 483 |
| Unmodified | 2.50 | 16 | 404 | 885 | 428 | 457 |
| Unmodified | 2.50 | 16 | 383 | 900 | 394 | 506 |
| Unmodified | 2.50 | 16 | 451 | 928 | 388 | 540 |
| Unmodified | 2.52 | 16 | 468 | 918 | 482 | 436 |
| Unmodified | 2.50 | 16 | 389 | 895 | 457 | 438 |
| Unmodified | 2.50 | 16 | 432 | 896 | 433 | 463 |
| Unmodified | 3.39 | 16 | 509 | 904 | 437 | 467 |
| Unmodified | 5.08 | 16 | 403 | 871 | 340 | 531 |
| Unmodified | 2.52 | 16 | 401 | 865 | 393 | 472 |
| Unmodified | 3.39 | 16 | 349 | 887 | 448 | 439 |
| Unmodified | 2.52 | 16 | 380 | 833 | 391 | 442 |
| Unmodified | 2.52 | 16 | 480 | 863 | 407 | 456 |
| Unmodified | 2.52 | 16 | 434 | 936 | 436 | 500 |
| Unmodified | 2.52 | 16 | 426 | 925 | 412 | 513 |
| Unmodified | 2.49 | 16 | 445 | 861 | 386 | 475 |
| Unmodified | 2.49 | 16 | 419 | 902 | 444 | 458 |
| Unmodified | 2.49 | 16 | 413 | 909 | 403 | 506 |
| Unmodified | 2.49 | 16 | 461 | 916 | 393 | 523 |
| Unmodified | 2.49 | 16 | 457 | 906 | 348 | 558 |
| Unmodified | 2.49 | 16 | 441 | 913 | 410 | 503 |
| Unmodified | 2.49 | 16 | 460 | 914 | 415 | 499 |
| Unmodified | 2.49 | 16 | 451 | 826 | 376 | 450 |
| Unmodified | 5.00 | 16 | 447 | 890 | 221 | 669 |
| Unmodified | 2.49 | 16 | 417 | 903 | 436 | 467 |
| Unmodified | 2.49 | 16 | 434 | 911 | 352 | 559 |
| Unmodified | 2.49 | 16 | 441 | 891 | 427 | 464 |

TABLE 8-continued

| Applicator | Energy/ Needle [mJ] | Piston Velocity [m/s] | Tip Length [um] | Pre-deployment needle height [um] | Air Gap [um] | Penetration Depth (Primary- Air Gap) [um] |
|---|---|---|---|---|---|---|
| Unmodified | 2.49 | 16 | 439 | 900 | 391 | 509 |
| Unmodified | 2.49 | 16 | 450 | 828 | 356 | 472 |
| Unmodified | 2.49 | 16 | 431 | 887 | 477 | 410 |
| Unmodified | 2.49 | 16 | 435 | 907 | 367 | 540 |
| Unmodified | 2.49 | 16 | 376 | 907 | 350 | 557 |
| Unmodified | 2.49 | 16 | 376 | 909 | 342 | 567 |
| Unmodified | 2.49 | 16 | 392 | 896 | 383 | 513 |
| Unmodified | 2.49 | 16 | 392 | 887 | 405 | 482 |
| Unmodified | 2.49 | 16 | 441 | 907 | 445 | 462 |
| Unmodified | 2.49 | 16 | 421 | 812 | 235 | 577 |
| Unmodified | 2.49 | 16 | 429 | 911 | 393 | 518 |
| Unmodified | 2.49 | 16 | 550 | 917 | 279 | 638 |

Exemplary Formulations

In some embodiments, various payloads can be included as cargo in the disclosed microneedle tips. Example payloads are shown below in Table 9.

TABLE 9

| Payload | Example |
|---|---|
| Peptide | GLP-1 |
| mRNA (lipid nanoparticle) | mRNA encoding for reporter molecules (e.g. luciferase) or vaccine antigens (e.g. HA) encapsulated in LNPs of various chemistries (e.g. cKK-E12, SM-102, ALC-0315, MC3 ionizable lipids) |
| Virus-like particle | RSV/hMPV VLPs (Icosavax/AZ) |
| Subunit recombinant protein | SARS-CoV-2 S2P |
| Subunit recombinant protein + Adjuvant | SARS-CoV-2 S2P + CpG/Alum; other example adjuvants include squalene oil-in water emulsions, TLR4, TLR7/8 ligands, cGAMP, ASO family |
| Inactivated virus | Influenza vaccine (Fluzone- Sanofi, GCFLU - GC Pharma) |
| Live, attenuated virus | Measles, Rubella |
| mRNA (naked) | |
| mRNA (cationic emulsion) | repRNA/LION (HDT Bio) |
| Anticancer agent | Gemcitabine |
| Immunomodulatory agent | Cytokines (IL-2), TLR agonist, etc. |

In some embodiments, various example formulations for the disclosed microneedle tips are disclosed below in Table 10.

TABLE 10

| Component | | GLP-1 -- 1% PVP K17/ 3% Proline/ 0.1% Kolliphor EL/ 100 mM Tris- HCl | VLP -- 0.5% Fibroin/ 0.25% Tween-80/ 20 mM Tris/ 100 mM NaCl/ 4% Trehalose |
|---|---|---|---|
| Polymers | Fibroin | | 0-0.5% |
| Polymers | PVP K12 | | |
| Polymers | PVP K17 | 0-2.25% | 1-5% |
| Polymers | PVP K30 | | |
| Polymers | PVA 4-88 | | |
| Polymers | Kollidon VA64 (copovidone) | | |
| Polymers | Dextran40 | 1% | 1-5% |
| Polymers | Methyl Cellulose | | 0-2% |
| Polymers | Hydroxypropyl Methyl- cellulose | | 0-2% |

TABLE 10-continued

| Component | | GLP-1 -- 1% PVP K17/ 3% Proline/ 0.1% Kolliphor EL/ 100 mM Tris- HCl | VLP -- 0.5% Fibroin/ 0.25% Tween-80/ 20 mM Tris/ 100 mM NaCl/ 4% Trehalose |
|---|---|---|---|
| Polymers | Carboxymethyl cellulose | | |
| Polymers | Plasdone S-630 (copovidone) | | |
| Polymers | Pullulan | | |
| Polymers | Kollicoat Protect | | |
| Sugars | Sucrose | | 0-10% |
| Sugars | Trehalose | | 0-10% |
| Sugars | Lactose | | |
| Sugar alcohols | Mannitol | | |
| Sugar alcohols | Xylitol | | |
| Sugar alcohols | Sorbitol | | |
| Sugar alcohols | Glycerol | | 0-5% |
| Amino Acids | Arginine-HCl | 0-2.5% | 0-5% |
| Amino Acids | Proline | 0-3% | |
| Amino Acids | Histidine | | |
| Amino Acids | Methionine | | |
| Amino Acids | Aspartic Acid | | |
| Amino Acids | Glutamic Acid | | |
| Antioxidants | Sodium metabisulfite | | |
| Antioxidants | Sodium pyruvate | | |
| Antioxidants | Sodium ascorbate | | |
| Buffers | Tris-HCl | 25-150 mM/ pH 7.4-8.2 | 0-50 mM/ pH 7-8 |
| Buffers | PBS | | |
| Buffers | TE | | |
| Buffers | MOPS | 100 mM/ pH 7-7.9 | |
| Buffers | Phosphate | | |
| Buffers | Bis-tris | | |
| Buffers | HEPES | pH 8.3 | |
| Surfactants | Kolliphor-EL | 0-1% | |
| Surfactants | Kolliphor HS-15 | 0-1% | |
| Surfactants | Pluronic F-127 (Poloxamer 407) | 0-1% | |
| Surfactants | Pluronic F-68 (Poloxamer 188) | | |

TABLE 10-continued

| Component | | GLP-1 -- 1% PVP K17/ 3% Proline/ 0.1% Kolliphor EL/ 100 mM Tris- HCl | VLP -- 0.5% Fibroin/ 0.25% Tween-80/ 20 mM Tris/ 100 mM NaCl/ 4% Trehalose |
|---|---|---|---|
| Surfactants | Tween-20 | 0-1% | 0-0.25% |
| Surfactants | Tween-80 | | 0-0.25% |
| Surfactants | Soluplus | | |
| Surfactants | P124 | | |
| Surfactants | CHAPS | | 0-1% |
| Salts | NaCl | 0-1% | 0-1% |
| Salts | CaCl2 | | |
| Salts | ZnCl2 | | |
| Salts | MgCl2 | 0-5% | |
| Salts | Urea | | |

In some embodiments, various example formulations for the disclosed microneedle bases are disclosed below in Table 11

TABLE 11

| Component | | GLP-1 -- 60% PVP K17/ 0.5% PVA 4-88/ 1X TE Buffer | VLP -- 0.5% Fibroin/ 0.25% Tween-80/ 20 mM Tris/ 100 mM NaCl/ 4% Trehalose | General |
|---|---|---|---|---|
| Primary Component | PVP K12 | | | 50-60% |
| Primary Component | PVP K17 | 50-60% | 55-60% | 55-60% |
| Primary Component | VA64 (copovidone) | | | |
| Primary Component | Dextran | | | 30-50% |
| Primary Component | PVA 4-88 | | | 10-20% |
| Additives | PVA 4-88 | 0.5% | 0.5% | 0.50% |
| Additives | Tris-HCl | 0-20 mM/ pH 7.5-8 | 10-20 mM/ pH 7.5-8 | 10-20 mM/ pH 7.5-8 |
| Additives | MOPS | 0-25 mM/ pH 7.9 | | |
| Additives | Tris-EDTA | 1X | | |
| Additives | Kolliphor EL | | | |
| Additives | Pluronic F-68 (Poloxamer 188) | | | |
| Additives | Kolliphor HS-15 | 0-0.5% | | |
| Additives | F-127 | | | |
| Additives | Tween-20 | 0-0.5% | | 0-0.1% |
| Additives | Triton-X-100 | | 0-0.1% | 0-0.1% |
| Additives | Sucrose | | | 0-30% |
| Additives | Trehalose | | | 0-20% |
| Additives | Glycerol | | | 0-4% |
| Additives | Carboxymethylcellulose | | | 0-4% |
| Additives | Methyl Cellulose | | | 0-4% |
| Additives | Hydroxypropyl Methylcellulose | | | 0-4% |

Exemplary Data Demonstrating Benefits of the System

Figure 23A:
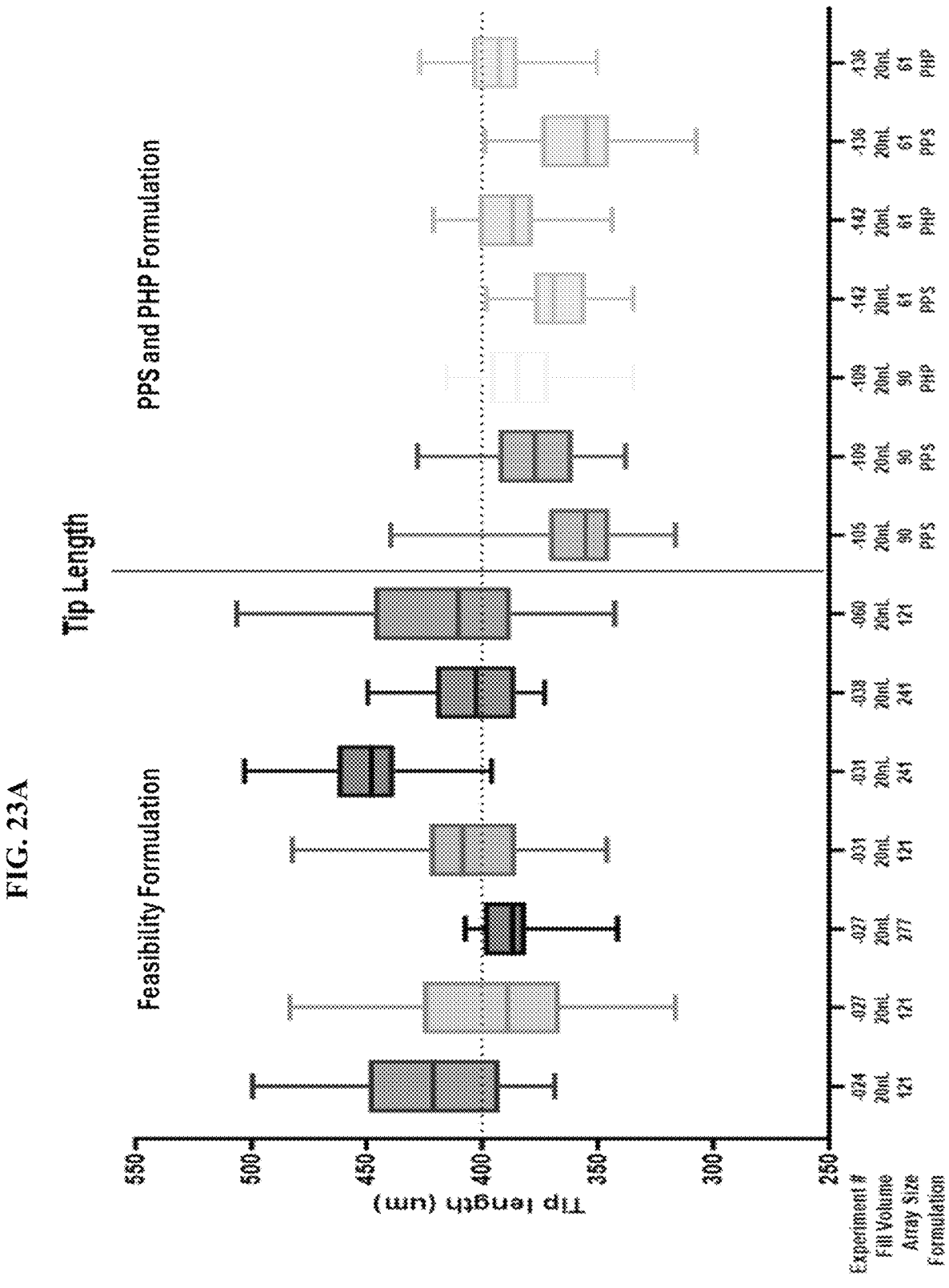
Figure 23B:
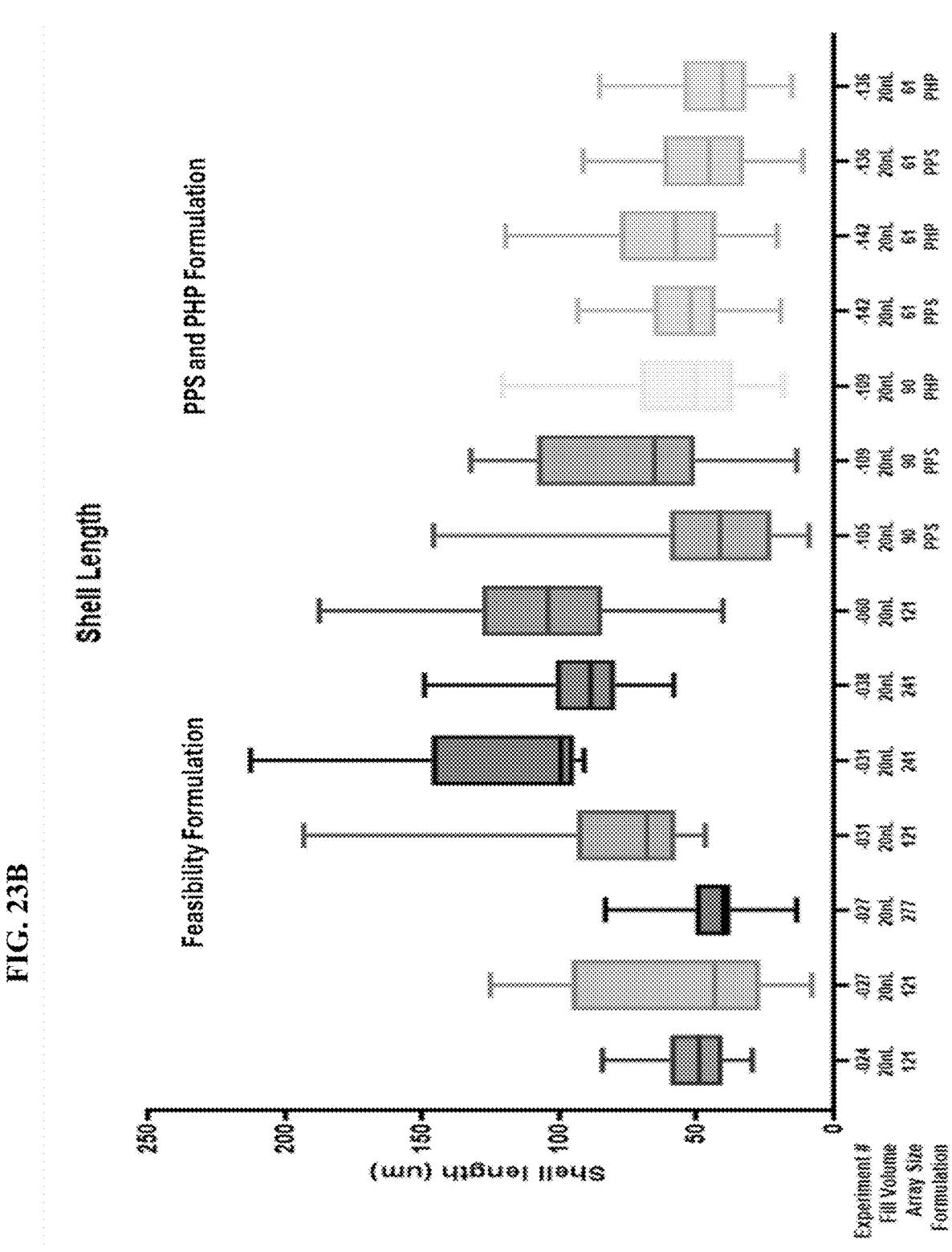

In GLP-136 and GLP-142, two different combinations of proline, and NaCl were evaluated along with Tri-HCl as the buffer (FIG. 22). The PPS formulation contains 180 mg/mL GLP-1, 1% PVP K17, 0.75% Proline, 0.1% Kolliphor EL, 0.9% NaCl, 0.1 mg/mL AF-647, and 100 mM Tris-HCl buffer. PHP formulation contains 180 mg/mL GLP-1, 1% PVP K17, 3% Proline, 0.1% Kolliphor EL, 0.1 mg/mL AF-647, and 100 mM Tris-HCl buffer. Formulation PPS contains 0.9% NaCl and leads to shorter Tips than the PHP formulation that does not contain any NaCl. In both groups the average Tip length was below the target 400 μm. Moreover, the tip strengths are comparable between the two formulation groups and higher than the values observed during the feasibility formulation. A longitudinal summary shows that both the PPS and PHP formulations led to reduced tip and shell lengths relative to the Feasibility Formulation (FIG. 23A-23B).

Figure 24:
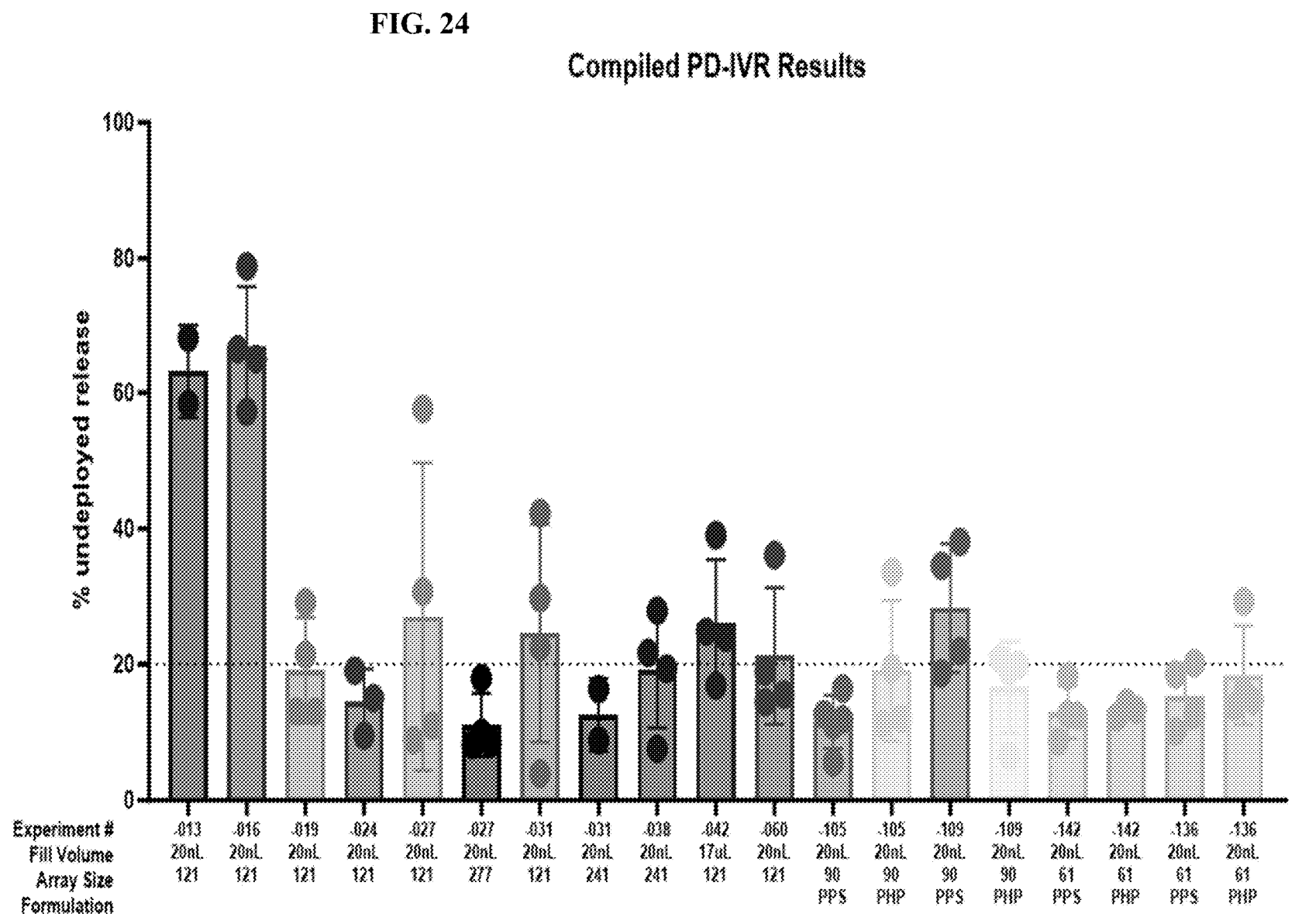

Finally, the intent of developing formulations that improved Tip length and strength was to improve the consistency of GLP-1 delivery into skin. Our goal has been to identify formulations that consistently deliver >80% of the payload. FIG. 24 shows the percent of payload remaining on the patch post ex vivo deployment into pig skin for experiments using the feasibility formulation (GLP-013-GLP-060) and PPS and PHS formulations optimized for tip length and strength (GLP-105-GLP-136). Percent undeployed release is calculated as the amount of GLP-1 remaining on the MAP post ex vivo deployment divided by the total amount of GLP-1 loaded onto the MAP and therefore is a measure of delivery. The data show that the PPS and PHP formulations are associated with more consistent delivery that meets the 80% delivery criteria.

Evaluation of PPS and PHP Formulations in Pharmacokinetic (PK) Studies

The PPS (Form 1) and PHP (Form 2) formulations were evaluated in 3 separate pharmacokinetic (PK) studies in the males Sprague Dawley rat model. The study designs for studies 1 and 2 are shown in Table 12.

TABLE 12

| | MAP Configuration | Route | Array Configuration | Nominal Target Dose | Nominal Dose Per Needle | Group N |
|---|---|---|---|---|---|---|
| Study 1 | | | | | | |
| 1 | Form 1 60 MN | MAP | 60 Needles | 324 ug | 5.4 ug | 5 |
| 2 | Form 1 90 MN | | 90 Needles | 324 ug | 3.6 ug | 5 |
| Study 2 | | | | | | |
| 1 | Form 1 61 MN | MAP | 61 Needles | 324 ug | 5.4 | 5 |
| 2 | Form 2 61 MN | | 61 Needles | 324 ug | 5.4 | 5 |
| 3 | NA | SQ* | NA | 324 ug | NA | 5 |
| | Timepoints: Blood Collection | | | | Pre-dose (Day 0), 3, 24, 72 hr post dose | |

Figure 25A:
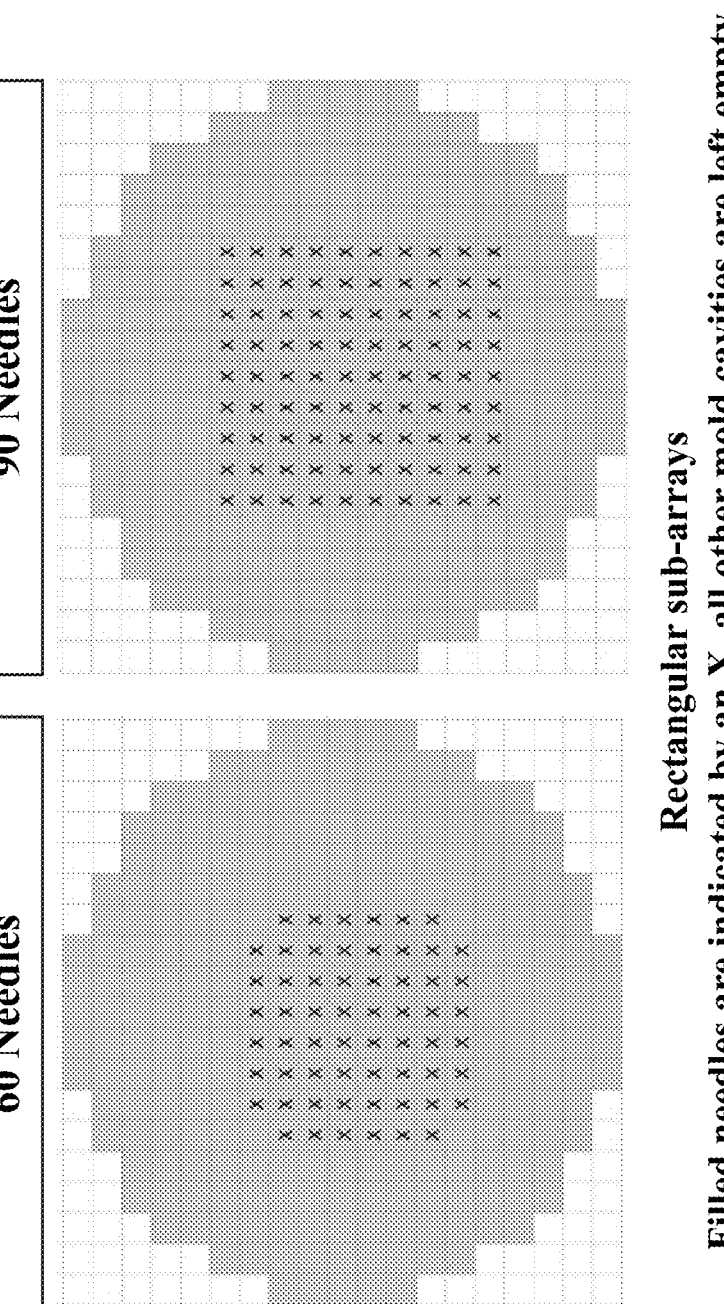
Figure 25B:
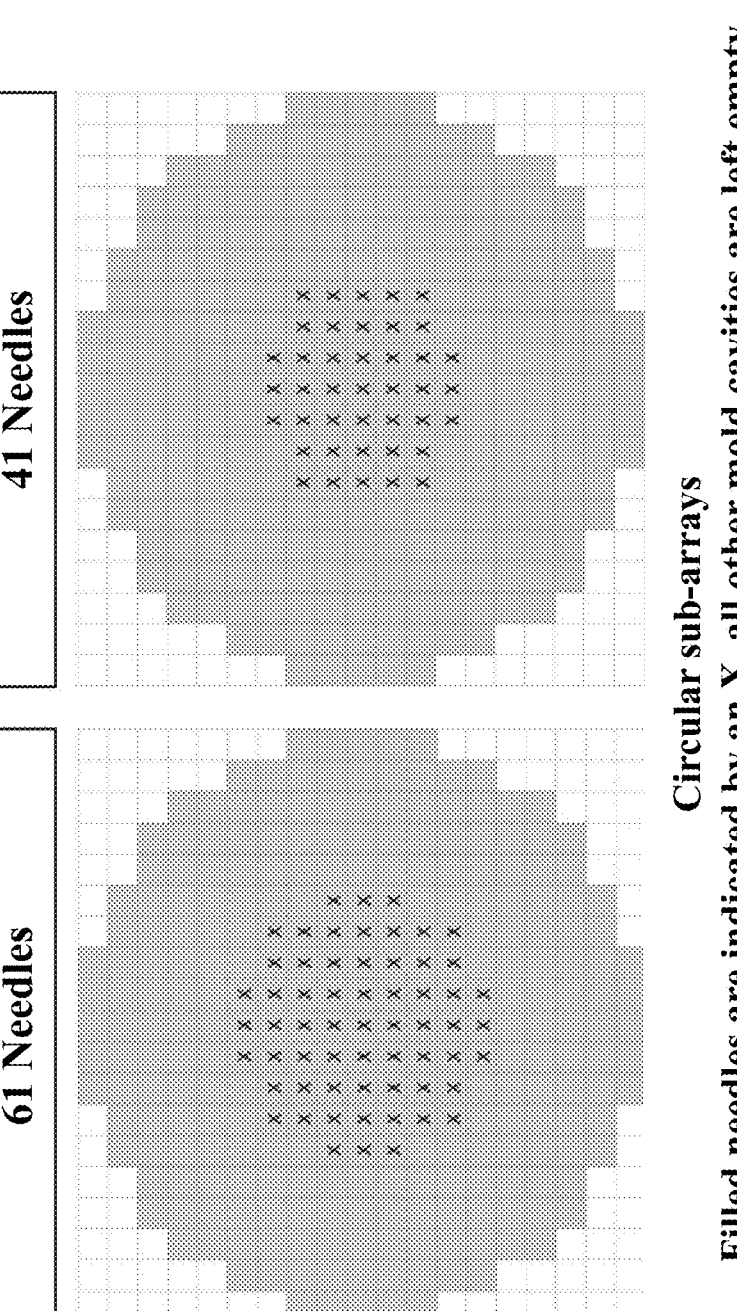

The first study was a pilot study evaluating the impact of array size and dose per needle on the PK profile. Approximately 324 μg of GLP-1 was formulated in Form 1 and delivered with a 60 vs a 90-microneedle array (FIG. 25A). The data (FIG. 25B, top panel) shows a comparable PK profile for both array sizes and dose loadings per needle. The second study was a pilot study evaluating ~5 μg per needle formulated in either Form 1 or Form 2 each delivered with a 61-microneedle array. A semaglutide sample formulated in 100 mM Tris pH 7.5, nominally matched for the intended dose, delivered subcutaneously was included as a comparator. The data (FIG. 25B, bottom panel) suggests both MAP delivered formulations performed similarly and may provide a higher relative bioavailability than subcutaneous delivery (FIG. 25B).

A follow up PK study, with more extensive sampling, particularly in the first 48 hours, was carried out next. The study design is outlined in Table 13.

drug product for each animal, for each treatment group and serves as an estimate of bioavailability. While there is some variation in the AUC for SQ delivered GLP-1, perhaps due to variation in the injections, the BA for Form 2 appears modestly higher than SQ injection.

Full comparison of the PK parameters from this study (FIG. 27) further shows a comparable T1/2 (time to elimination), faster Tmax (time to peak concentration), higher Cmax (maximum concentration) and modestly higher AUC (bioavailability) suggesting that MAP delivery of GLP-1 could support either currently licensed dose levels of GLP-1 or MAP specific treatment regimens.

Based on the formal rat PK study, Form 2 was selected for evaluation in the Gottingen minipig model. This study compared the pharmacokinetics of MAP delivered semaglutide to a SQ injection. A dose of 2 nmol per kg (220 μg total) was evaluated. Two MAP array sizes delivering the same nominal 220 μg dose were evaluated. One was a 61

TABLE 13

| Group Number | Group N | Test Article | Target Dose (mg/kg) | Route | Interim Blood Collection Time Points (Hours) | Individual Body Weights & Application Site Observations |
|---|---|---|---|---|---|---|
| 1 | 8 | Semaglutide* | 0.73 (220 ug per dose) | SQ | Pre-dose (Day −1), 0.5, 1, 2, 4, 6, 8, 10, 12, 24, 30, 48, 96, 120 post dose | Week −1, Day 1, 4, 8 |
| 2 | 8 | MAP Form 1 | 0.73 (220 ug per dose) | Intradermal Patch | | |
| 3 | 8 | MAP Form 2 | 0.73 (220 ug per dose) | | | |

Figure 26A:
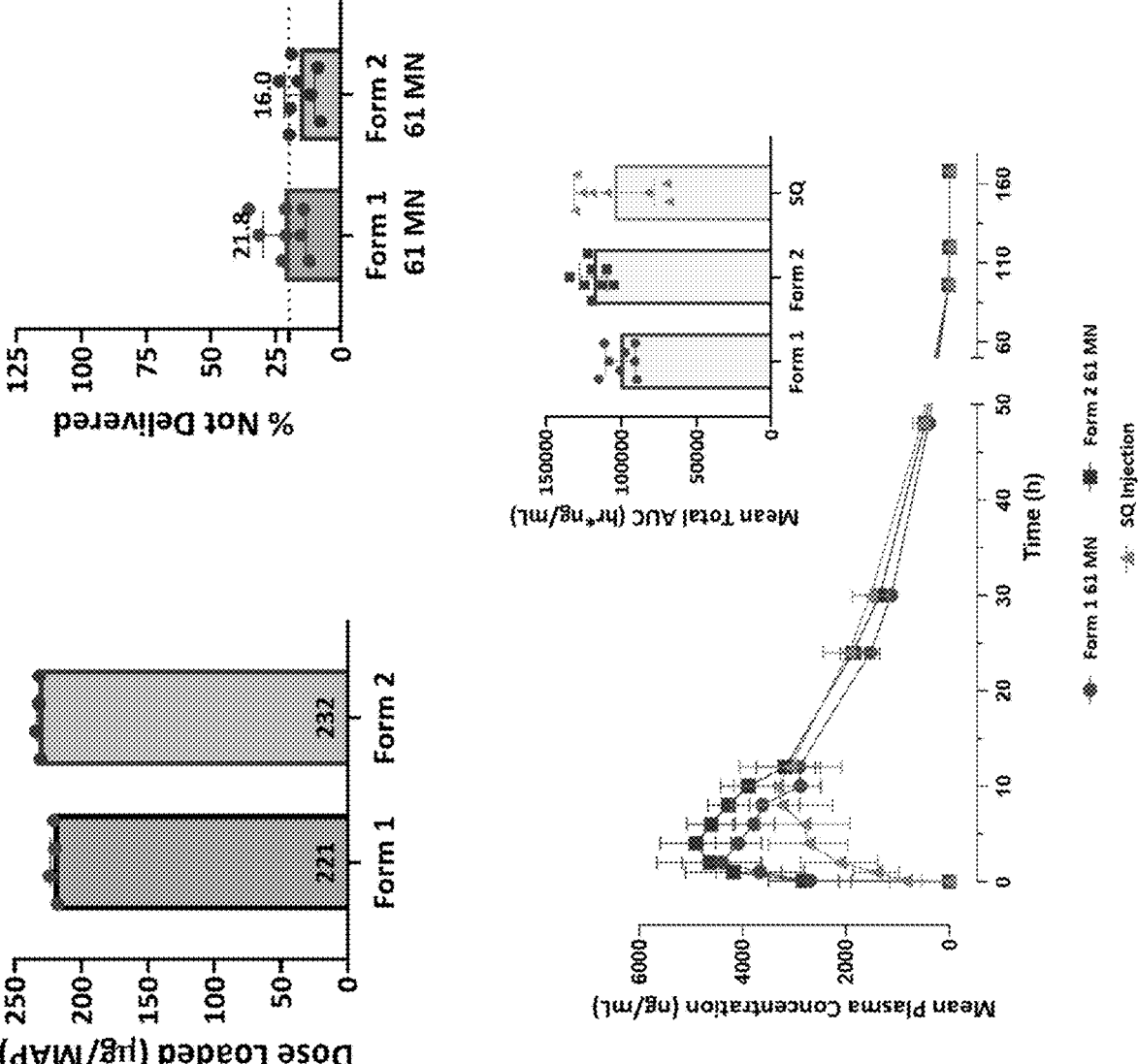
Figure 26B:
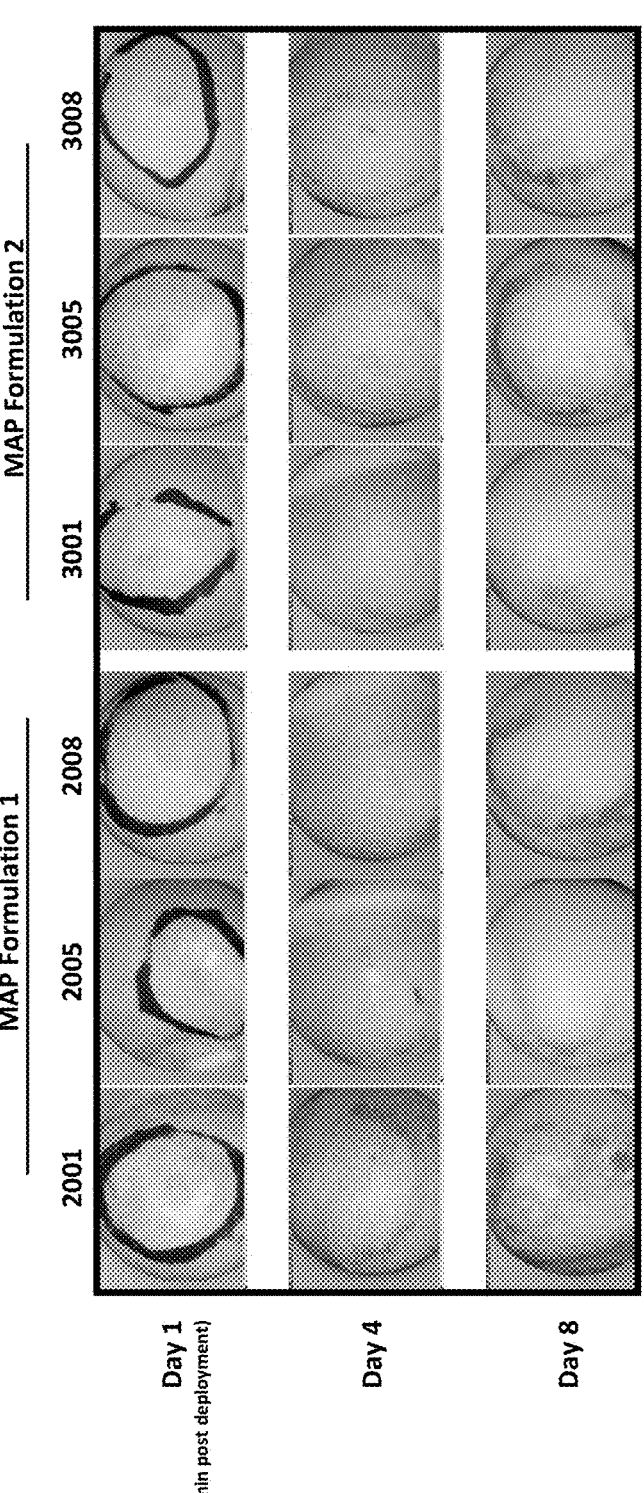
Figure 26C:
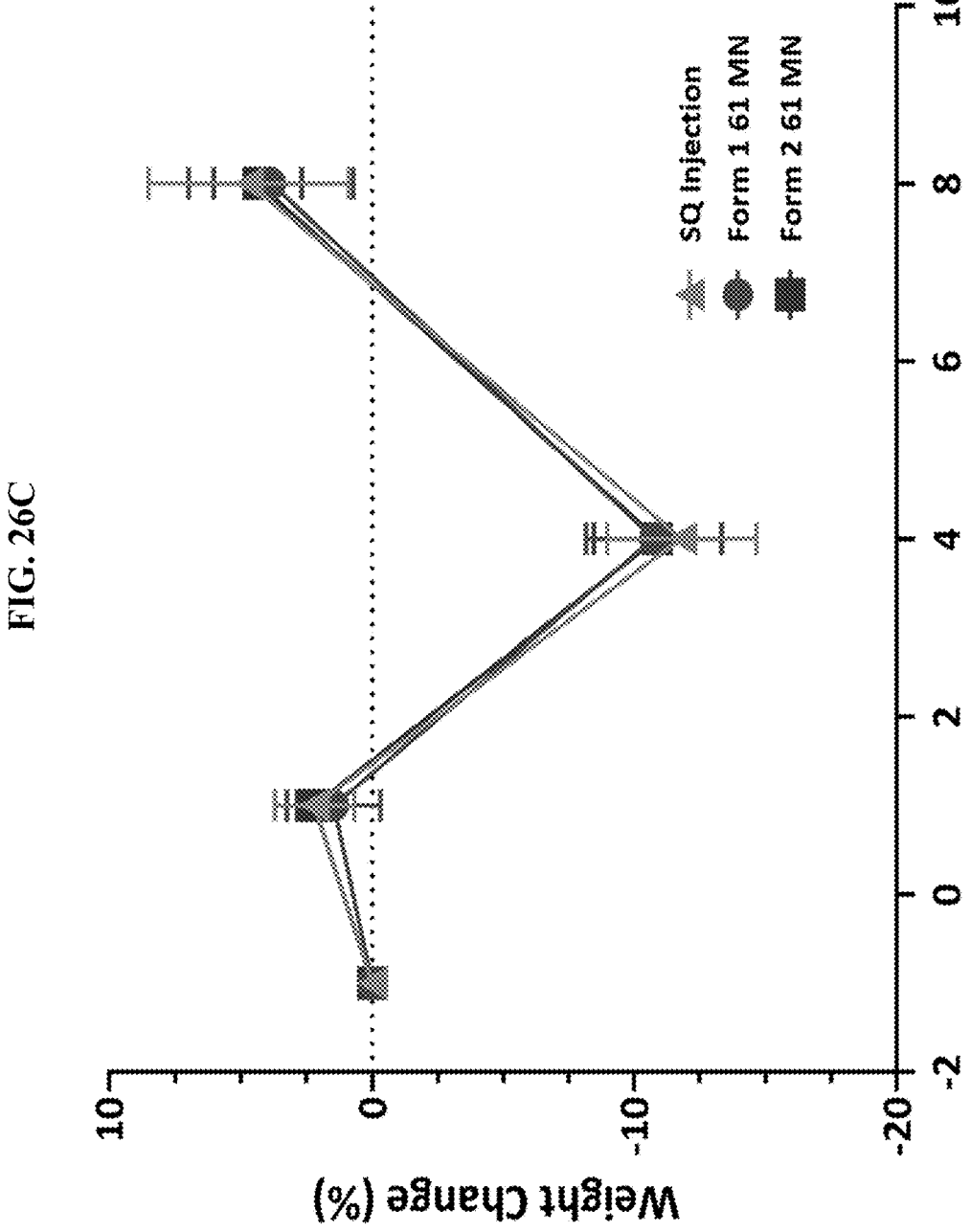

Groups of 8 male Sprague Dawley rats received a 61-microneedle (61 MN) array delivering a target dose of 220 μg of semaglutide formulated in either Form 1 or Form 2. A dose matched sample formulated in Tris buffer delivered by the subcutaneous route was included as a comparator. MAP dose loading and delivery was confirmed by RP-HPLC (FIG. 26A, top panels). Images of the MAP application site taken prior to study start and on Study Days 1, 4 and 8 post application show a mild redness that largely resolves by Day 4 (FIG. 26B). Monitoring of weight shows a 10 percent weight loss by Day 4 in all 3 treatment groups, consistent with the mechanism of action of GLP-1 (FIG. 26C). Finally, plots of the plasma concentration of semaglutide over time show a faster rise to higher peak concentrations for both MAP formulations relative to SQ delivered GLP-1 (FIG. 26A). The inset in FIG. 26A plots the total area under the curve (AUC) which is a measure of the total exposure to MN array (loaded with 3.7 μg/needle) the other was a 41 MN array (loaded with 5.4 μg/needle). Tips for both arrays were formulated with Form 2. Ten animals randomized 4:3:3 across 2 cohorts received the 61 MN array, the 41 MN array, or semaglutide delivered by SQ injection as outlined in Table 14.

TABLE 14

| Group No. | Total Number Males | 04NOV Cohort 1 N | 06NOV Cohort 2 N | Test Article | Total Dose |
|---|---|---|---|---|---|
| 1 | 4 | 3 | 1 | MAP 61 MN | 220 μg |
| 2 | 3 | 2 | 1 | MAP 41 MN | 220 μg |
| 3 | 3 | 0 | 3 | SQ | 220 μg |

Plasma samples were taken at 0.5, 1, 2, 4, 6, 8, 10, 12, 24, 30, 48, 96, 120 and 168 hours post dosing and the concentration of semaglutide in the plasma quantified by RP-HPLC.

MAP dose loading and delivery was confirmed by RP-HPLC (FIG. 28, Top panels). Plots of the plasma concentration of semaglutide over time show a modestly faster absorption, with a similar T1/2 and modestly higher Cmax for MAP delivery relative to SQ delivery. The formal PK analyses shown in FIG. 28, confirm a modestly higher Cmax with a comparable Tmax and T1/2 for MAP versus SQ delivery. These data further demonstrate that MAP delivery of semaglutide could support either currently licensed dose levels or MAP specific treatment regimens.

Evaluation of Longitudinal Deployment

A longitudinal analysis of deployment data is a useful tool in determining the effects of various formulations and other parameters on deployment efficiency and deployment depth. Table 15 shows a subset of deployment data where the applicator configuration and tip volumes were held constant across a series of 4 experiments. As is clear in this group of experiments, a direct inverse relationship is seen between penetration depth and % undeployed release (Avg % PD-IVR). Additionally, when comparing different formulations, for example such as in GLP-086, three formulations with different excipients showed similar deployment efficiency and depth, but with very different compression strength, all still above the minimum threshold of 0.4N/needle, however.

consolidation. Minimal shell length, corresponding to maximum consolidation, is preferred.

A280 for GLP-1 Quantification (TM-220): The spectro-photometric method uses absorbance at 280 nm to quantify GLP-1 in solution (stock and tip print solutions). Ten µL of solution is diluted into a tube containing 690 µL of 100 mM Tris buffer to create an intermediate solution, which is then further diluted to achieve a series of samples diluted by a factor of 300-700 fold (3-5 samples per dilution). One hundred µL of each sample is then loaded into a cuvette and the absorbance measured at 280 nm. GLP-1 concentration is calculated using an extinction coefficient at 280 nm for GLP-1 of 6990 M−1 cm−1 and a path length of 1 cm. The molecular weight of GLP-1, 4113.58 g/mol, is used to convert molarity to mass.

Reverse-phase HPLC for GLP-1 Content (TM-217): This UV-RP-HPLC method employs a C8 column (Symmetry C8 Sentry Guard Cartridge, 100 Å, 5 µm, 3.9 mm×20 mm, P/N WAT054250, Waters™) to quantify GLP-1 in solution using a gradient mobile phase of water and acetonitrile, each containing 0.1% trifluoroacetic acid (TFA). Samples, prepared at approximately 0.6667 mg/mL, are run for 5 minutes at a 2.0 mL/min flow rate with detection at 280 nm. The column temperature is maintained at 35° C. with a 10 µL injection volume. The gradient begins at 30% mobile phase B for 0.08 minutes, ramps to 80% B by 2.50 minutes, holds at 80% B until 3.50 minutes, then returns to 30% B by 3.60 minutes, remaining at 30% B until the 5-minute mark. This

TABLE 15

| Test Number | Applicator Configuration | Energy/ Needle [mJ] | Piston Velocity [m/s] | Tip Fill Volume [nL] | Pre-deployment needle height [um] | Air Gap [um] | Penetration Depth (Primary-Air Gap) [um] | Avg % PD-IVR By RP-HPLC |
|---|---|---|---|---|---|---|---|---|
| GLP-190 | ISA-019: (22)_0_S-1287_3gAl | 2.1 | 12.5 | 30 | 903 | 192 | 711 | 7.40% |
| GLP-NN-004-1 | ISA-019: (22)_0_S-1287_3gAl | 2.1 | 12.5 | 30 | 927 | 260 | 667 | 8.55% |
| GLP-NN-004-1 | ISA-019: (22)_0_S-1287_3gAl | 2.1 | 12.5 | 30 | 903 | 321 | 582 | 12.04% |
| GLP-NN-004-1 | ISA-019: (22)_0_S-1287_3gAl | 2.1 | 12.5 | 30 | 939 | 365 | 574 | 24.52% |
| GLP-NN-004-1 | ISA-019: (22)_0_S-1287_3gAl | 2.1 | 12.5 | 30 | 923 | 365 | 558 | 20.19% |

MAP Inspection (TM-008): This method is used to visually inspect MAPs to quantify missing or defective Tips. A MAP with less than 10% defective/missing Tips passes inspection. Inspection is performed using a stereo microscope or digital microscope under at least 10× magnification. Exemplary defects are summarized in (FIG. 28).

Mold Dissection for Tip Length (RTM-209): The mold dissection method uses magnified images of sectioned molds to obtain measurements and morphology of the dried tips in the molds. After tip printing and drying, a mold is cross-sectioned with a razor blade in between rows of needles. The dried tips are imaged within the needle cavities using a microscope. The tip overall length and shell length are measured by image processing. The image scale is calibrated using a stage micrometer, and lengths in micrometers are calculated from the lengths measured in pixels. The shell length as a portion of overall length is an indication of assay is used to quantify the percentage release of GLP-1 from films and MAP samples or more specifically percent recovery.

Size Exclusion HPLC for GLP-1 Aggregation (TM-222): This size exclusion chromatography (SEC) method quantifies high molecular weight species of GLP-1 in solution using a Waters XBridge Protein BEH SEC column (125 Å, 2.5 µm, 7.8×300 mm, P/N 186006519). The mobile phase consists of 10% acetonitrile and 90% 100 mM sodium phosphate with 100 mM NaCl (pH 7.0), at a flow rate of 0.5 mL/min. Detection is carried out at 280 nm, with the column temperature maintained at 35° C.

Ex Vivo Deployment (TM-206): To test the functionality of MAPs for penetration of skin, dissolution, and delivery of dose, ex vivo porcine skin is used as a model substrate. The skin is harvested, excess fat and subcutaneous tissue is removed to produce a consistent thickness, hair is shaved, and the skin is frozen for storage. At the time of use, skin is thawed and equilibrated to room temperature. MAPs are applied to the skin using Vaxess' proprietary spring-loaded applicator and left on the skin for 5 minutes. Various parameters including the initial and final height of needles before and after application and the depth of tip implantation into the skin are measured by Optical Coherence Tomography and used to determine the penetration depth. The residual GLP-1 remaining on the post deployed MAP is quantified using In Vitro Release (RTM-462) and Reverse-phase HPLC for GLP-1 Content (TM-217).

Exemplary measurements are summarized below.

Pre-Deployment Needle Height: The full height of undeployed needles.

Air Gap: The space between the bottom of the adhesive of the MAP backing and the skin surface, measured while the MAP is deployed.

Post-deployment Needle Height: The height of needles after the MAP has been removed from tissue following deployment.

Deployed Tip Depth: The length between the skin surface and the apex of a deployed tip in the skin, measured post-deployment after the MAP is removed.

Height Delivered: The difference between the pre-deployment needle height and post-deployment needle height measurements, representing the length of the needle that has been deployed and left behind.

In Vitro Release (RTM-462): To quantify GLP-1 loaded on a MAP and to assess purity and stability, MAPs are eluted in release media (distilled water, or DIW) and the eluate is assayed using HPLC methods. For elution, excess backing is removed and the microarray is submerged in 1 mL (for arrays of up to 121 microneedles (MN)) or 2 mL (for arrays >121 MN) of DIW in a tube and incubated at 25° C. for 10 minutes (+/−5 minutes). Following incubation, tubes are centrifuged to pellet solids and 900 µl of supernatant is withdrawn. Eluted GLP-1 quantified by an HPLC method (TM-217).

Post Deployment In Vitro Release (RTM-462): GLP-1 remaining on the MAP following either ex vivo or in vivo deployment is quantified using the in vitro release assay. Following deployment MAPs are packaged and transferred for testing in the In Vitro Release assay with the following modifications. The excess backing is removed and trimmed patch is submerged in 0.5 mL or 1.0 mL of DIW for arrays up to 121 MN or >121 MN respectively. Following incubation at 25° C. for 10 minutes (+/−5 minutes), 400 µl of supernatant is withdrawn for quantification by HPLC (TM-217).

Microneedle Mechanical Strength (TM-404): A compression assay is used to quantify the mechanical strength of sample MAPs. Using an Instron 5942 Single Column Test frame with a 500N load cell, the entire MAP is compressed between flat steel platens at a rate of 1 mm/min until failure is reached. The two readouts from this assay are failure force, defined as the peak maximum force that is followed by a >5% drop, and Young's modulus, determined from the slope of the load-displacement curve between 1N and failure force.

Rat and Minipig PK Studies. Male Sprague-Dawley rats (n≥5) of approximately 350-450 g and male Göttingen mini-pigs of 25-30 kg (n≥3) are used in pharmacokinetic studies. On study day 0, rats receive a single dose of ~200-300 µg (or 150-225 nmol/kg) of GLP-1 delivered by the different MIMIX MAP formulations or by subcutaneous injection (s.c.) as a comparator. Minipigs receive a single dose of 2 nmol/kg, or ~200-240 µg. For rats the MAP application and the s.c. injection is to the flank, for minipigs the s.c. injections and MAP applications are given on the lower thorax. Blood samples are collected into ice cooled EDTA tubes via the jugular vein or by venous catheter at 12 timepoints over 72 hours. Plasma is processed at 4° C. and frozen. Semaglutide is measured in plasma by ELISA or LC/MS. Individual animal plasma concentration-time values are used to calculate plasma concentration-time data for each delivery route and analyzed by noncompartmental pharmacokinetics using standard PK software.

Formulation Summary for FIGS. 22-28A

TABLE 16

| FIG# | Group name | Formulation conditions included (Tip) |
|---|---|---|
| 22 | PPS-61-20 | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | PHP-61-20 | GLP-1 (180 mg/mL), Kolliphor EL (0.1%), Proline (3%), AF-647 (0.1 mg/mL) in 100 mM Tris-HCl buffer, PVP K17 (1%) |
| 23A | −024 | GLP-1 (171 mg/mL), PVP K17 (1%), Arginine-HCl (1.37%), AF-647 (0.1 mg/mL) in 100 mM MOPS buffer |
| | −027 | GLP-1 (171 mg/mL), PVP K17 (2.25%), Arginine-HCl (0.61%), AF-647 (0.1 mg/mL) in 100 mM MOPS buffer |
| | −027 | GLP-1 (171 mg/mL), PVP K17 (2.25%), Arginine-HCl (0.61%), AF-647 (0.1 mg/mL) in 100 mM MOPS buffer |
| | −031 | GLP-1 (171 mg/mL), PVP K17 (1%), Arginine-HCl (1.37%), AF-647 (0.1 mg/mL) in 100 mM MOPS buffer |
| | −031 | GLP-1 (171 mg/mL), PVP K17 (1%), Arginine-HCl (1.37%), AF-647 (0.1 mg/mL) in 100 mM MOPS buffer |
| | −038 | GLP-1 (171 mg/mL), PVP K17 (1%), Arginine-HCl (1.37%), AF-647 (0.1 mg/mL) in 100 mM MOPS buffer |
| | −060 | GLP-1 (180 mg/mL), PVP K17 (1% w/v), Kolliphor EL (0.1% w/v), Arginine-HCl (1.37%), AF-647 (0.1 mg/mL) in 100 mM MOPS buffer |
| | −105 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −109 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −109 (PHP) | GLP-1 (180 mg/mL), Kolliphor EL (0.1%), Proline (3%), AF-647 (0.1 mg/mL) in 100 mM Tris-HCl buffer, PVP K17 (1%) |

TABLE 16-continued

| FIG# | Group name | Formulation conditions included (Tip) |
|---|---|---|
| | −142 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −142 (PHP) | GLP-1 (180 mg/mL), Kolliphor EL (0.1%), Proline (3%), AF-647 (0.1 mg/mL) in 100 mM Tris-HCl buffer, PVP K17 (1%) |
| | −136 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −136 (PHP) | GLP-1 (180 mg/mL), Kolliphor EL (0.1%), Proline (3%), AF-647 (0.1 mg/mL) in 100 mM Tris-HCl buffer, PVP K17 (1%) |
| 23B | −024 | GLP-1 (171 mg/mL), PVP K17 (1%), Arginine-HCl (1.37%), AF-647 (0.1 mg/mL) in 100 mM MOPS buffer |
| | −027 | GLP-1 (171 mg/mL), PVP K17 (2.25%), Arginine-HCl (0.61%), AF-647 (0.1 mg/mL) in 100 mM MOPS buffer |
| | −027 | GLP-1 (171 mg/mL), PVP K17 (2.25%), Arginine-HCl (0.61%), AF-647 (0.1 mg/mL) in 100 mM MOPS buffer |
| | −031 | GLP-1 (171 mg/mL), PVP K17 (1%), Arginine-HCl (1.37%), AF-647 (0.1 mg/mL) in 100 mM MOPS buffer |
| | −031 | GLP-1 (171 mg/mL), PVP K17 (1%), Arginine-HCl (1.37%), AF-647 (0.1 mg/mL) in 100 mM MOPS buffer |
| | −038 | GLP-1 (171 mg/mL), PVP K17 (1%), Arginine-HCl (1.37%), AF-647 (0.1 mg/mL) in 100 mM MOPS buffer |
| | −060 | GLP-1 (180 mg/mL), PVP K17 (1% w/v), Kolliphor EL (0.1% w/v), Arginine-HCl (1.37%), AF-647 (0.1 mg/mL) in 100 mM MOPS buffer |
| | −105 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −109 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −109 (PHP) | GLP-1 (180 mg/mL), Kolliphor EL (0.1%), Proline (3%), AF-647 (0.1 mg/mL) in 100 mM Tris-HCl buffer, PVP K17 (1%) |
| | −142 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −142 (PHP) | GLP-1 (180 mg/mL), Kolliphor EL (0.1%), Proline (3%), AF-647 (0.1 mg/mL) in 100 mM Tris-HCl buffer, PVP K17 (1%) |
| | −136 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −136 (PHP) | GLP-1 (180 mg/mL), Kolliphor EL (0.1%), Proline (3%), AF-647 (0.1 mg/mL) in 100 mM Tris-HCl buffer, PVP K17 (1%) |
| 24 | −013 | GLP-1 (192 mg/mL) in DI-water |
| | −016 | GLP-1 (183 mg/mL), AF-647 (0.1 mg/mL) in DI-water |
| | −019 | GLP-1 (183 mg/mL), AF-647 (0.1 mg/mL) in DI-water |
| | −024 | GLP-1 (171 mg/mL), PVP K17 (1%), Arginine-HCl (1.37%), AF-647 (0.1 mg/mL) in 100 mM MOPS buffer |
| | −027 | GLP-1 (171 mg/mL), PVP K17 (2.25%), Arginine-HCl (0.61%), AF-647 (0.1 mg/mL) in 100 mM MOPS buffer |
| | −027 | GLP-1 (171 mg/mL), PVP K17 (2.25%), Arginine-HCl (0.61%), AF-647 (0.1 mg/mL) in 100 mM MOPS buffer |
| | −031 | GLP-1 (171 mg/mL), PVP K17 (1%), Arginine-HCl (1.37%), AF-647 (0.1 mg/mL) in 100 mM MOPS buffer |
| | −031 | GLP-1 (171 mg/mL), PVP K17 (1%), Arginine-HCl (1.37%), AF-647 (0.1 mg/mL) in 100 mM MOPS buffer |
| | −038 | GLP-1 (171 mg/mL), PVP K17 (1%), Arginine-HCl (1.37%), AF-647 (0.1 mg/mL) in 100 mM MOPS buffer |
| | −042 | GLP-1 (180 mg/mL), PVP K17 (1%), Arginine-HCl (1.37%), AF-647 (0.1 mg/mL) in 100 mM MOPS buffer |
| | −060 | GLP-1 (180 mg/mL), PVP K17 (1% w/v), Kolliphor EL (0.1% w/v), Arginine-HCl (1.37%), AF-647 (0.1 mg/mL) in 100 mM MOPS buffer |
| | −105 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −105 (PHP) | GLP-1 (180 mg/mL), Kolliphor EL (0.1%), Proline (3%), AF-647 (0.1 mg/mL) in 100 mM Tris-HCl buffer, PVP K17 (1%) |
| | −109 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −109 (PHP) | GLP-1 (180 mg/mL), Kolliphor EL (0.1%), Proline (3%), AF-647 (0.1 mg/mL) in 100 mM Tris-HCl buffer, PVP K17 (1%) |
| | −142 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |

TABLE 16-continued

| FIG# | Group name | Formulation conditions included (Tip) |
|---|---|---|
| | −142 (PHP) | GLP-1 (180 mg/mL), Kolliphor EL (0.1%), Proline (3%), AF-647 (0.1 mg/mL) in 100 mM Tris-HCl buffer, PVP K17 (1%) |
| | −136 (PPS) | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | −136 (PHP) | GLP-1 (180 mg/mL), Kolliphor EL (0.1%), Proline (3%), AF-647 (0.1 mg/mL) in 100 mM Tris-HCl buffer, PVP K17 (1%) |
| 25C | Form 1 60 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | Form 1 90 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | Form 2 60 MN | GLP-1 (180 mg/mL), Kolliphor EL (0.1%), Proline (3%), AF-647 (0.1 mg/mL) in 100 mM Tris-HCl buffer, PVP K17 (1%) |
| 26A | Form 1 or Form 1 61 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | Form 2 or Form 2 61 MN | GLP-1 (180 mg/mL), Kolliphor EL (0.1%), Proline (3%), AF-647 (0.1 mg/mL) in 100 mM Tris-HCl buffer, PVP K17 (1%) |
| | SQ or SQ injection | GLP-1 (1.1 mg/mL) in 10 mM Tri-HCl buffer |
| 26B | MAP Formulation 1 | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | MAP Formulation 2 | GLP-1 (180 mg/mL), Kolliphor EL (0.1%), Proline (3%), AF-647 (0.1 mg/mL) in 100 mM Tris-HCl buffer, PVP K17 (1%) |
| 26C | Form 1 61 MN | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | Form 2 61 MN | GLP-1 (180 mg/mL), Kolliphor EL (0.1%), Proline (3%), AF-647 (0.1 mg/mL) in 100 mM Tris-HCl buffer, PVP K17 (1%) |
| | SQ injection | GLP-1 (1.1 mg/mL) in 10 mM Tri-HCl buffer |
| 27 | Group 1 SC | GLP-1 (1.1 mg/mL) in 10 mM Tri-HCl buffer |
| | Group 2 MAP Form 1 | GLP-1 (180 mg/mL), Kolliphor EL (0.1%), Proline (0.75%), AF-647 (0.1 mg/mL) in 100 mM Tris-HCl buffer, PVP K17 (1%), NaCl (0.9%) |
| | MAP Form 2 | GLP-1 (180 mg/mL), Kolliphor EL (0.1%), Proline (3%), AF-647 (0.1 mg/mL) in 100 mM Tris-HCl buffer, PVP K17 (1%) |
| 28A | Form 2 61 MN or MAP (61-20) | GLP-1 (180 mg/mL), Kolliphor EL (0.1%), Proline (3%), AF-647 (0.1 mg/mL) in 100 mM Tris-HCl buffer, PVP K17 (1%) |
| | Form 2 41 MN or MAP (41-30) | GLP-1 (180 mg/mL), Kolliphor EL (0.1%), Proline (3%), AF-647 (0.1 mg/mL) in 100 mM Tris-HCl buffer, PVP K17 (1%) |
| | SQ injection | GLP-1 (1.1 mg/mL) in 10 mM Tri-HCl buffer |

The invention claimed is:

1. A microarray patch (MAP) and applicator system comprising:

a microarray patch (MAP) comprising:

a backing;

a plurality of microneedles extending from the backing, each of the plurality of microneedles comprising:

a tip comprising an active pharmaceutical ingredient (API), wherein each tip of the plurality of microneedles comprises a tip strength of at least about 0.4 N; and a water-soluble base configured to at least partially dissolve upon contact with a bodily fluid of a subject causing the tip to be released below a skin surface of the subject; and an applicator configured to:

maintain the MAP;

in response to an activation mechanism being activated, release a piston downward into the MAP; and push, via the piston, the MAP downward onto the skin surface of the subject such that the plurality of microneedles penetrate the skin surface and are delivered to the subject;

wherein apexes of the plurality of microneedles are delivered to the subject at a depth of at least about 300 μm below the skin surface of the subject and whereby at least about 70% of the API is delivered to the subject after release of the tip of at least a portion of the plurality of microneedles.

2. The MAP and applicator system of claim 1, wherein the piston comprises a dome-shaped face and the piston impacts and pushes the MAP downward via the dome-shaped face.

3. The MAP and applicator system of claim 1, wherein the applicator is configured to maintain the MAP in a MAP holder.

4. The MAP and applicator system of claim 3, wherein the MAP holder is configured to, as the piston is released and prior to the piston contacting the MAP, release the MAP.

5. The MAP and applicator system of claim 4, wherein the MAP holder maintains the MAP via a plurality of flex arms, each configured to flex outward to release the MAP.

6. The MAP and applicator system of claim 5, wherein the plurality of flex arms flex outward to release the MAP as the piston contacts the MAP.

7. The MAP and applicator system of claim 1, wherein each tip of the plurality of microneedles comprises at least one of:

a tip sharpness of about a 0.01 mm radius or less; or a tip stiffness of at least about 200 N/mm.

8. The MAP and applicator system of claim 1, wherein the applicator is configured to push the piston with an impact energy of about 0.3 mJ to 5 mJ per microneedle.

9. The MAP and applicator system of claim 1, wherein the tip of each of the plurality of microneedles has a length of about 450 µm or less.

10. The MAP and applicator system of claim 1, wherein the activation mechanism is configured to be activated with a force of about 12 lbF.

11. A microarray patch (MAP) and applicator system comprising:

a microarray patch (MAP) comprising:

a backing;

a plurality of microneedles extending from the backing, each of the plurality of microneedles comprising:

a tip comprising an active pharmaceutical ingredient (API) wherein each tip of the plurality of microneedles comprises at least one of a tip strength of at least about 0.4 N and a tip stiffness of at least about 200 N/mm; and a water-soluble base configured to at least partially dissolve upon contact with a bodily fluid of a subject causing the tip to be released below a skin surface of the subject; and an applicator configured to:

maintain the MAP;

in response to an activation mechanism being activated, release a piston downward into the MAP; and push, via the piston, the MAP downward onto the skin surface of the subject such that the plurality of microneedles penetrate the skin surface and are delivered to the subject;

wherein apexes of the plurality of microneedles are delivered to the subject at a depth of at least about 300 µm below the skin surface of the subject and whereby about 30% or less of the API remains on the MAP after removal from the subject.

12. The MAP and applicator system of claim 1, wherein the API is a glucagon-like peptide-1 (GLP-1) agonist.

* * * * *